United States Patent
Park et al.

(10) Patent No.: US 11,950,502 B2
(45) Date of Patent: Apr. 2, 2024

(54) COMPOUND FOR ORGANIC ELECTRIC ELEMENT, ORGANIC ELECTRIC ELEMENT USING THE SAME, AND ELECTRONIC DEVICE THEREOF

(71) Applicant: DUK SAN NEOLUX CO., LTD., Cheonan-si (KR)

(72) Inventors: Hyoung Keun Park, Chuncheon-si (KR); Yun Suk Lee, Seongnam-si (KR); Ki Ho So, Cheonan-si (KR); Jong Gwang Park, Cheonan-si (KR); Yeon Seok Jeong, Gangwon-do (KR); Jung Hwan Park, Hwaseong-si (KR); Sun Hee Lee, Hwaseong-si (KR); Hak Young Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 129 days.

(21) Appl. No.: 17/233,438

(22) Filed: Apr. 17, 2021

(65) Prior Publication Data
US 2021/0242408 A1     Aug. 5, 2021

Related U.S. Application Data

(62) Division of application No. 15/737,449, filed as application No. PCT/KR2017/006534 on Jun. 21, 2017, now Pat. No. 10,998,502.

(30) Foreign Application Priority Data

Jun. 28, 2016    (KR) .................. 10-2016-0080495
Oct. 5, 2016    (KR) .................. 10-2016-0128477

(51) Int. Cl.
*H01L 51/00*     (2006.01)
*C07D 209/82*     (2006.01)
(Continued)

(52) U.S. Cl.
CPC ......... *H10K 85/649* (2023.02); *C07D 209/82* (2013.01); *C07D 209/88* (2013.01); *C07D 333/76* (2013.01); *C09K 11/06* (2013.01); *H10K 50/00* (2023.02); *H10K 50/15* (2023.02); *H10K 50/16* (2023.02); *H10K 50/17* (2023.02); *H10K 99/00* (2023.02); *C07D 419/10* (2013.01);
(Continued)

(58) Field of Classification Search
None
See application file for complete search history.

(56) References Cited

U.S. PATENT DOCUMENTS

2003/0117071 A1 * 6/2003 Lee .................. H01L 51/5253
                                                                     313/512
2018/0358563 A1 * 12/2018 Park ....................... C09K 11/06

FOREIGN PATENT DOCUMENTS

| KR | 10-2010-0006072 | * | 1/2010 |
| KR | 10-1614739 | * | 4/2016 |
| WO | WO-2014/042420 A1 | * | 3/2014 |

OTHER PUBLICATIONS

Machine English translation of Kim et al. (KR-10-2010-00060072). Aug. 22, 2023.*

* cited by examiner

*Primary Examiner* — Jay Yang
(74) *Attorney, Agent, or Firm* — Vorys, Sater, Seymour and Pease LLP; Mih Suhn Koh

(57) ABSTRACT

Provided is a novel compound capable of improving the luminous efficiency, stability and life span of a device, an organic electric element using the same, and an electronic device thereof.

20 Claims, 1 Drawing Sheet

(51) Int. Cl.
*C07D 209/88* (2006.01)
*C07D 333/76* (2006.01)
*C09K 11/06* (2006.01)
*H01L 51/50* (2006.01)
*H10K 50/00* (2023.01)
*H10K 50/15* (2023.01)
*H10K 50/16* (2023.01)
*H10K 50/17* (2023.01)
*H10K 85/60* (2023.01)
*H10K 99/00* (2023.01)
*C07D 419/10* (2006.01)
*C07D 419/12* (2006.01)
*C07D 419/14* (2006.01)
*H10K 10/46* (2023.01)
*H10K 30/00* (2023.01)

(52) U.S. Cl.
CPC ......... *C07D 419/12* (2013.01); *C07D 419/14* (2013.01); *H10K 10/462* (2023.02); *H10K 30/00* (2023.02)

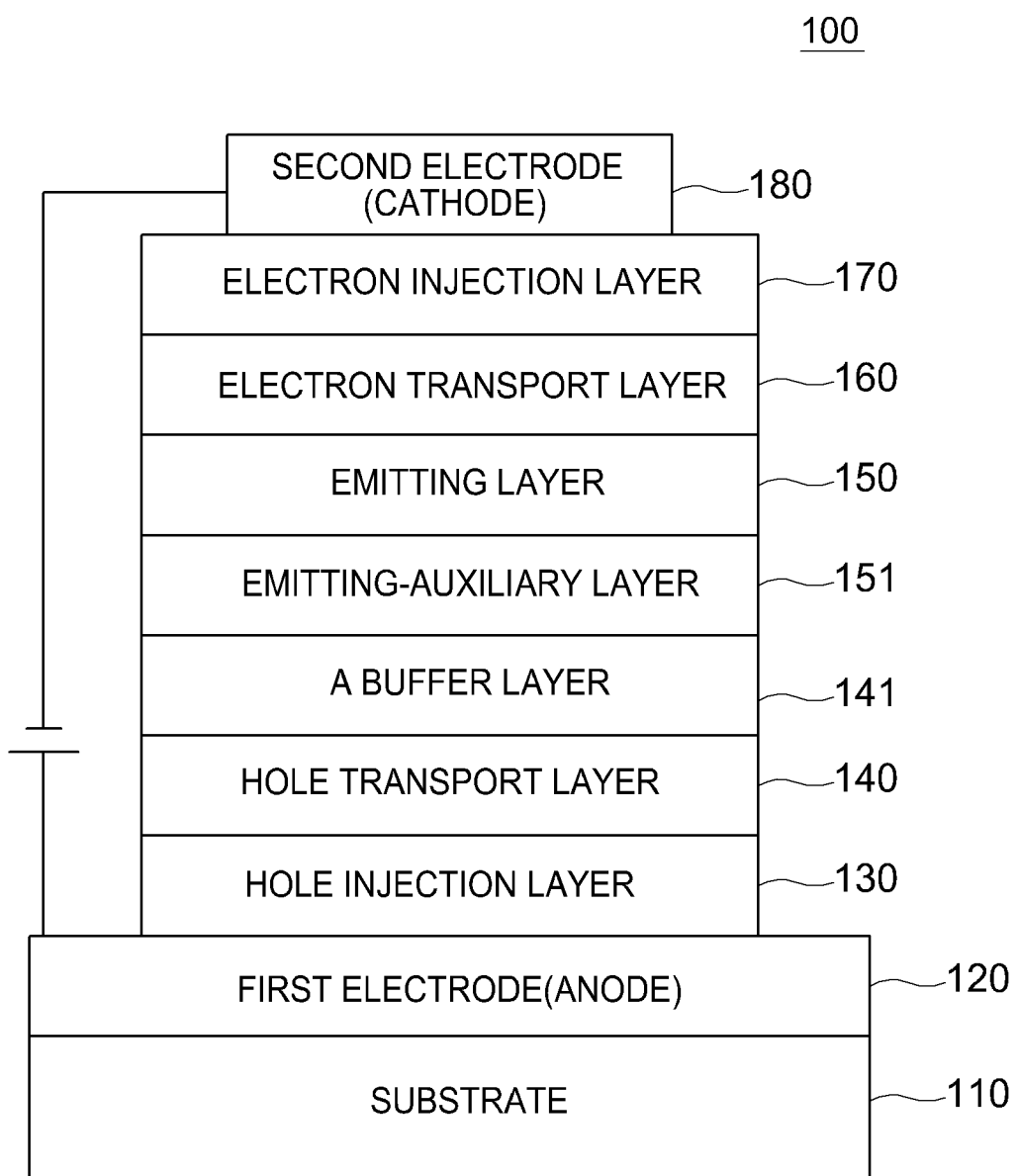

COMPOUND FOR ORGANIC ELECTRIC ELEMENT, ORGANIC ELECTRIC ELEMENT USING THE SAME, AND ELECTRONIC DEVICE THEREOF

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may comprise a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

The most problematic issues in an organic electric element are life span and efficiency, and as the display becomes larger, such efficiency and life span problems must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, in order to solve the emission problem in the a hole transport layer in recent organic electric element, an emitting-auxiliary layer must be present between the hole transport layer and the emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has a low T1 value. As a result, the exciton generated in the emitting layer is transferred to the hole transport layer, resulting in charge unbalance in the emitting layer, and light is emitted at the interface of the hole transport layer.

When light is emitted from the interface of the hole transport layer, the color purity and efficiency of the organic electronic device are lowered and the life span is shortened. Therefore, it is urgently required to develop an emitting-auxiliary layer having a high T 1 value and a HOMO level between the HOMO energy level of the hole transport layer and the HOMO energy level of the emitting layer.

In addition, it is necessary to develop a hole injection layer material that retards penetration/diffusion of metal oxides from an anode electrode (ITO) into an organic material layer, which is one cause for the shortened life span of an organic electric element, and has stability against Joule heating generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus it is necessary to develop a material that is durable to such a deposition method, that is, a highly heat-resistant material.

That is, in order to sufficiently exhibit the excellent characteristics of the organic electric element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electric element has not been sufficiently developed yet. Therefore, development of new materials is continuously required, and development of materials for the emitting-auxiliary layer and the hole transport layer is urgently required.

PRIOR ART DOCUMENT

Patent Documents (Patent Document 0001) KR1020130076842 A

DETAILED DESCRIPTION OF THE INVENTION

Summary

In order to solve the problems of the background art described above, an aspect of the present invention is to provide a compound which allows an organic electric element to further improve high luminous efficiency, stability and life span.

An object of the present invention is to provide a compound, an organic electric element using the same and an electronic device thereof.

Technical Solution

The present invention provides a compound represented by Formula (1) below and a composition for an emitting-auxiliary layer comprising the same and an organic electric element characterized in having the same.

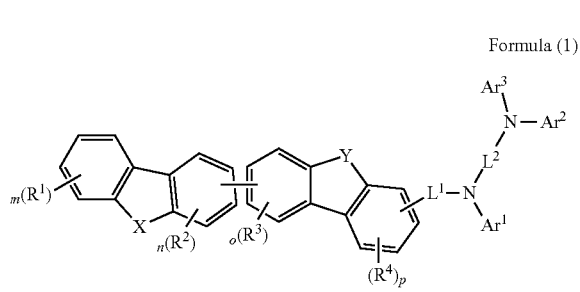

Formula (1)

Effects of the Invention

By using the compound according to the present invention, it is possible to achieve a high luminous efficiency, a low driving voltage, and a high heat resistance of the element, and can greatly improve the color purity and lifetime of the element.

BRIEF DESCRIPTION OF THE DRAWINGS

The FIGURE illustrates an example of an organic electric element according to the present invention.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, comprises fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, comprises an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and comprises a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxy group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and Polycyclic aromatic group, and may also be formed in conjunction with an adjacent group. Examples of "aryl group" may comprise a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and comprises at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, comprises any one of monocyclic and Polycyclic rings, and may comprise heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may comprise a ring containing $SO_2$ instead of carbon consisting of cycle. For example, "heterocyclic group" comprises compound below.

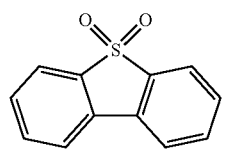 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and comprises a saturated or unsaturated ring.

Other hetero compounds or hetero radicals other than the above-mentioned hetero compounds contain, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

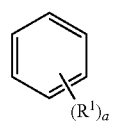

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$'s may be the same and different, when a is an integer of 4 to 6, and is linked to the benzene ring in a similar manner, whereas the indication of hydrogen bound to the carbon forming the benzene ring is omitted.

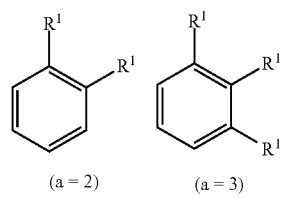

(a = 2)   (a = 3)

Unless otherwise expressly stated, the terms "ortho", "meta", and "para" used in the present invention refer to the substitution positions of all substituents, and the ortho position indicates the position of the substituent immediately adjacent to the compound, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

[Example of Ortho-Position]

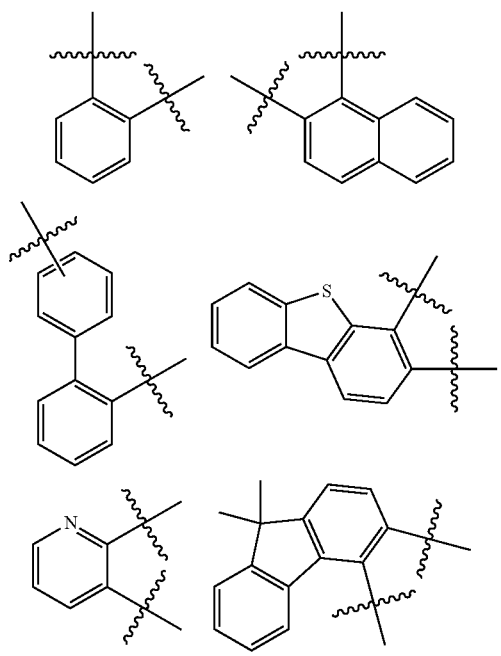

[Example of Meta-Position]

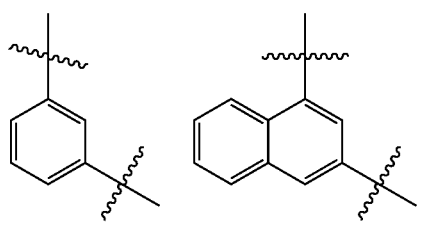

-continued

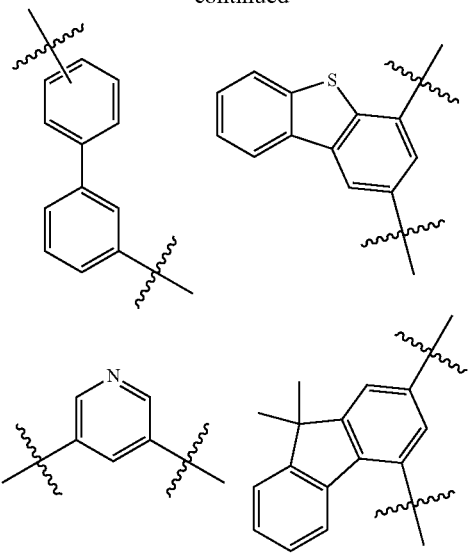

[Example of Para-Position]

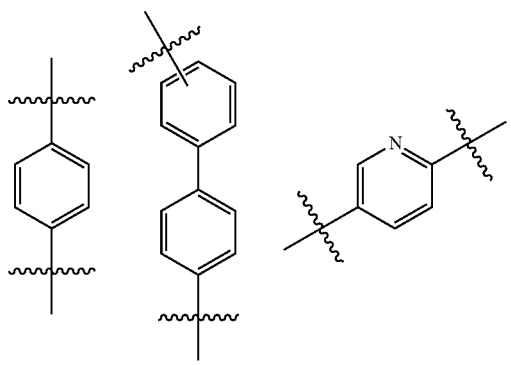

Hereinafter, a compound according to an aspect of the present invention and an organic electric element comprising the same will be described.

The present invention provides a compound represented Formula (1) below. Formula (1)

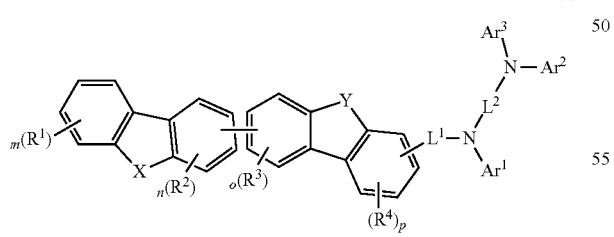

In Formula (1),
1) m is an integer of 0 to 4, and n, o and p are an integer of 0 to 3,
when m, n, o or p are 1 or more, $R^1$, $R^2$, $R^3$, and $R^4$ are each independently selected from a hydrogen; a deuterium; a halogen; the group consisting of a $C_6$-$C_6$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P), or an adjacent plurality of $R^1$ or a plurality of $R^2$ or a plurality of $R^3$ or a plurality of $R^4$ may combine to each other to form an aromatic or a heteroaromatic ring.

2) X and Y are O, S, NR' or CR'R", wherein R' and R" are independently hydrogen; a $C_6$-$C_6$ aryl group; a fluorenyl group; a $C_3$-$C_{60}$ heterocyclic group; or a $C_1$-$C_{50}$ alkyl group; and R' and R" may be bonded to each other to form a spiro.

3) $L^1$ is independently selected from the group consisting of a single bond, a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group.

4) $L^2$ is independently selected from the group consisting of a single bond, a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group.

5) $Ar^1$, $Ar^2$ and $Ar^3$ are each independently selected from the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), and also $Ar^2$ and $Ar^3$, or $Ar^3$ and $L^2$, $Ar^2$ and $L^2$, $Ar^1$ and $L^1$, $Ar^1$ and $L^2$ may be bonded to each other to form a ring.

(wherein, the aryl group, fluorenyl group, arylene group, heterocyclic group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of thereof.)

The present invention comprises a compound wherein the compound represented by Formula (1) is represented by the following Formulas (2) to (5).

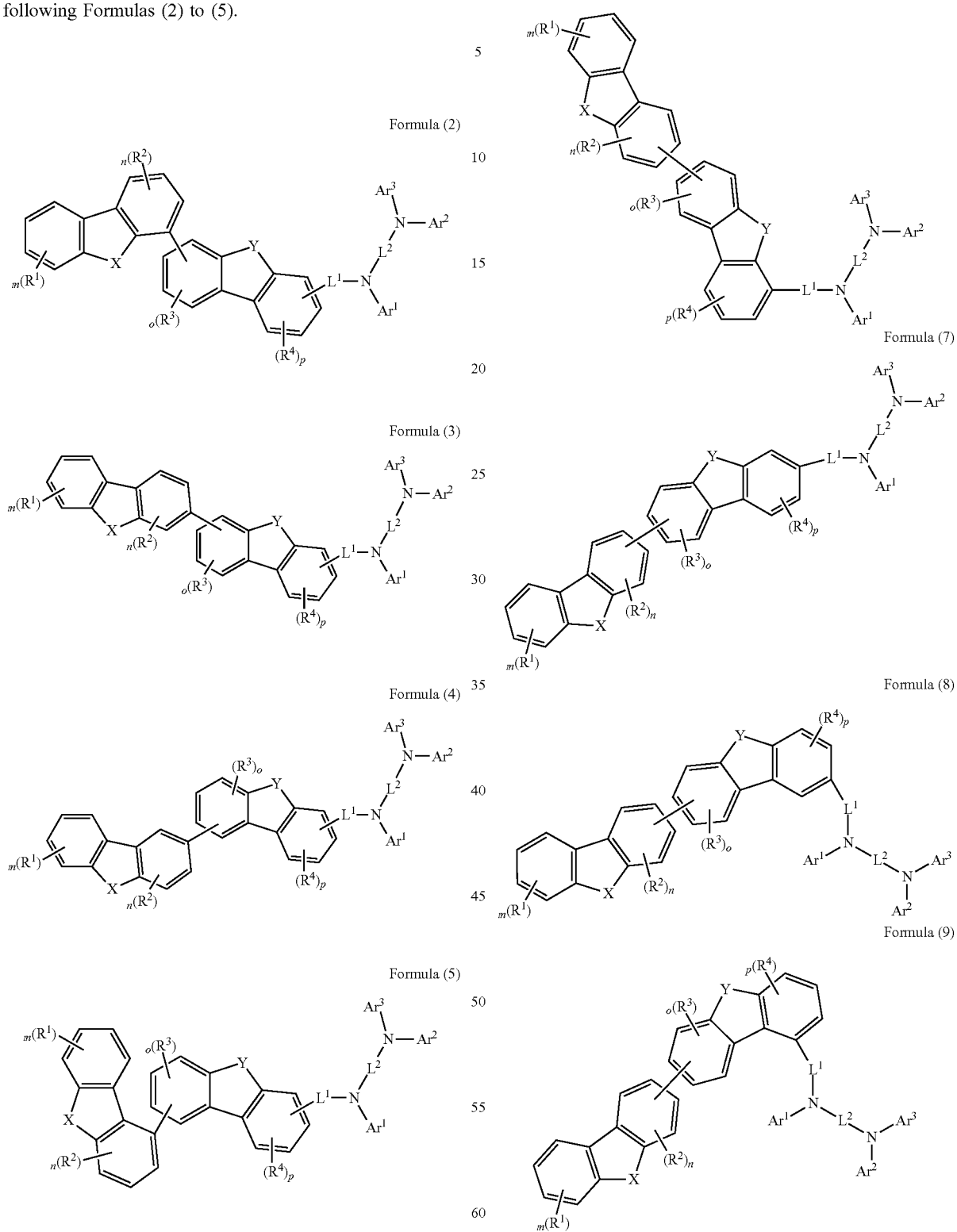

{In Formula (2) to Formula (5),
R¹, R², R³, R⁴, m, n, o, p, L¹, L², Ar¹, Ar², Ar³, X and Y are the same as defined above.}

In the present invention, the compound represented by Formula (1) provides a compound represented by the following formula (6) to (9).

{In Formula (6) to Formula (9),
R¹, R², R³, R⁴, m, n, o, p, L, L², Ar¹, Ar², Ar³, X and Y are the same as defined above.}

Also, the present invention provides a compound, wherein neighboring substituent connecting position of ring containing Y in Formula (1) is represented by any one of the following structural formulas [A-1] to [A-16].
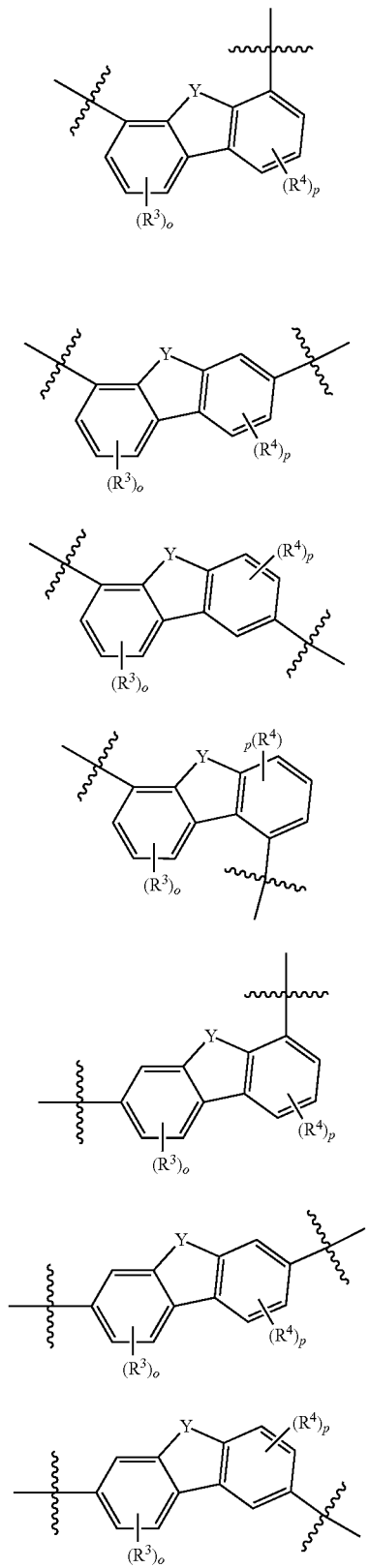
[A-1]
[A-2]
[A-3]
[A-4]
[A-5]
[A-6]
[A-7]
-continued
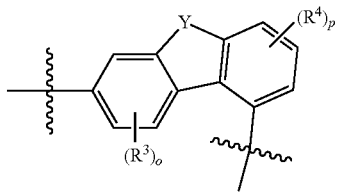
[A-8]
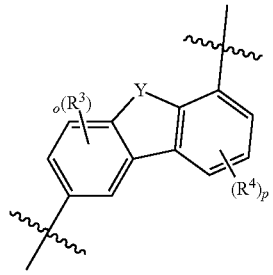
[A-9]
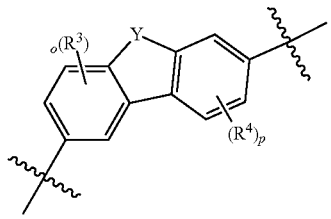
[A-10]
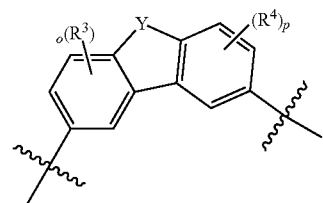
[A-11]
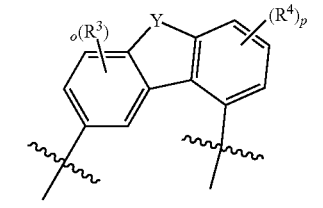
[A-12]
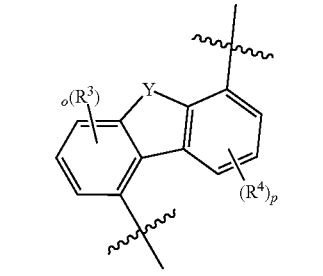
[A-13]
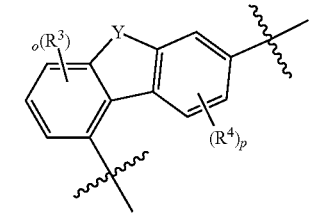
[A-14]

-continued

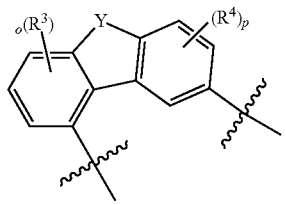
[A-15]

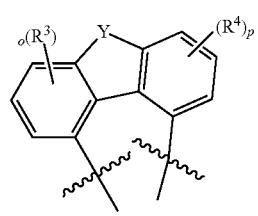
[A-16]

{In Formulas [A-1] to [A-16],
R$^3$, R$^4$, o, p and Y are the same as defined above.}

Also, the compound represented by Formula (1) comprises a compound represented by Formula (10) to Formula (13) below.

Formula (10)

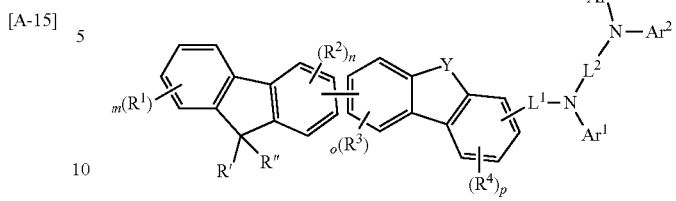

Formula (11)

Formula (12)

-continued

Formula (13)

{In Formula (10) to Formula (13),
R$^1$, R$^2$, R$^3$, R$^4$, m, n, o, p, L$^1$, L$^2$, Ar$^1$, Ar$^2$, Ar$^3$, X and Y are the same as defined above.}

Also, the compound represented by Formula (1) provides a compound represented by Formula (14) to Formula (17) below.

Formula (14)

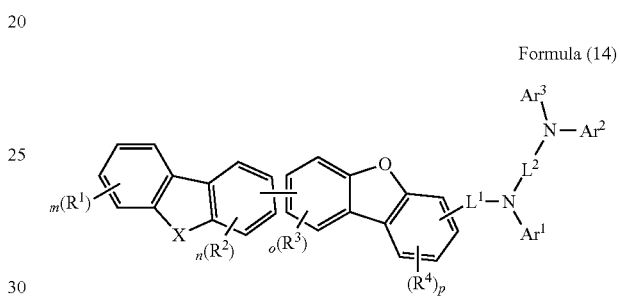

Formula (15)

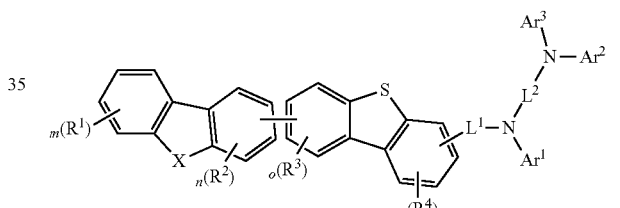

Formula (16)

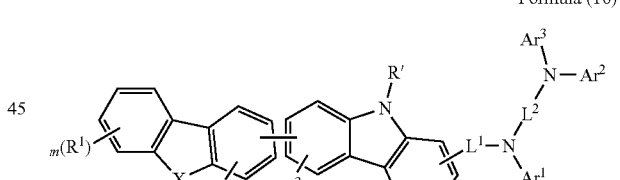

Formula (17)

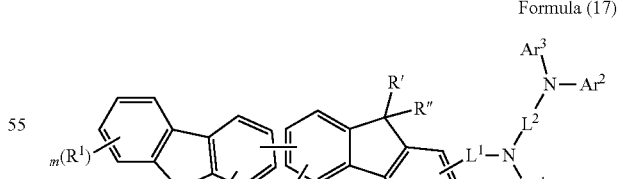

{In Formula (14) to Formula (17),
R$^1$, R$^2$, R$^3$, R$^4$, m, n, o, p, L$^1$, L$^2$, Ar$^1$, Ar$^2$, Ar$^3$, and X are the same as defined above.}

Also, the compound represented by Formula (1) provides a compound represented by Formula (18) to Formula (21) below.

Formula (18)
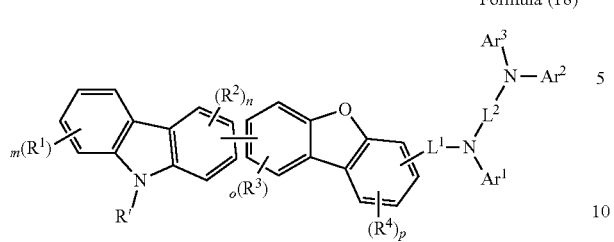

Formula (19)
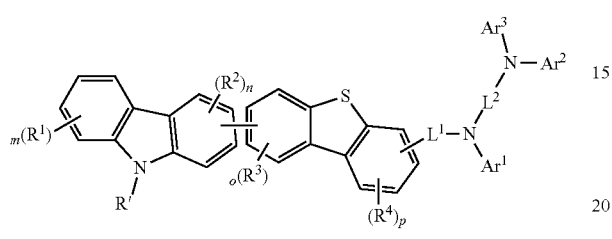

Formula (20)
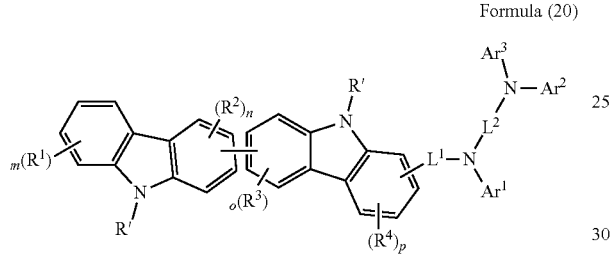

Formula (21)
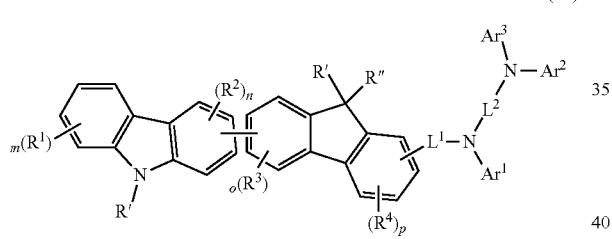

{In Formula (18) to Formula (21), $R^1$, $R^2$, $R^3$, $R^4$, m, n, o, p, $L^1$, $L^2$, $Ar^1$, $Ar^2$ and $Ar^3$ are the same as defined above.}

Also, the compound represented by Formula (1) comprises a compound represented by Formula (22A)

Formula (22A)
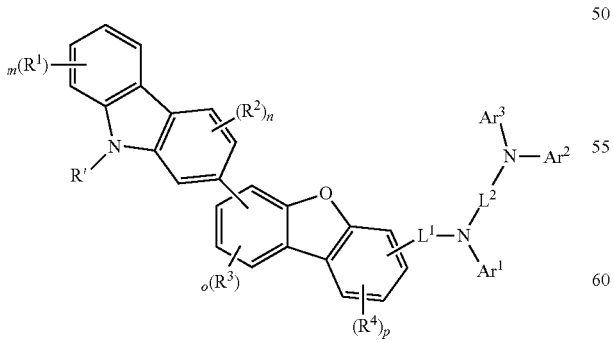

{In Formula (22A), $R^1$, $R^2$, $R^3$, $R^4$, m, n, o, p, $L^1$, $L^2$, $Ar^1$, $Ar^2$, $Ar^3$ and Y are the same as defined above.}

The compound represented by Formula (1) comprises a compound represented by Formula (22) to Formula (37) below.

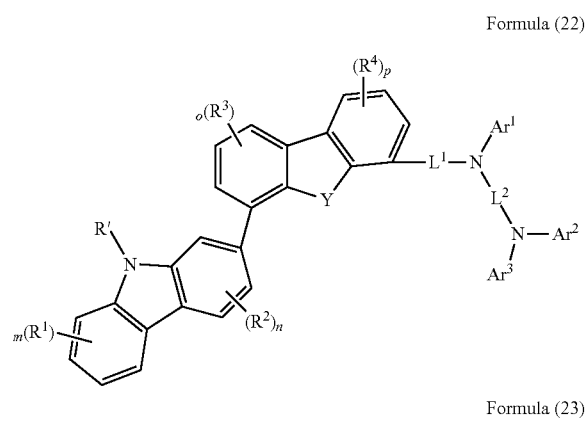

Formula (26)
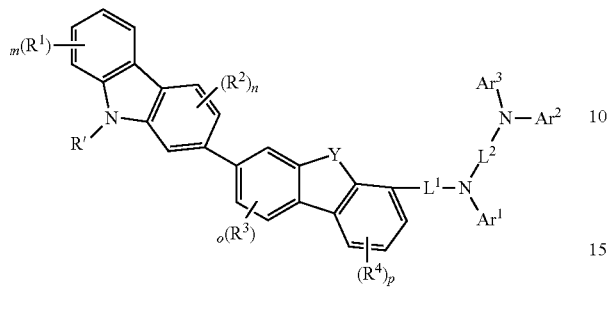
Formula (27)
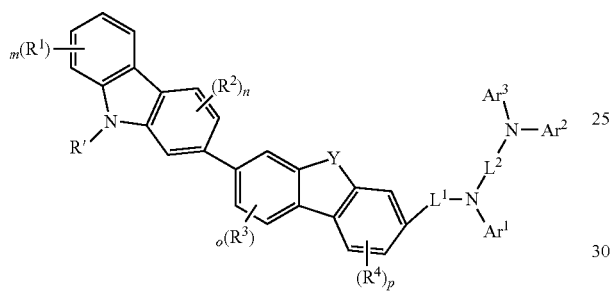
Formula (28)
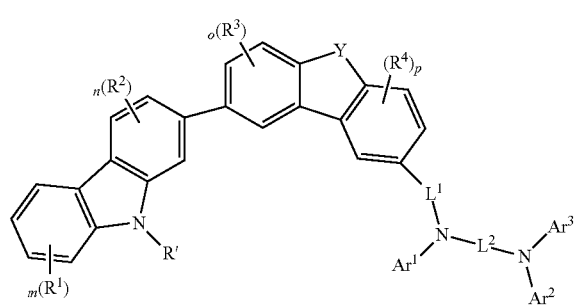
Formula (29)
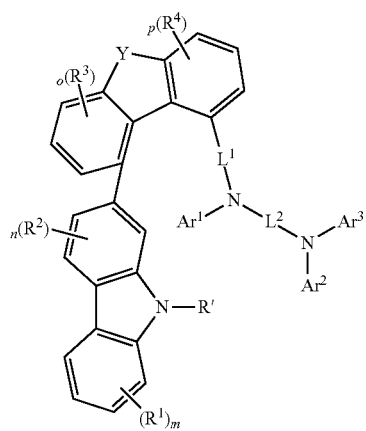
Formula (30)
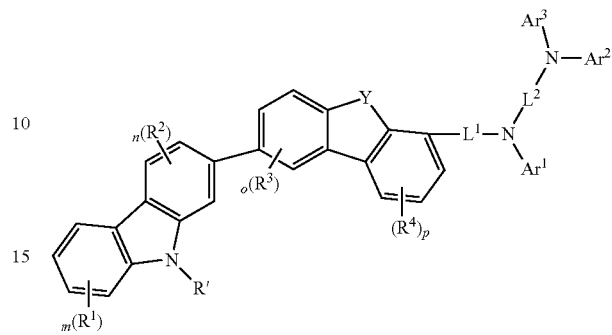
Formula (31)
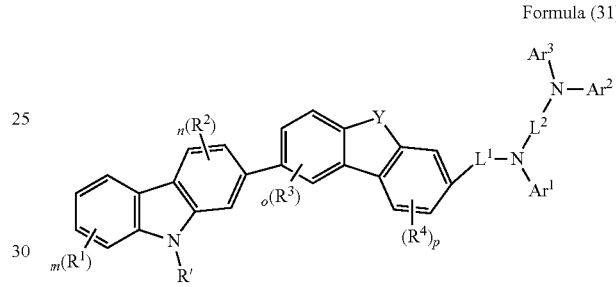
Formula (32)
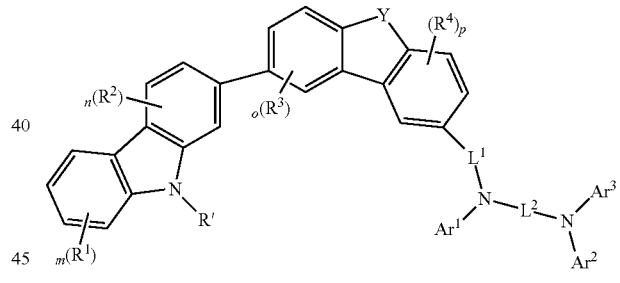
Formula (33)
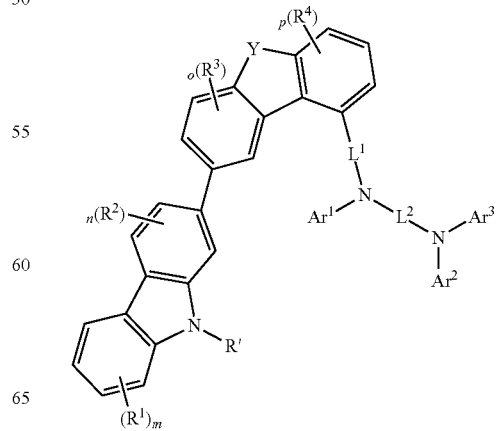

Formula (34)
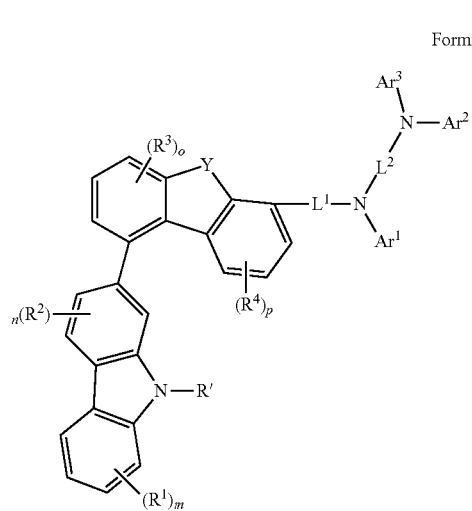
Formula (35)
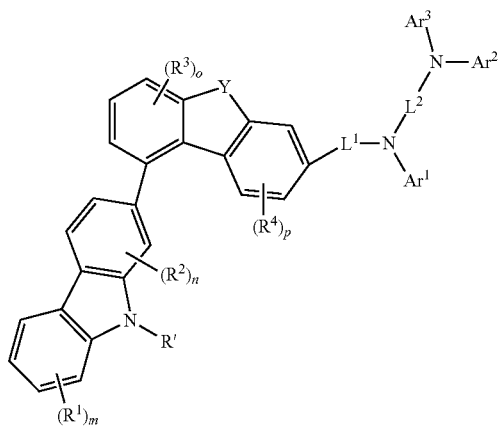
Formula (36)
Formula (37)
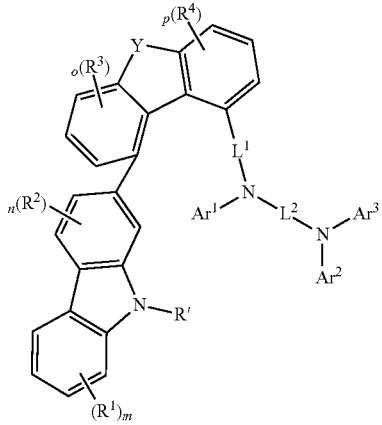
{In Formula (22) to Formula (37),
$R^1$, $R^2$, $R^3$, $R^4$, m, n, o, p, $L^1$, $L^2$, $Ar^1$, $Ar^2$, $Ar^3$ and Y are the same as defined above.}
The present invention also provides a compound wherein $L^1$ and $L^2$ of Formula (1) are any one of the following Formulas (B-1) to (B-12).
(B-1)
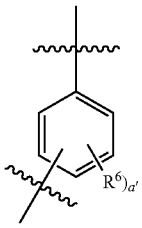
(B-2)
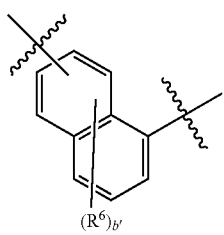
(B-3)
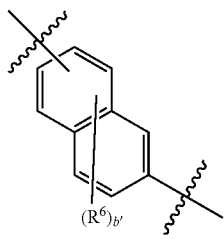

-continued (B-4)
(B-5)
(B-6)
(B-7)
(B-8)

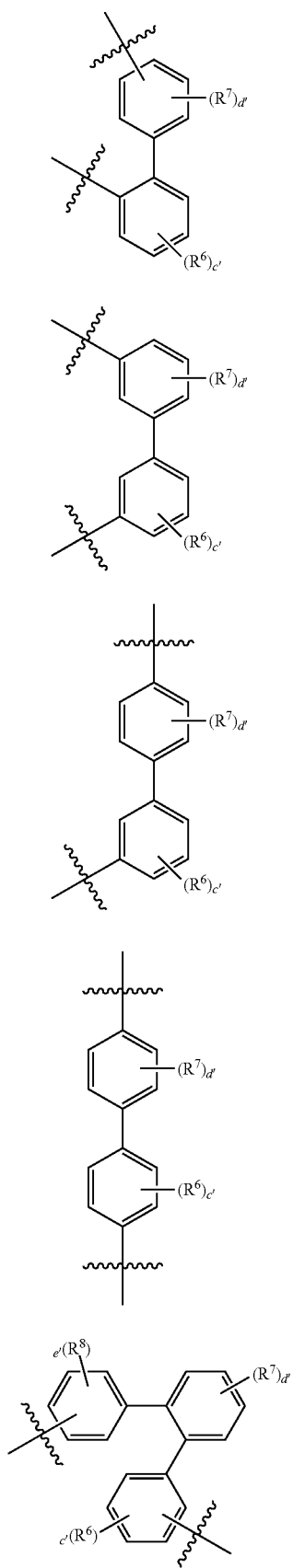

-continued (B-9)
(B-10)
(B-11)
(B-12)

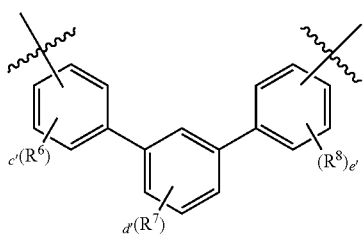
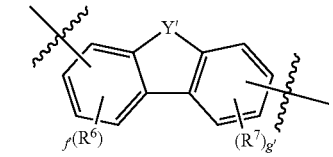
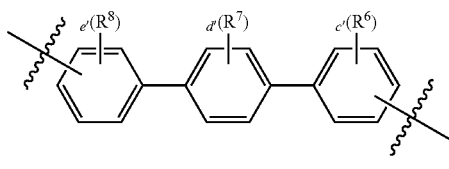
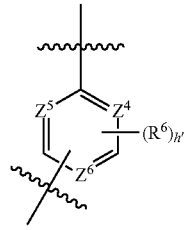

{In Formula (B-1) to Formula (B-12), 1) a', c', d' and e' are an integer of 0 to 4, and b' is an integer of 0 to 6, and h' is an integer of 0 to 1.

2) $R^6$, $R^7$ and $R^8$ are the same or different from each other, and are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_6$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)) (wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P), with the proviso that a', b', c', d', e', f' and g' are 2 or more, and d is 2, and are each in plural and are the same or different from each other, and a plurality of $R^6$ or a plurality of $R^7$ or a plurality of R' or a plurality of $R^4$ or a plurality of $R^5$ may be bonded to each other to form a ring, or adjacent $R^6$ and $R^7$, or adjacent $R^7$ and $R^8$ may be bonded to each other to form an aromatic or a heteroaromatic ring.

3) Y' is NR', O, S, or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; and R' and R" may be bonded to each other to form a spiro, 4) $Z^4$, $Z^5$ and $Z^6$ are CR' or N, and at least one is N.}

The present invention also provides a compound wherein at least one of $L^1$ and $L^2$ in Formula (1) is substituted at a meta position.

In the present invention, the compound represented by Formula (1) comprises compounds represented by the following Formulas (P-1) to (P-128).

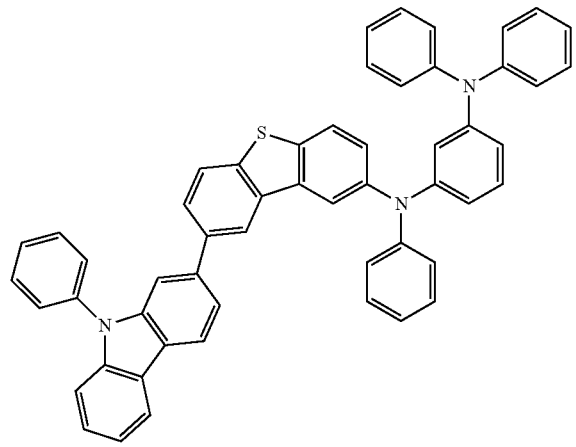

P-1

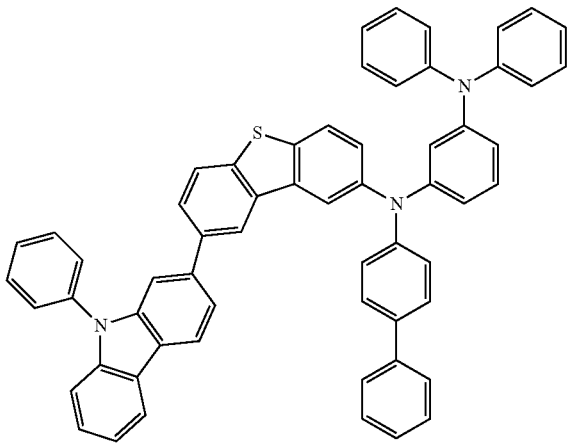

P-2

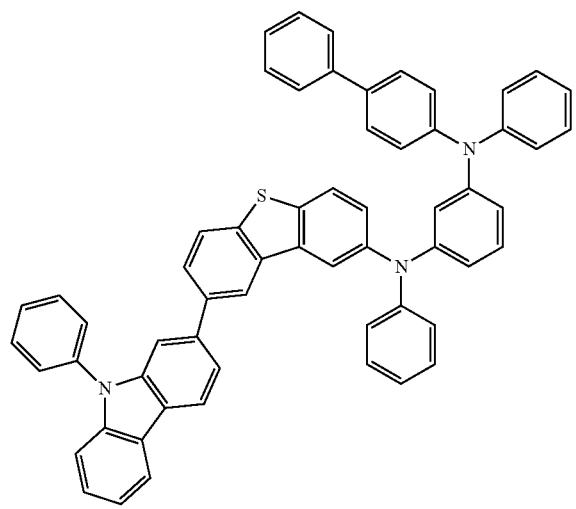

P-3

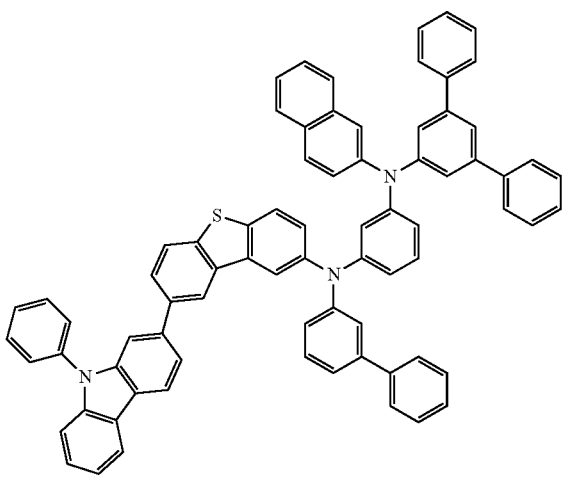

P-4

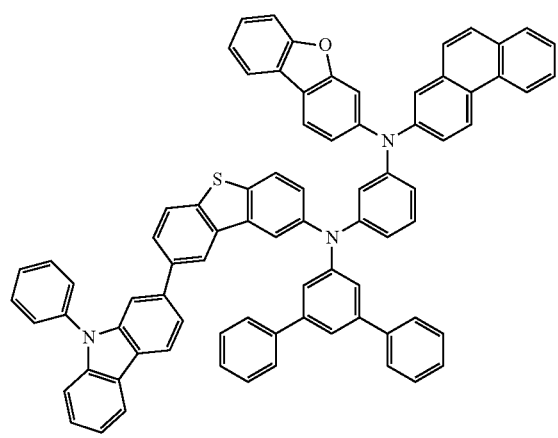

P-5

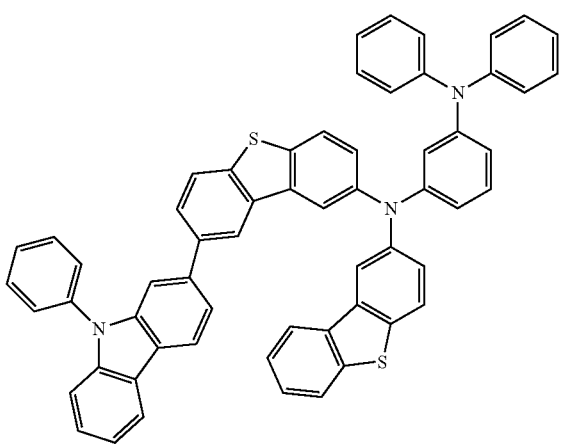

P-6

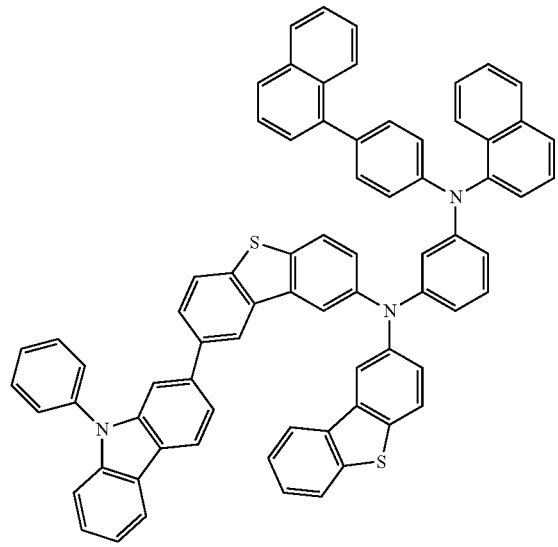
P-7
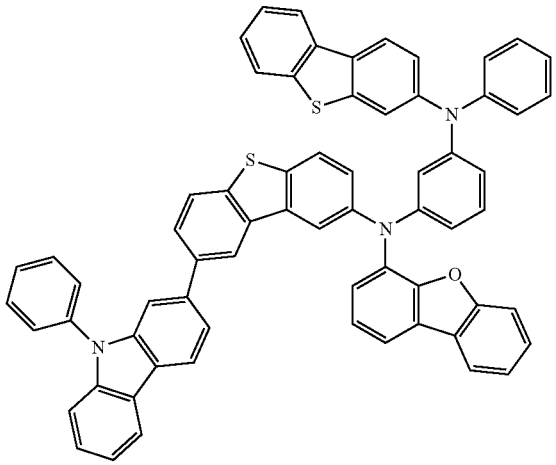
P-8
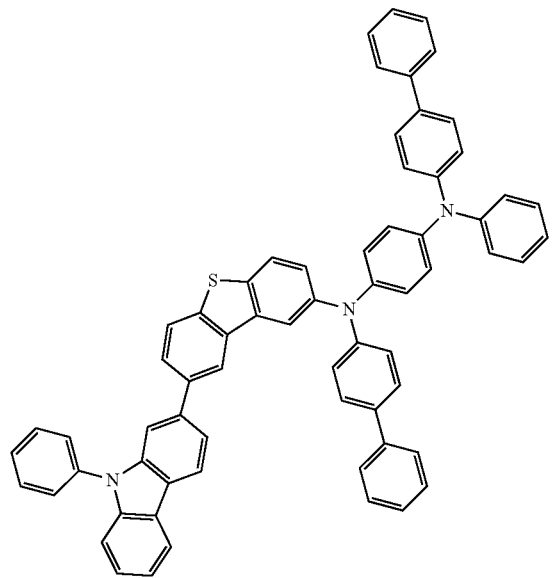
P-9
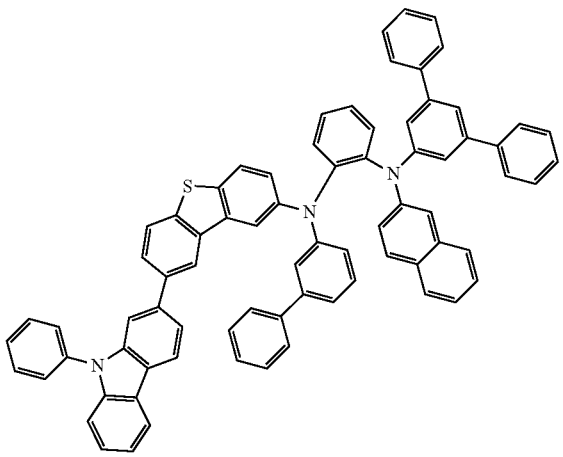
P-10

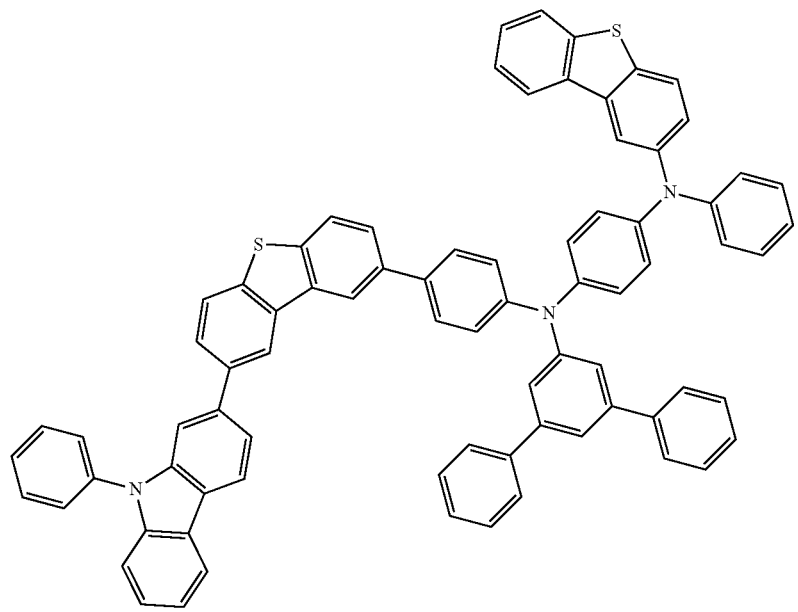
P-11
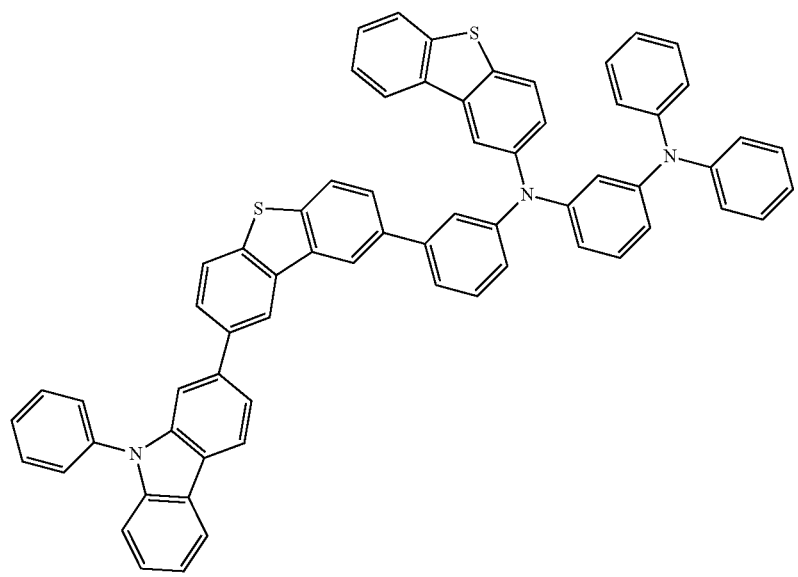
P-12

P-13
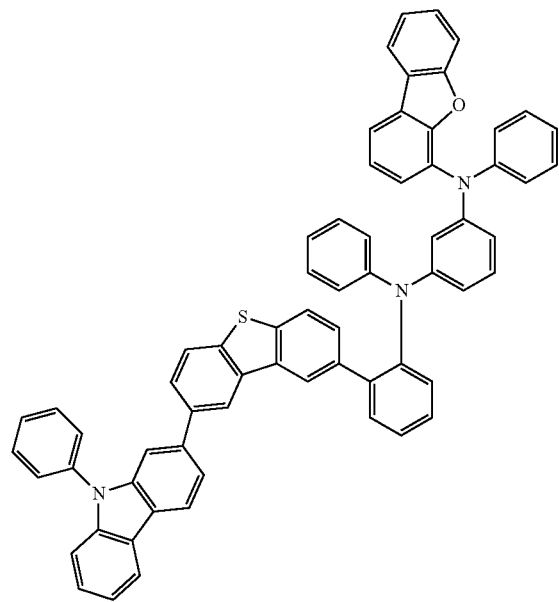
P-14
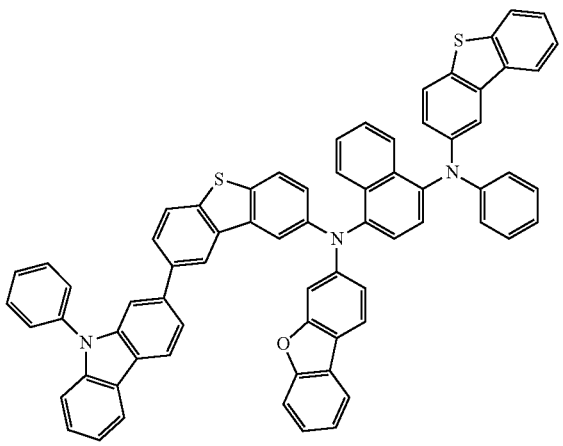
P-15
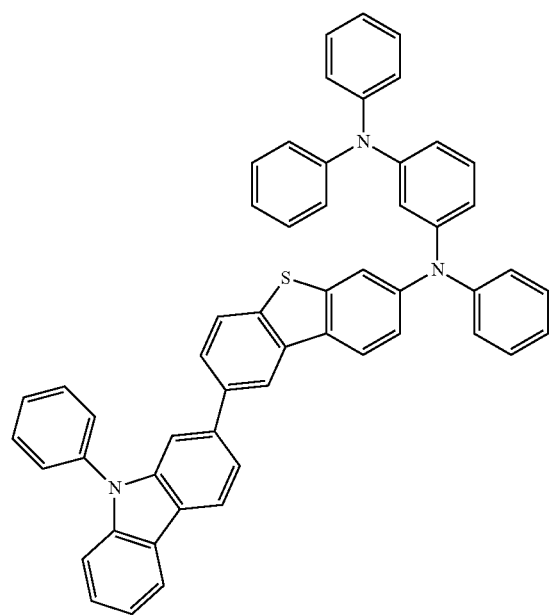
P-16
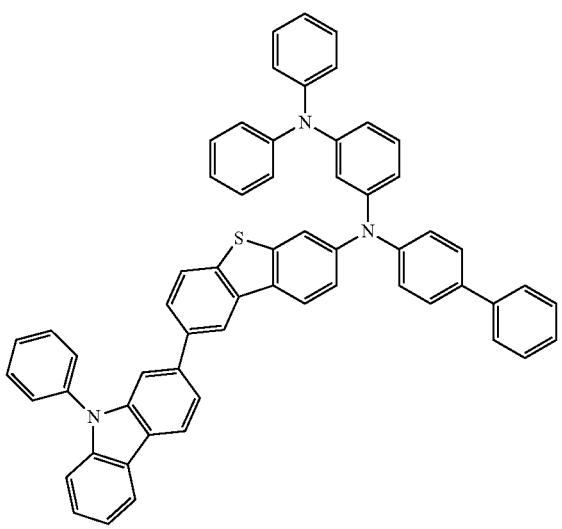

P-17
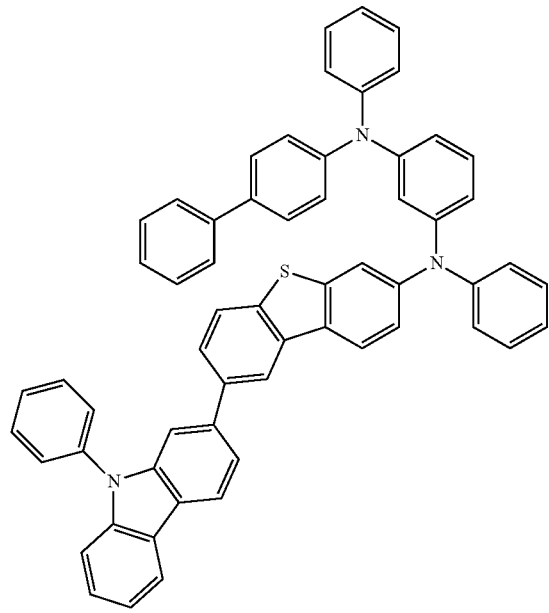
P-18
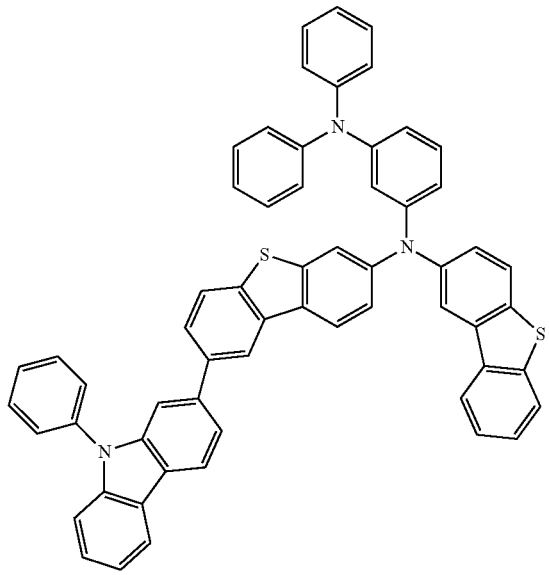
P-19
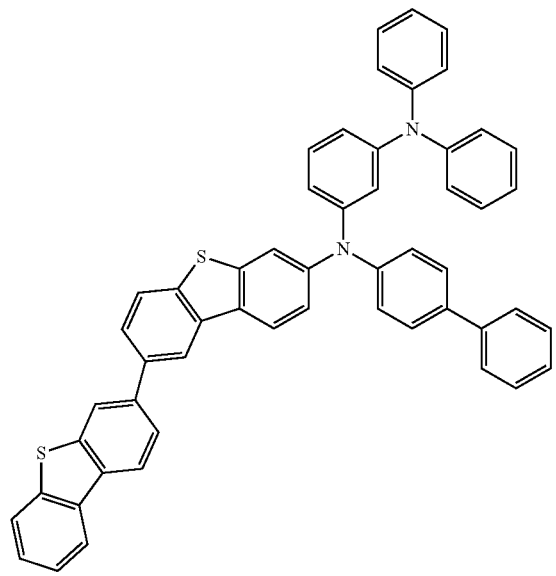
P-20
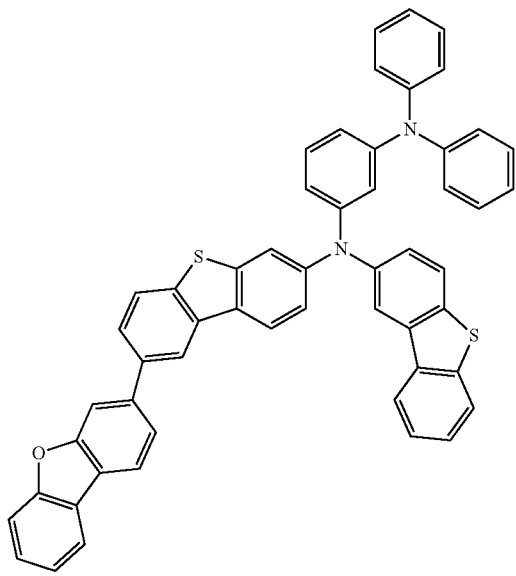

-continued
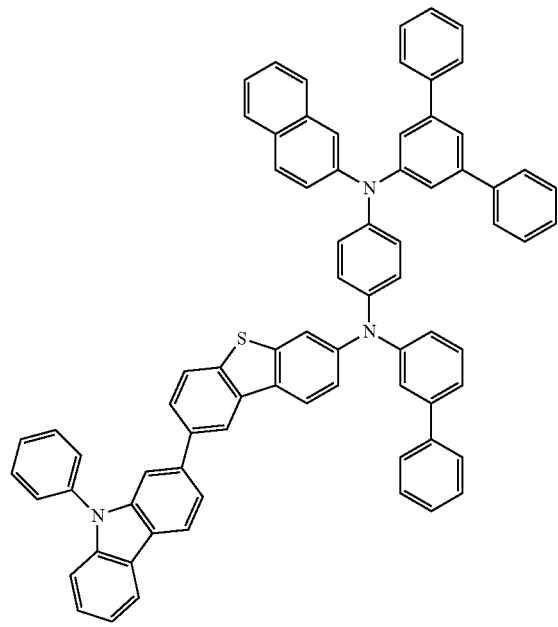
P-22
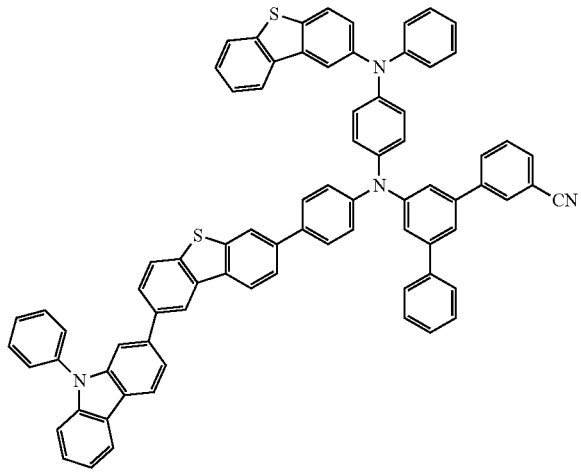
P-22
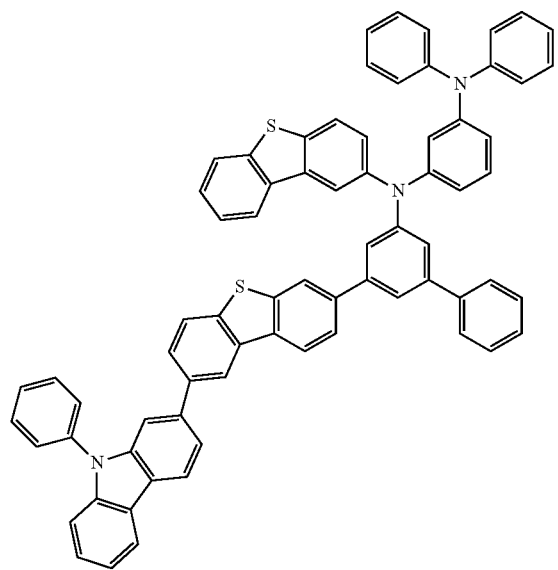
P-23
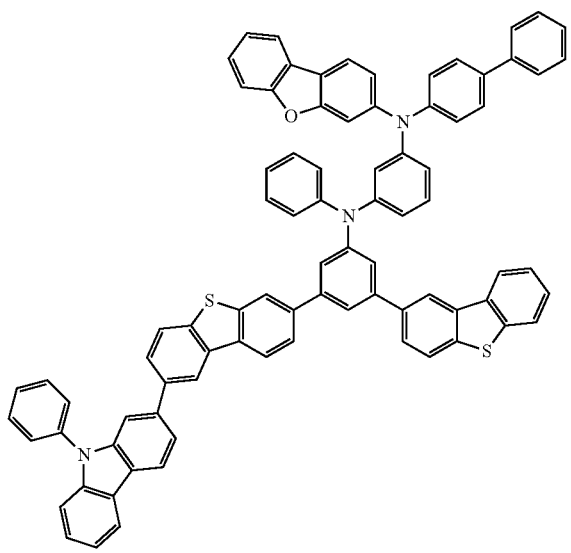
P-24

-continued
P-25
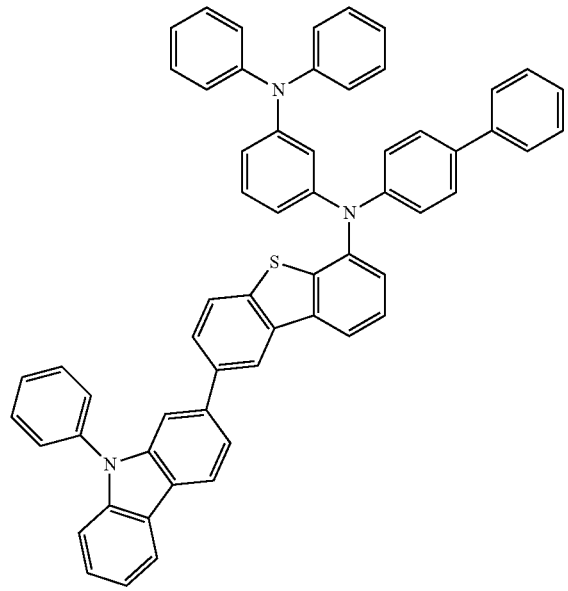
P-26
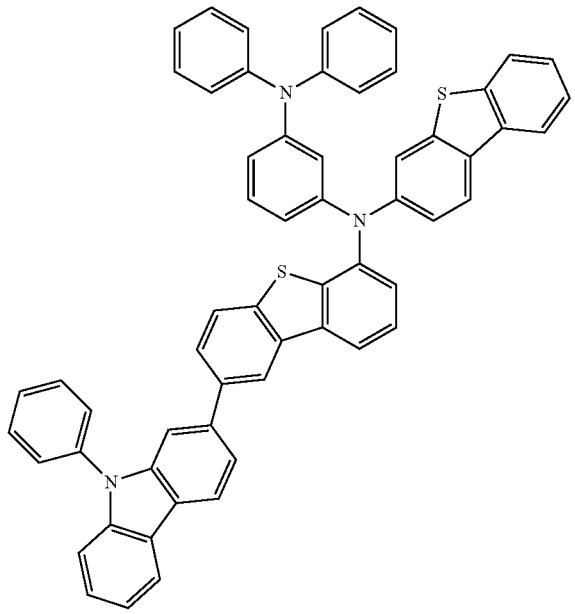
P-27
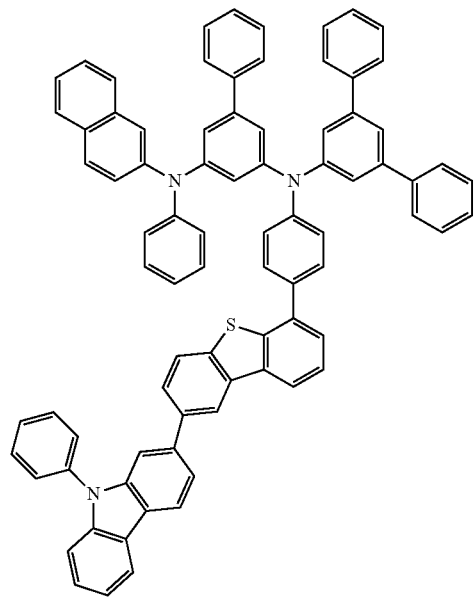
P-28
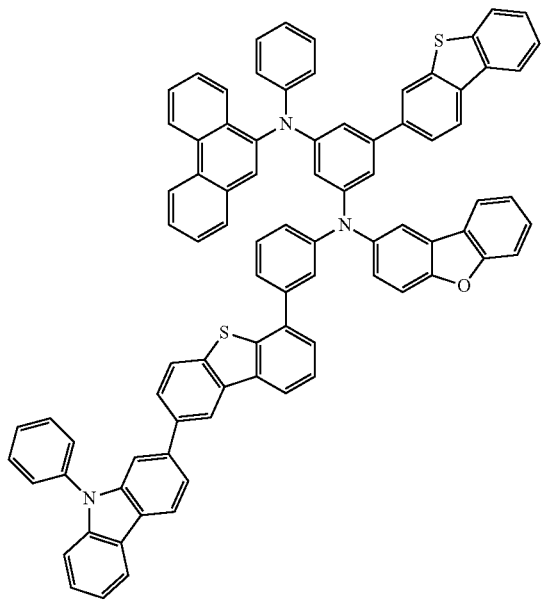
P-29
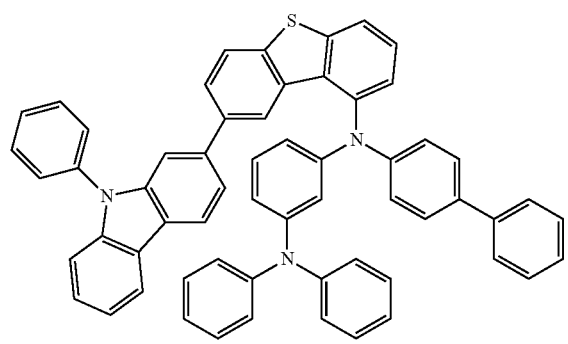
P-30
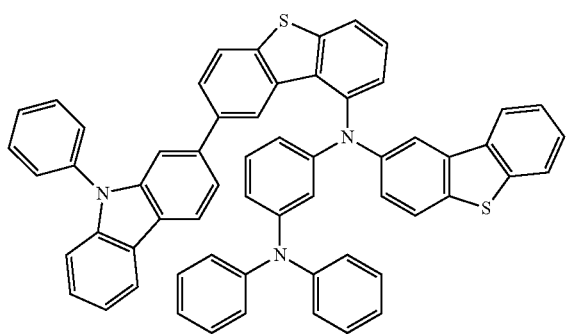

-continued
P-31
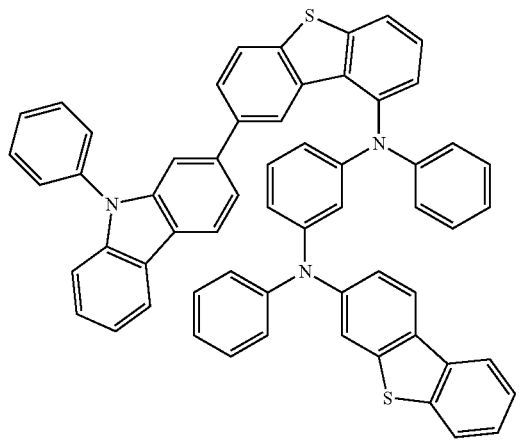
P-32
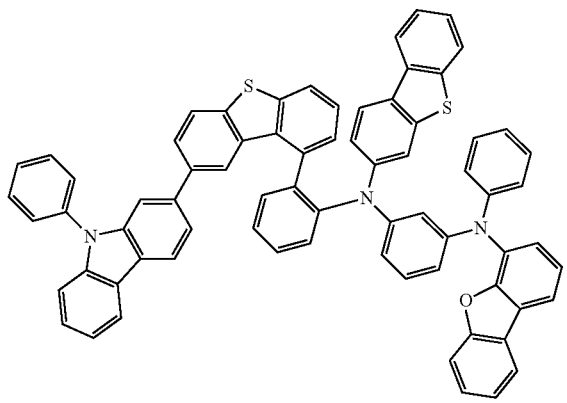
P-33
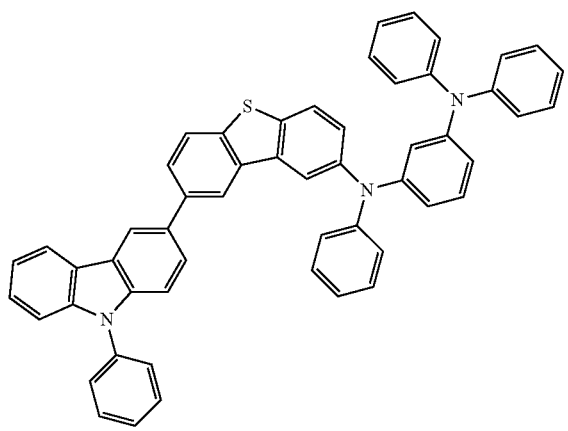
P-34
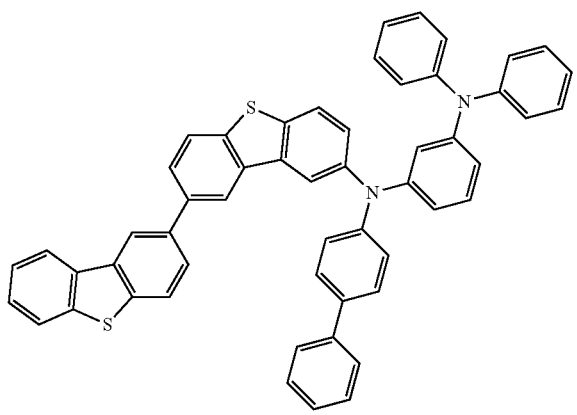
P-35
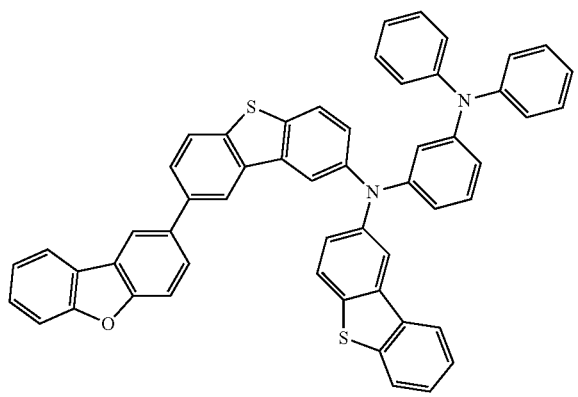
P-36
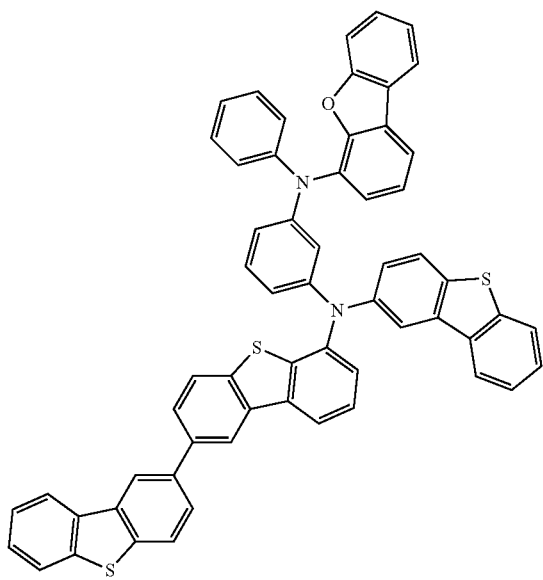

-continued
P-37
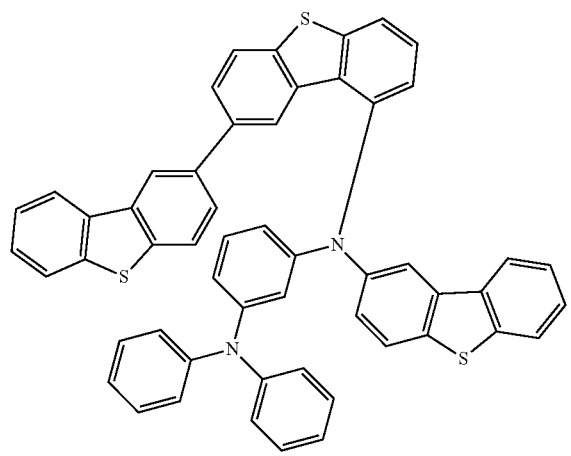
P-38
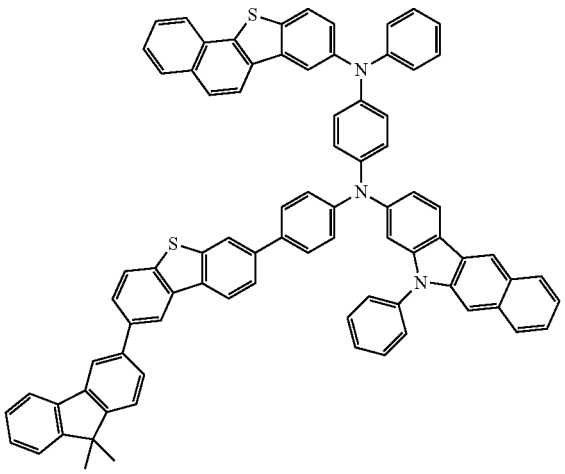
P-39
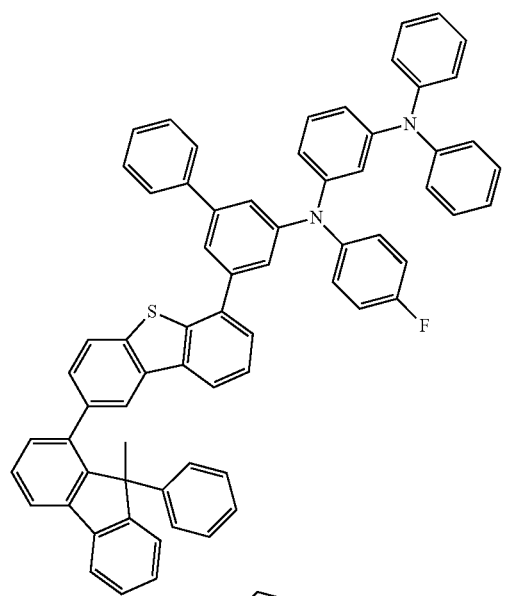
P-40
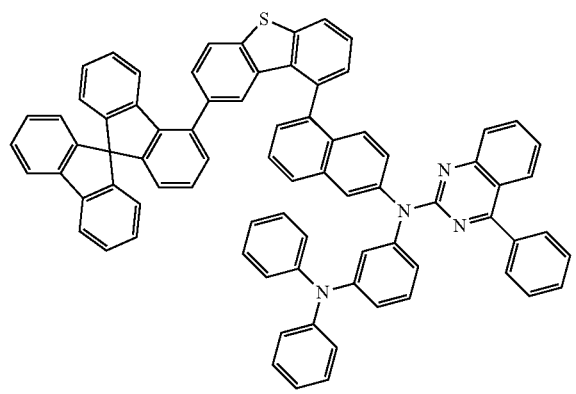
P-41
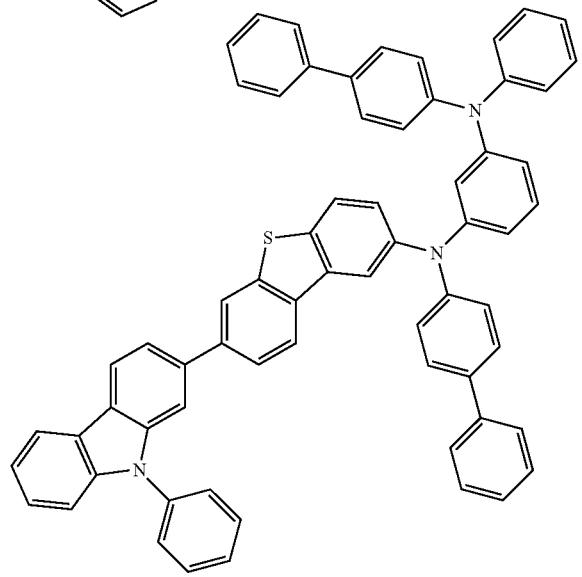
P-42
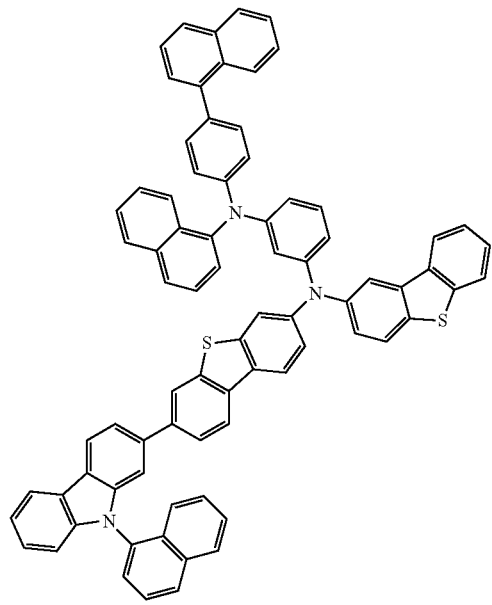

P-43
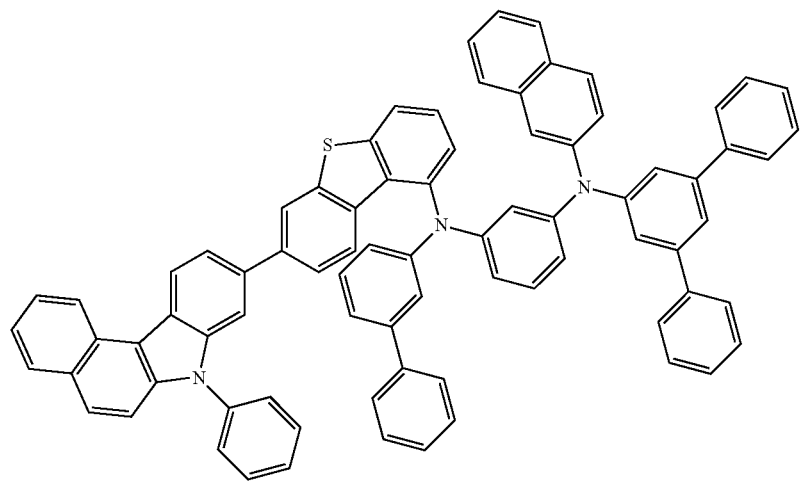
P-44
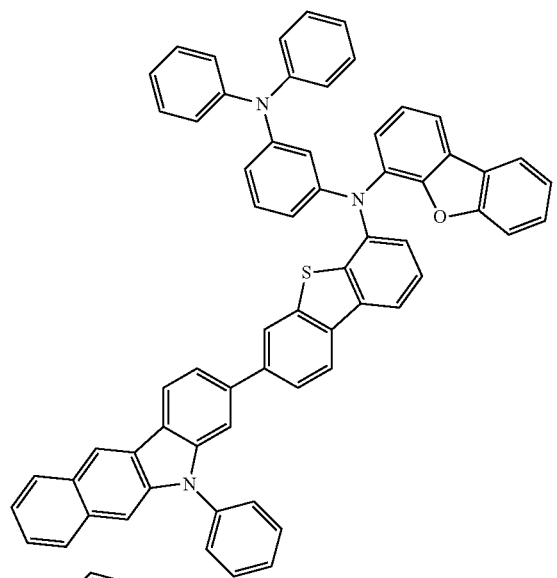
P-45
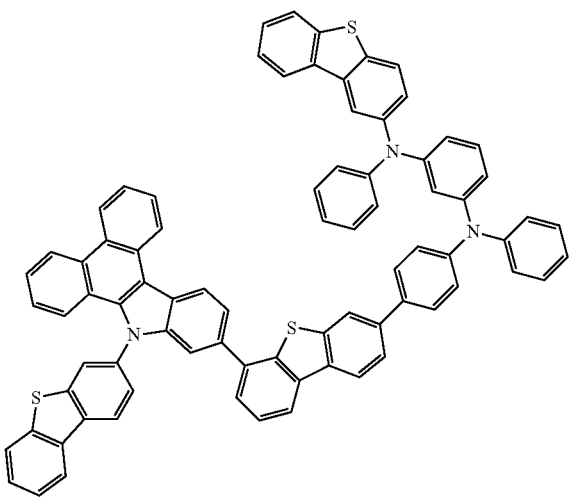
P-46
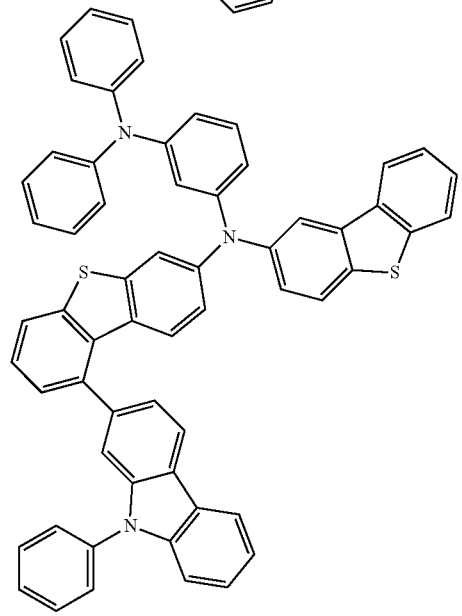
P-47
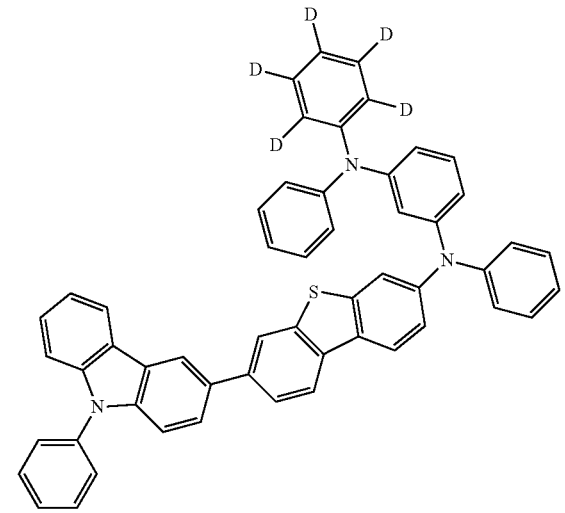

P-48
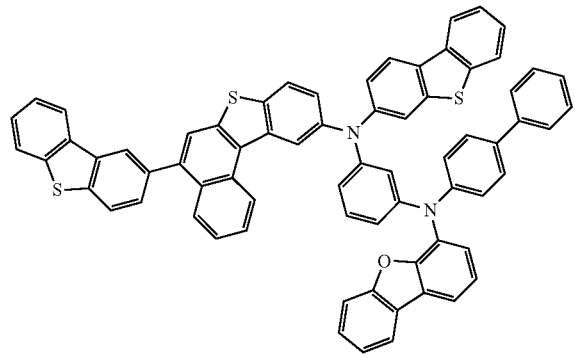
P-49
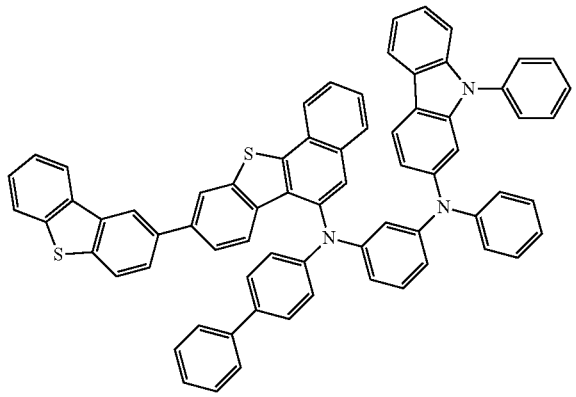
P-50
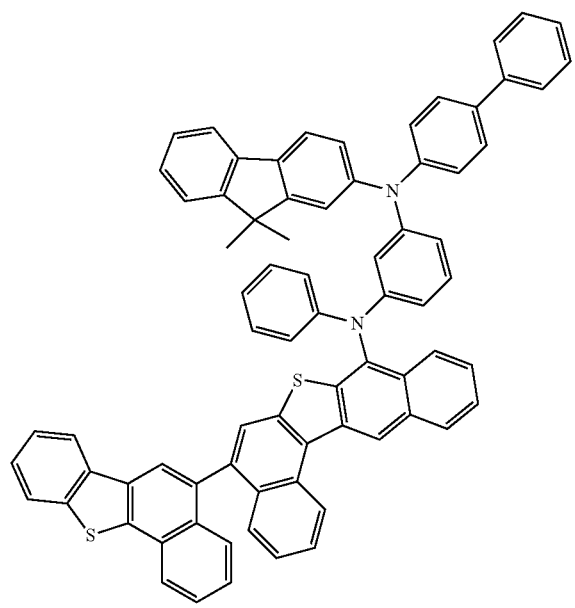
P-51
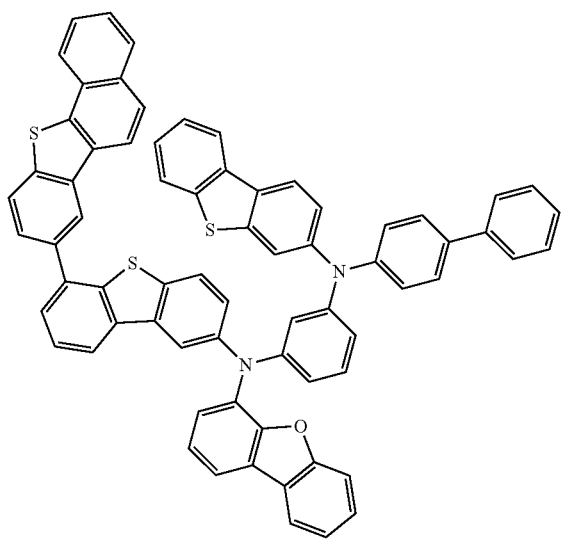
P-52
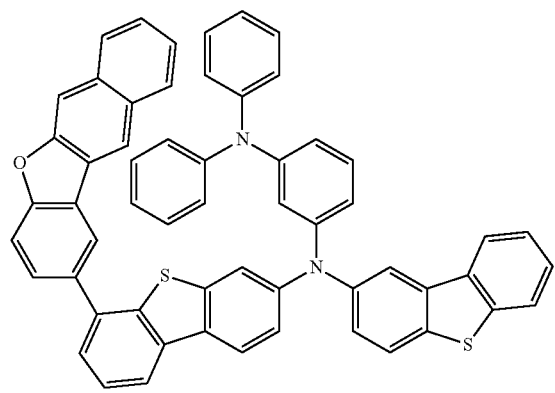

-continued
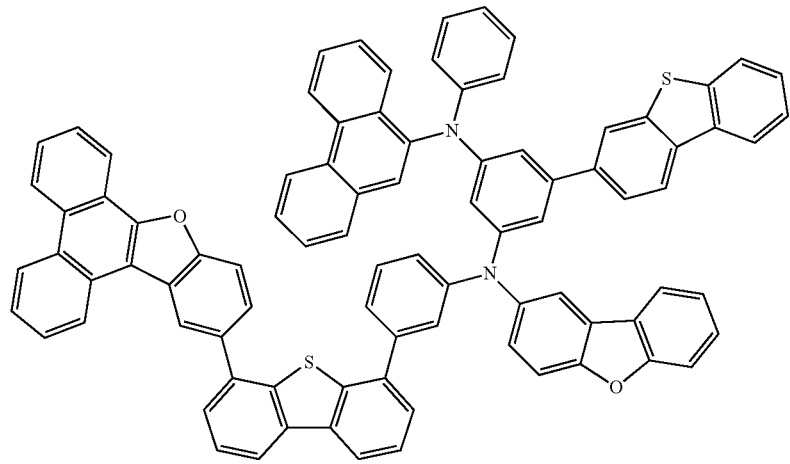
P-53
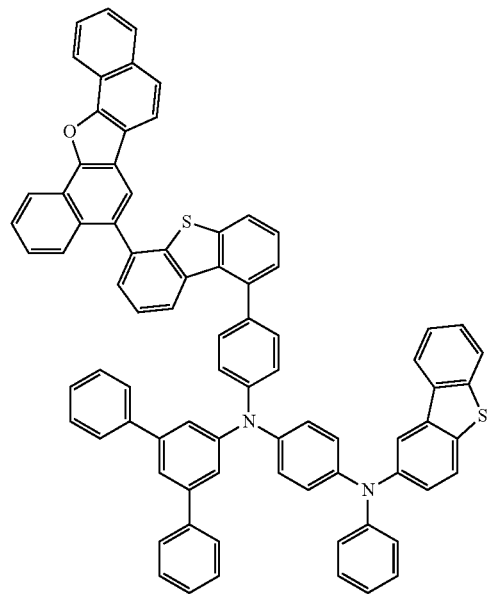
P-54
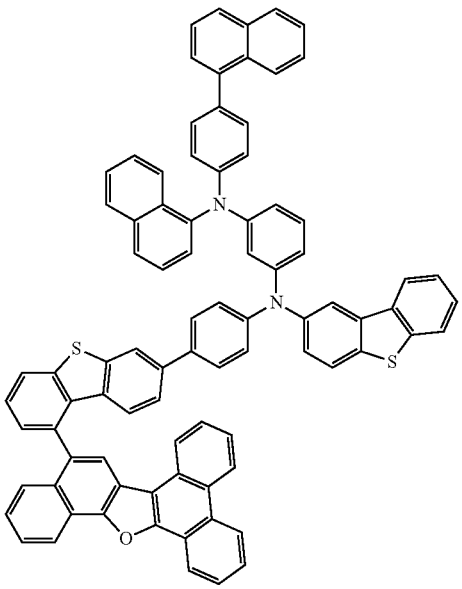
P-55
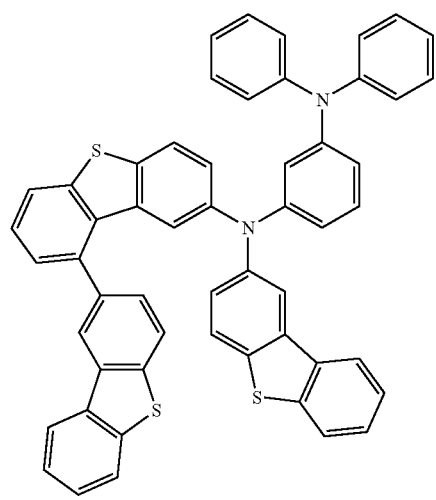
P-56
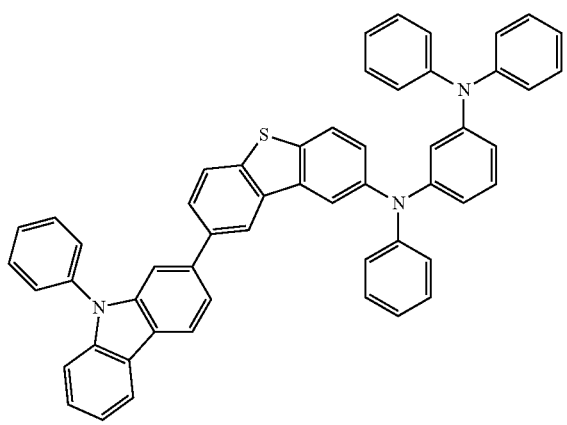
P-57

-continued
P-58
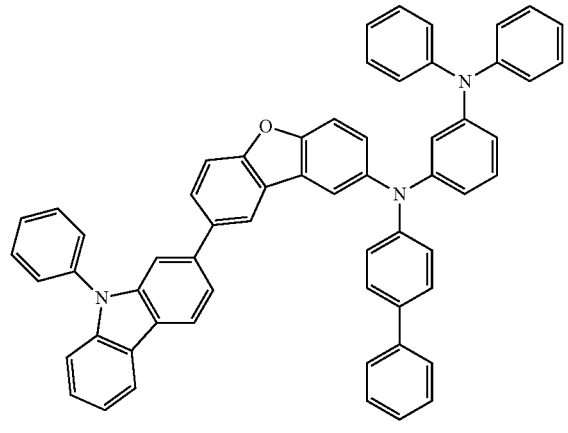
P-59
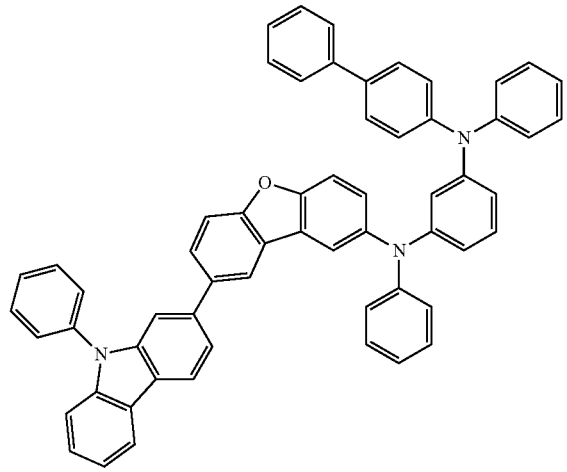
P-60
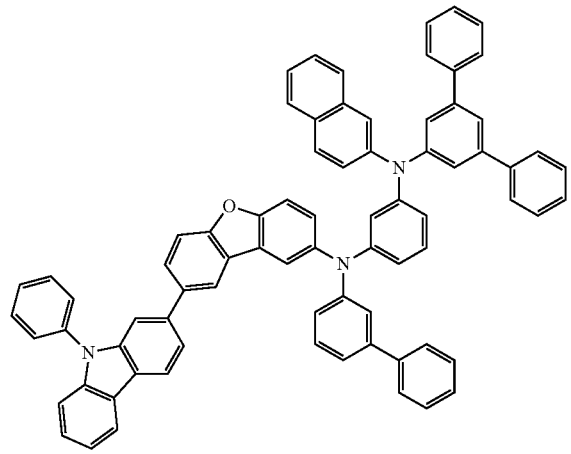
P-61
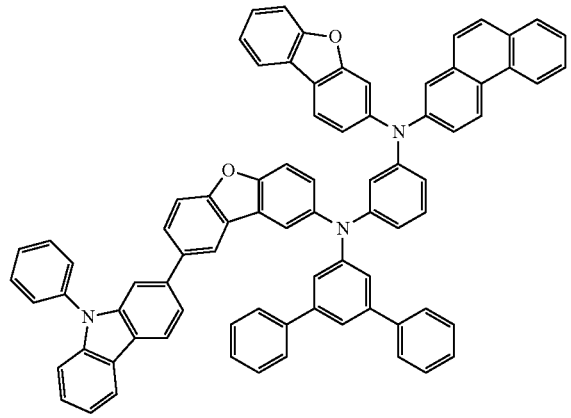
P-62
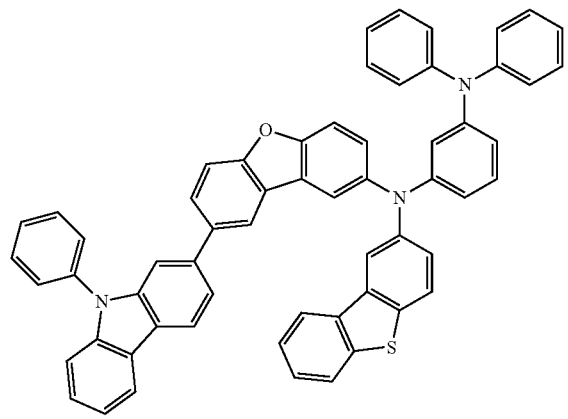
P-63
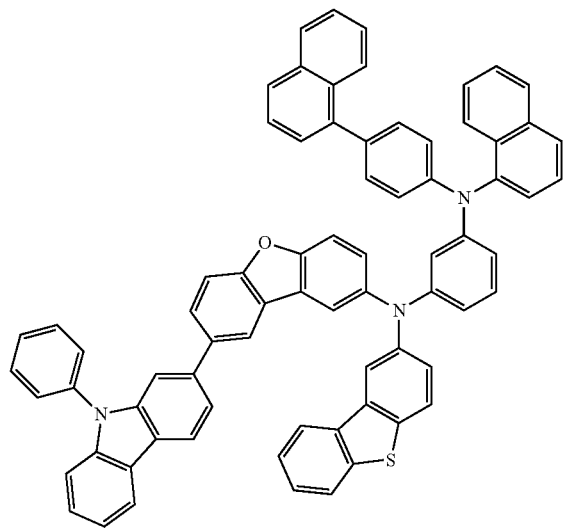

-continued
P-64
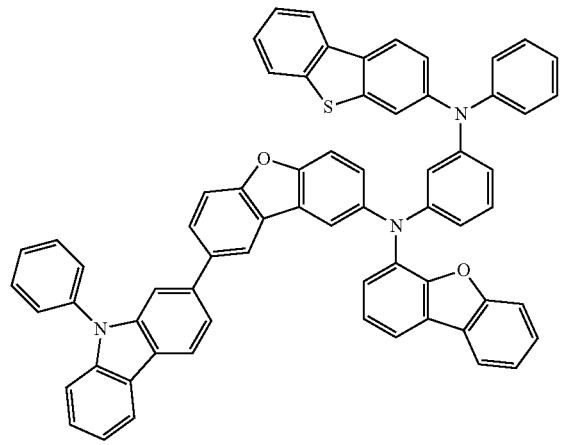
P-65
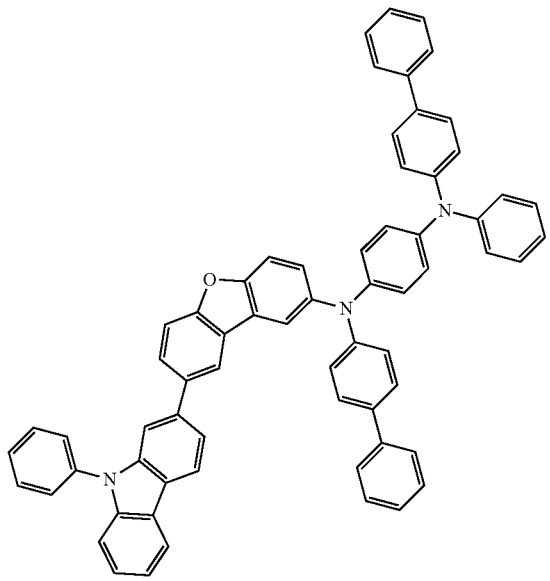
P-66
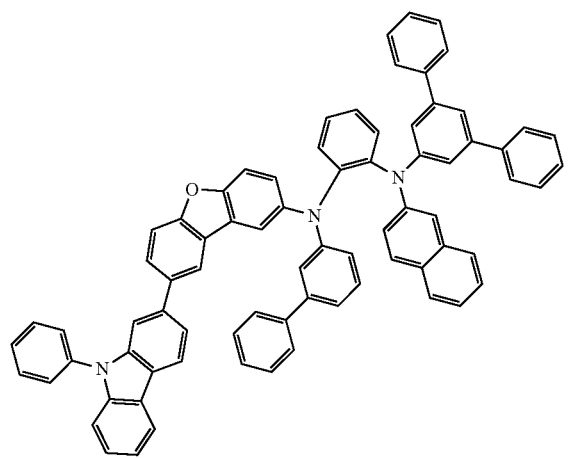
P-67
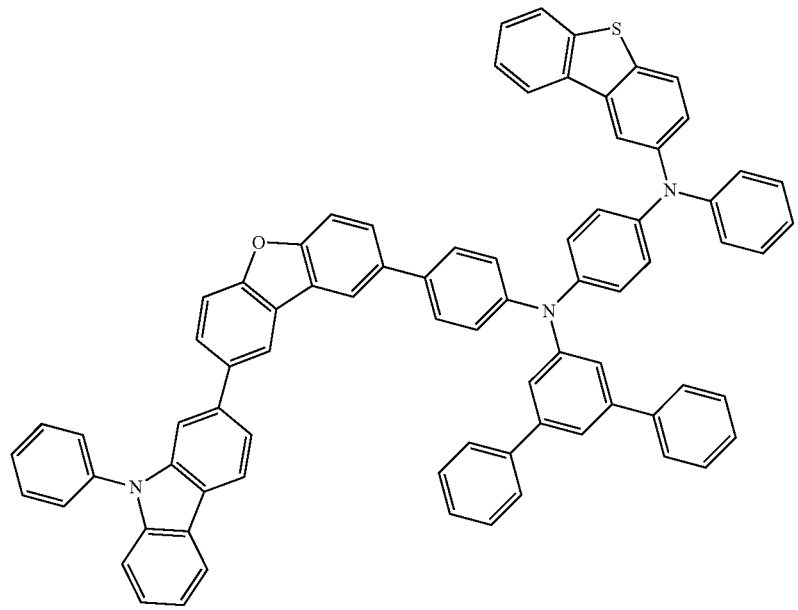

-continued
P-68
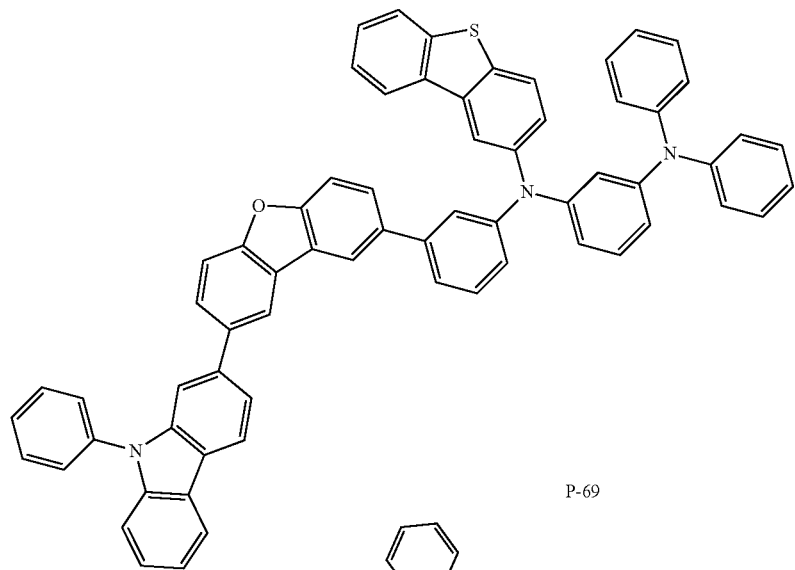
P-69
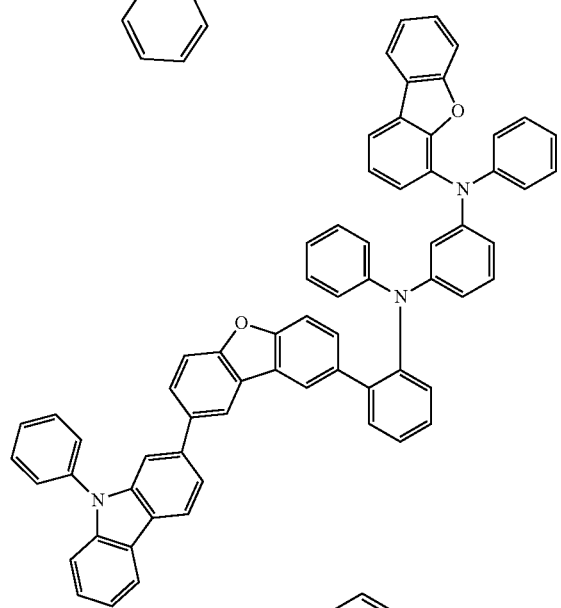
P-70
P-71
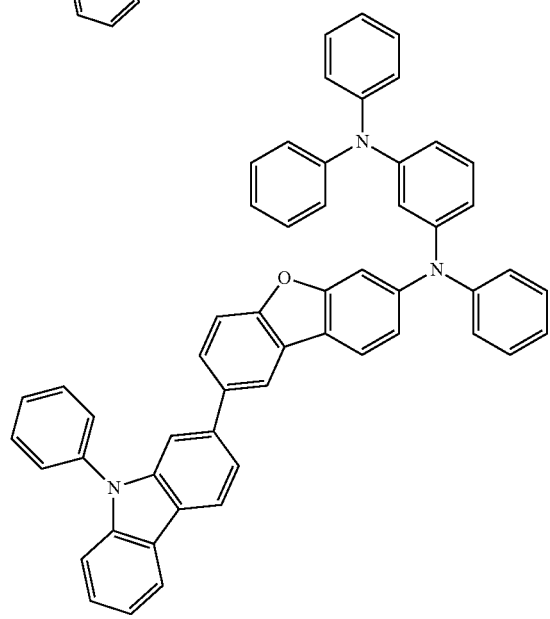
P-72

P-73
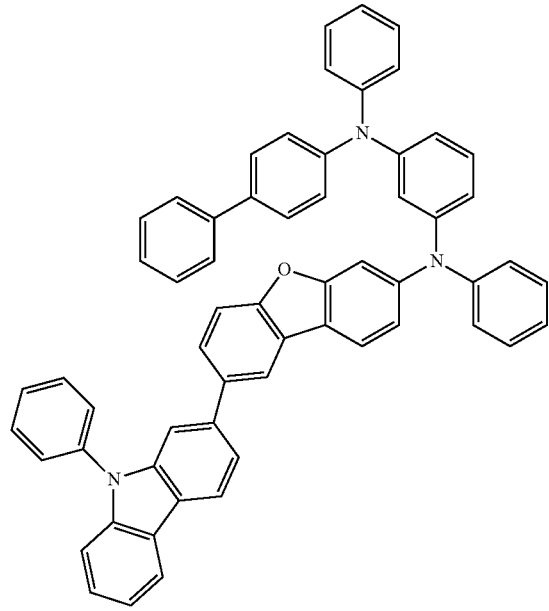
P-74
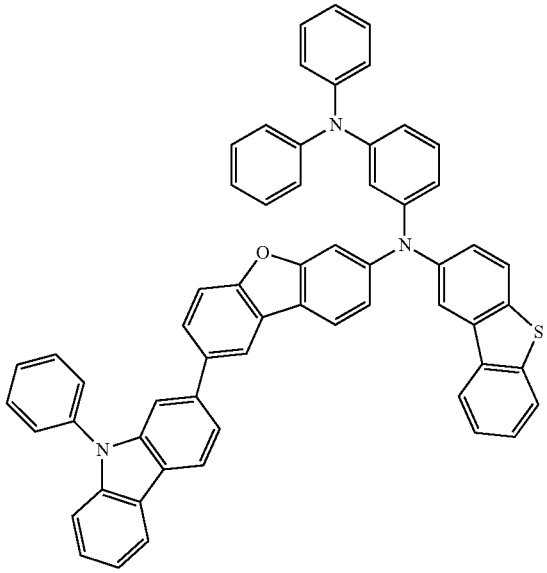
P-75
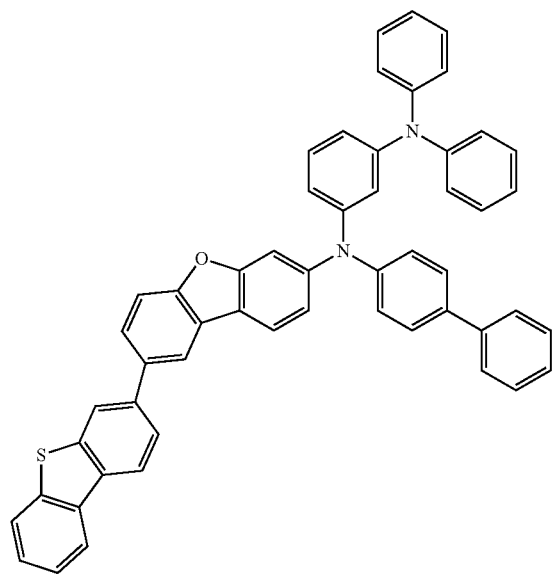
P-76
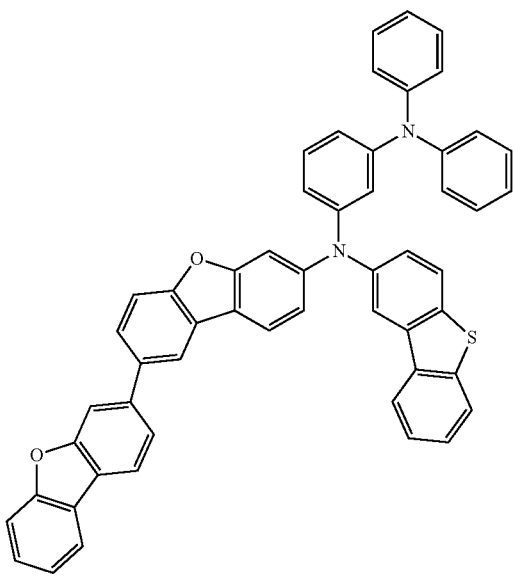

P-77
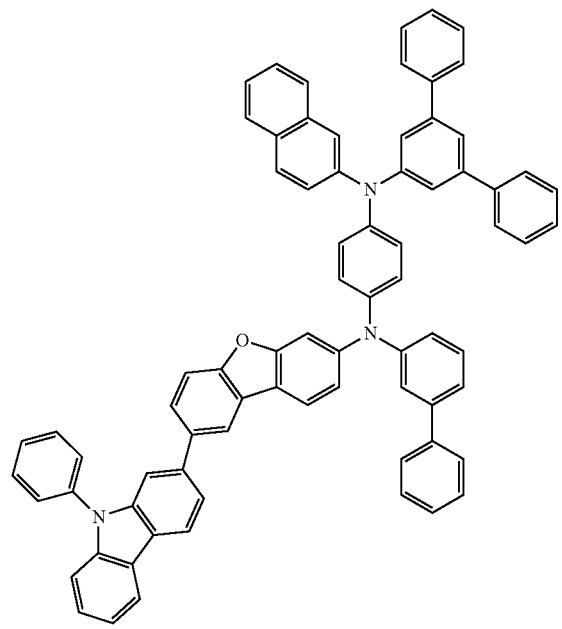
P-78
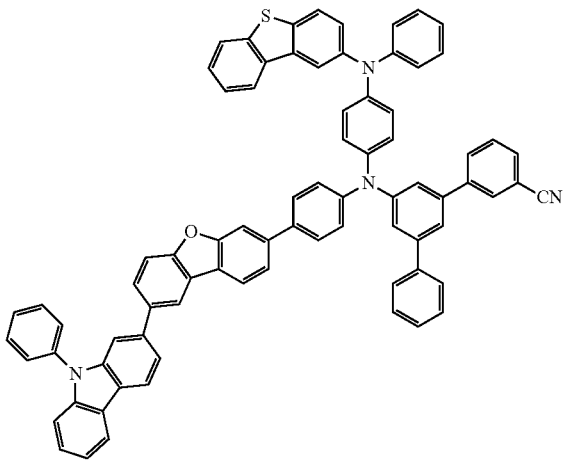
P-79
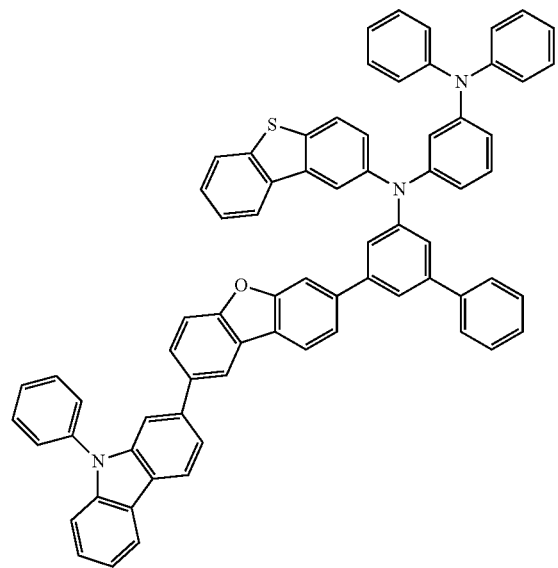
P-80
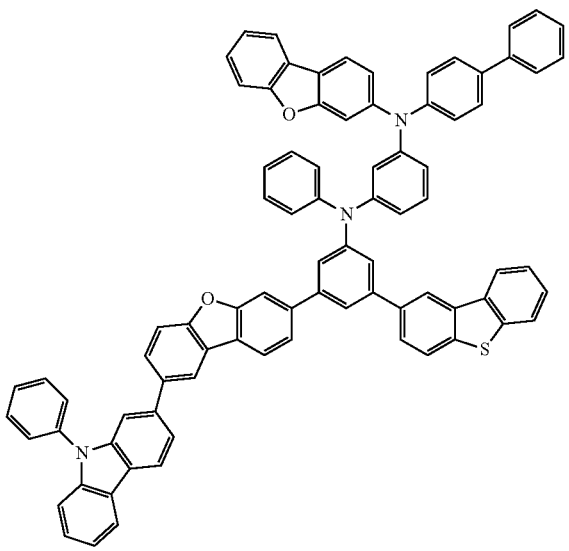

-continued
P-81
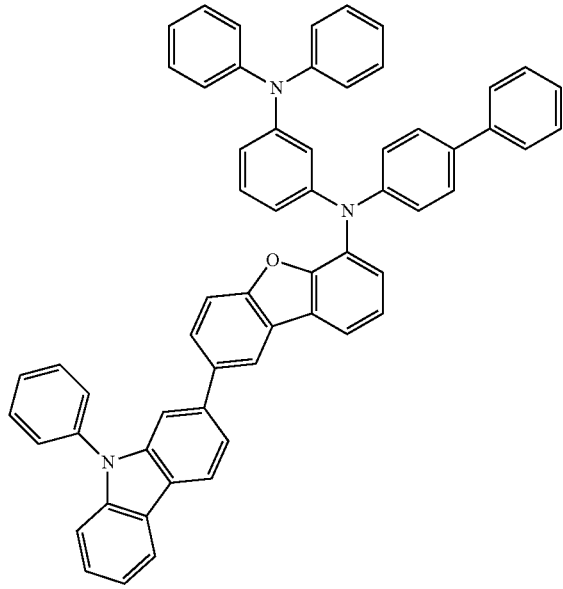
P-82
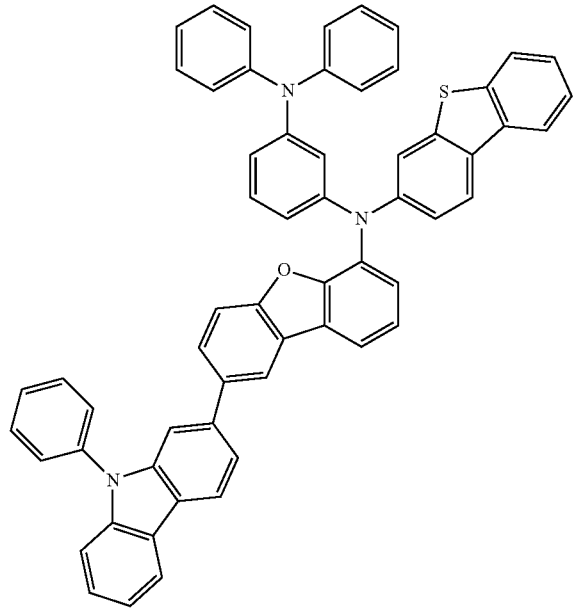
P-83
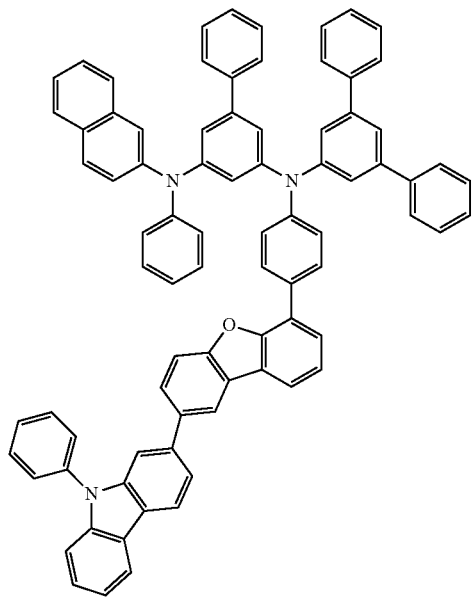
P-84
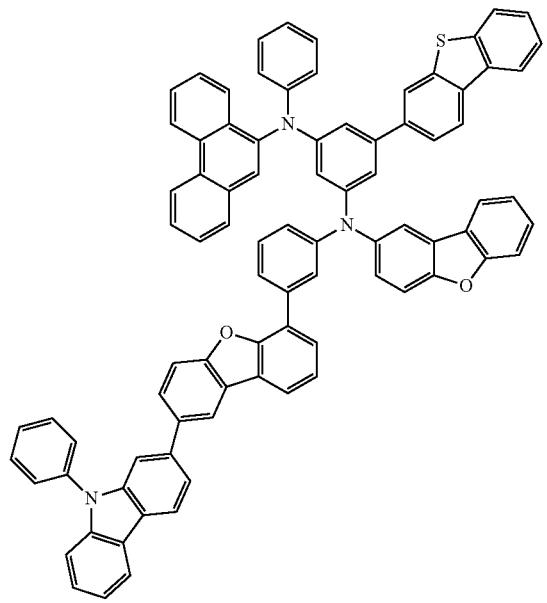
P-85
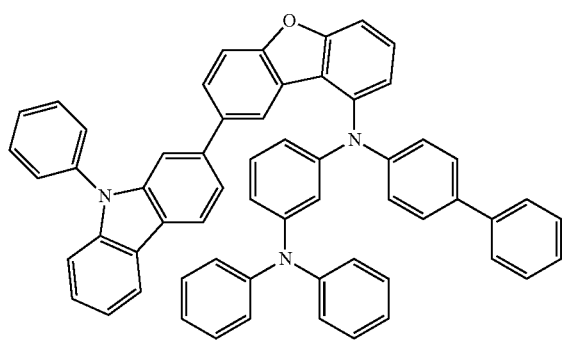
P-86
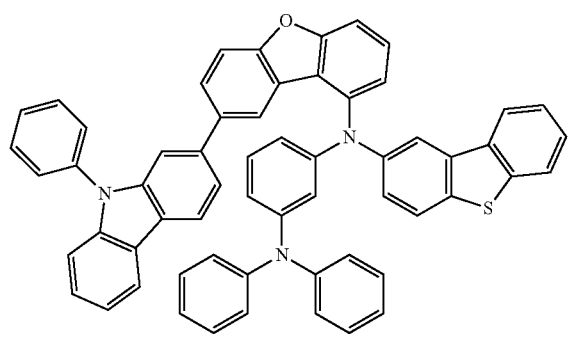

-continued
P-87
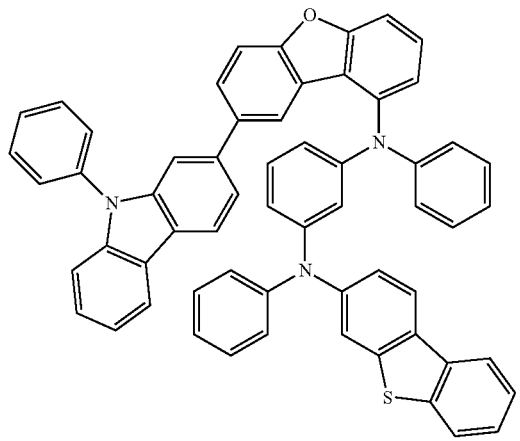
P-88
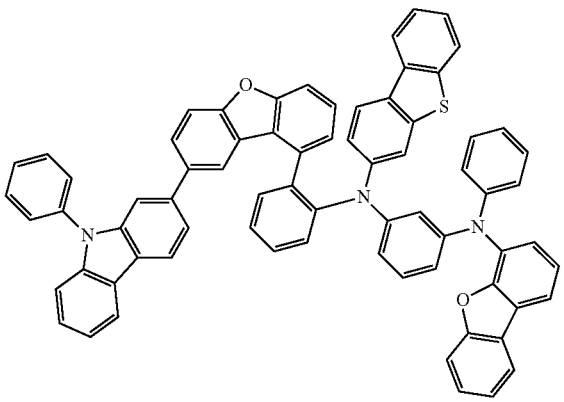
P-89
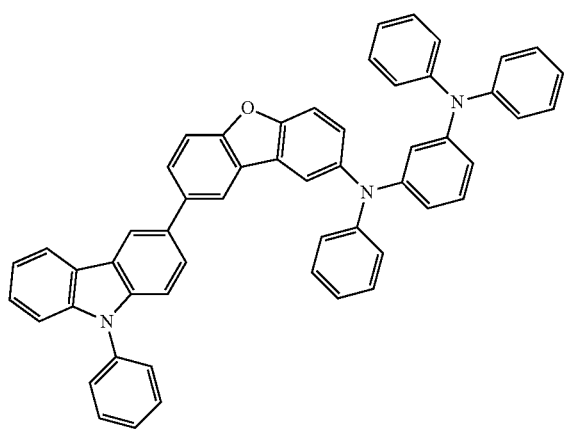
P-90
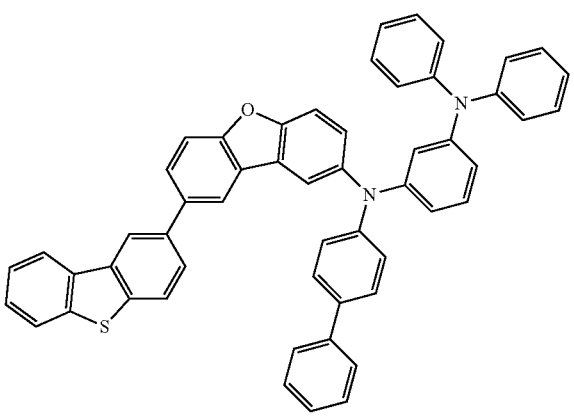
P-91
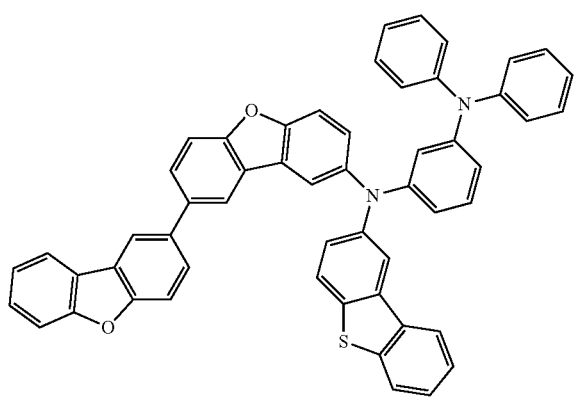
P-92
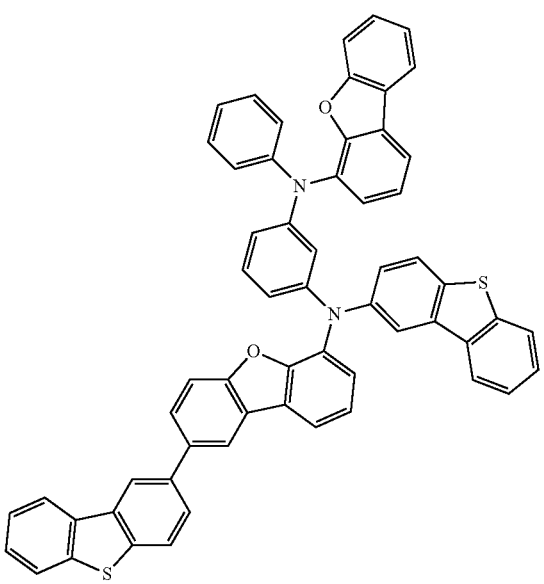

-continued
P-93
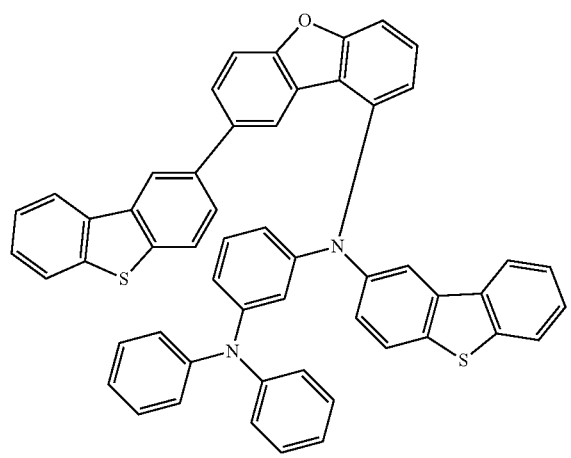
P-94
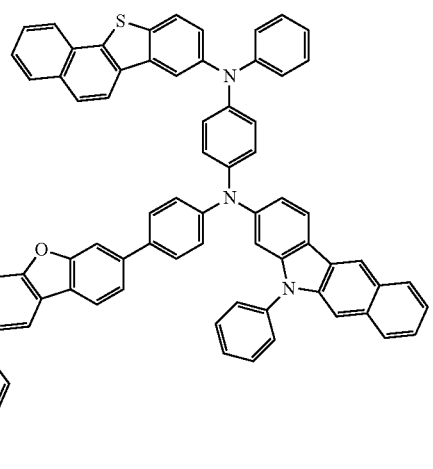
P-95
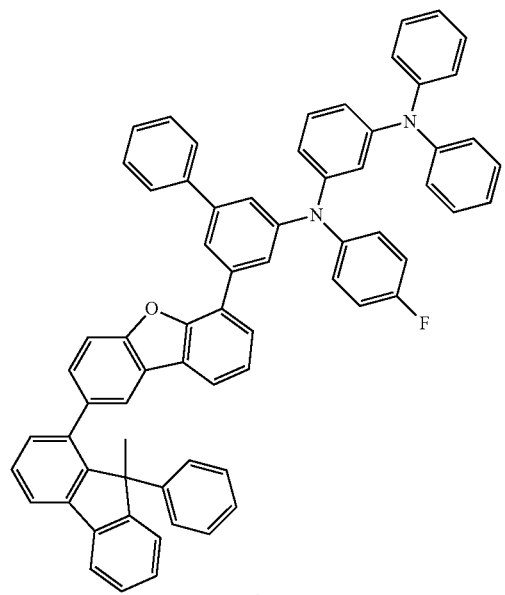
P-96
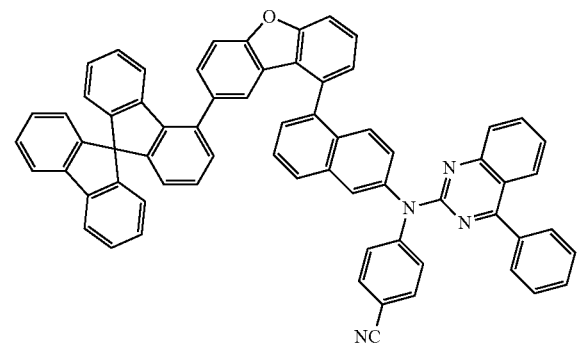
P-97
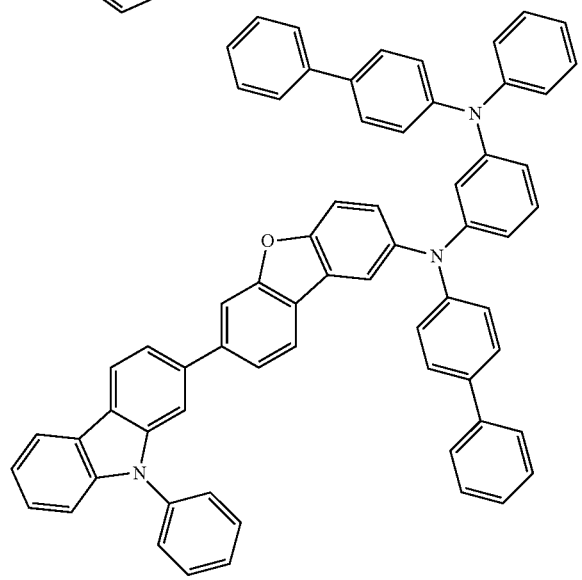
P-98
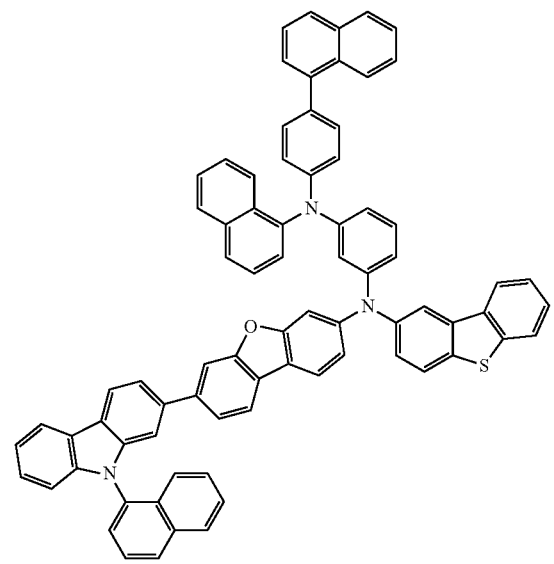

-continued
P-99
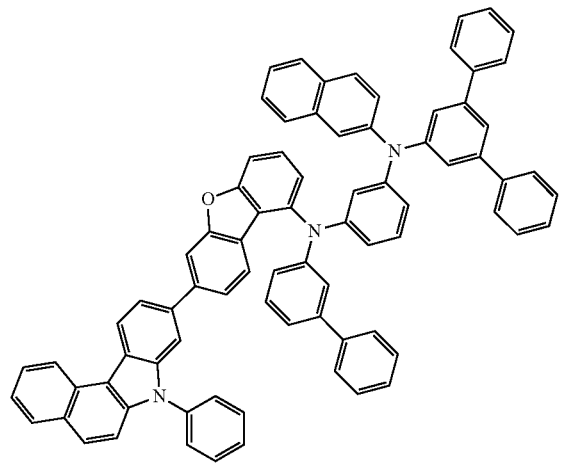
P-100
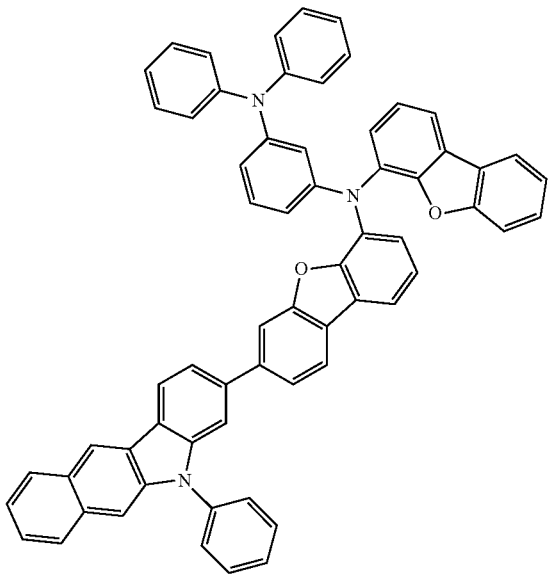
P-101
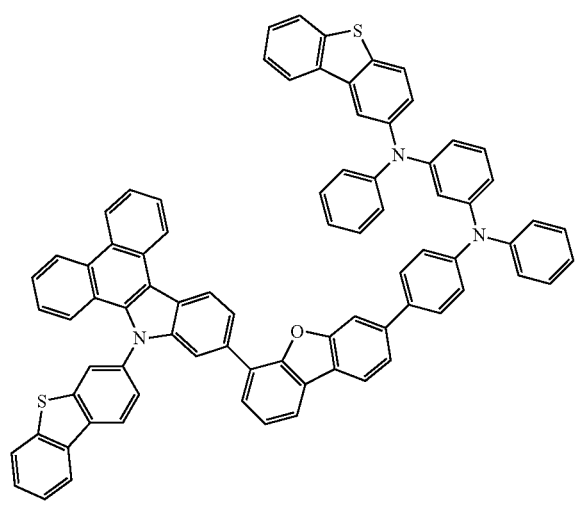
P-102
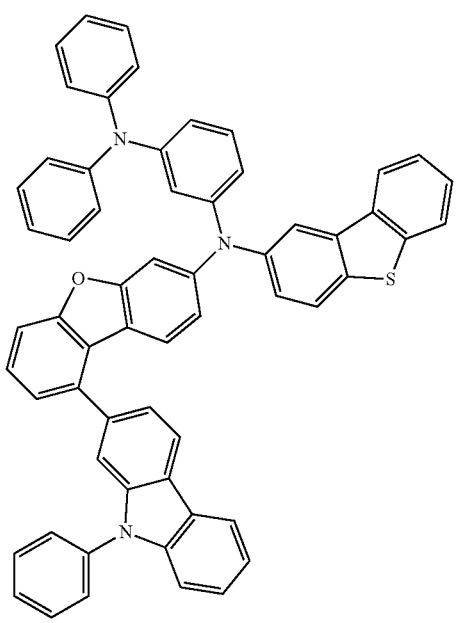

-continued
P-103
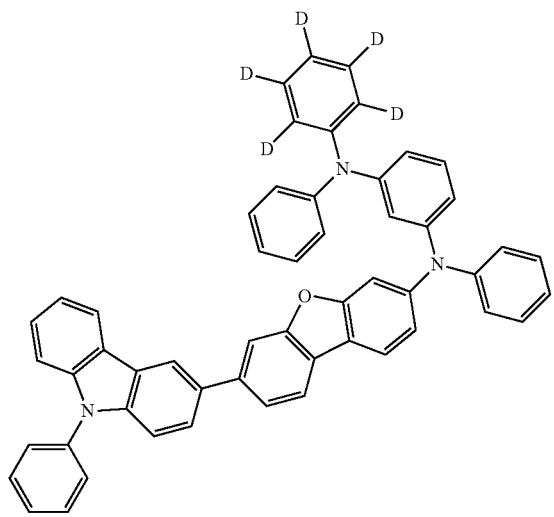
P-104
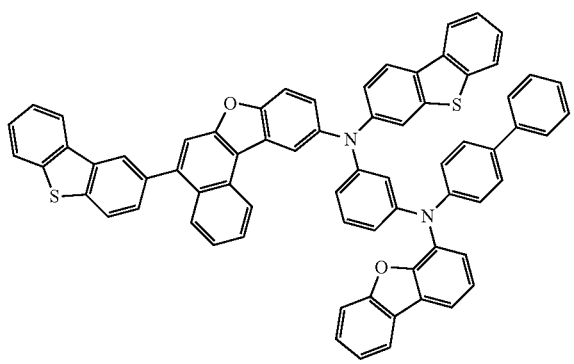
P-105
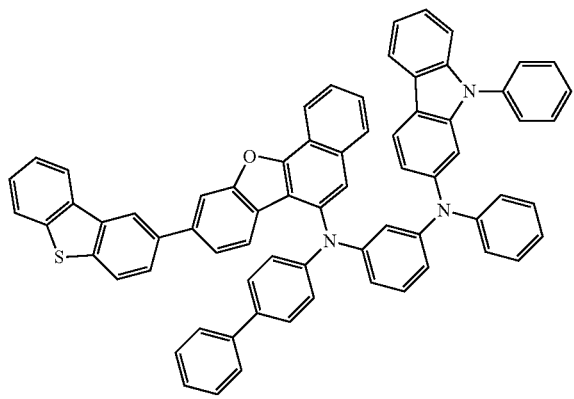
P-106
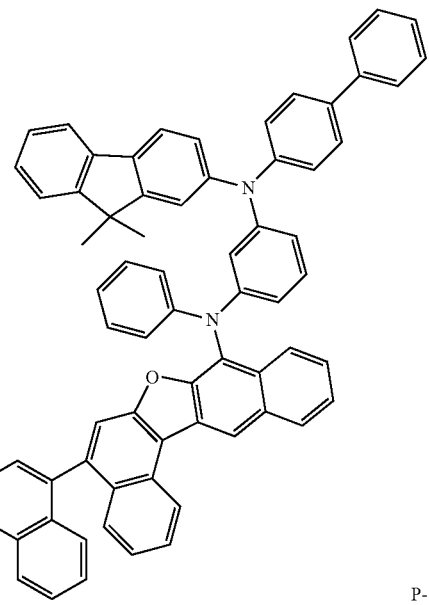
P-107
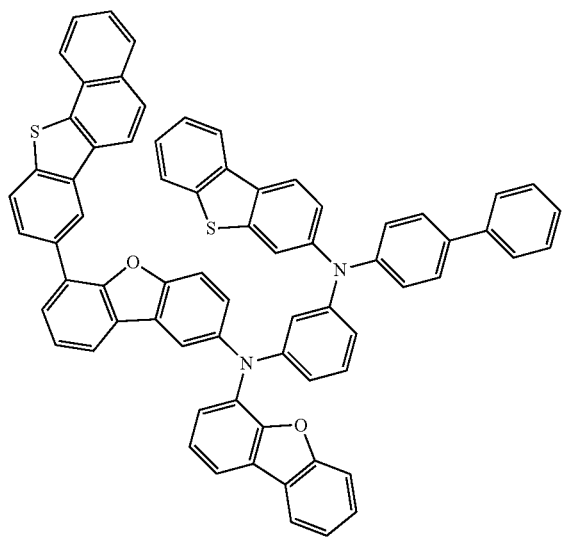
P-108
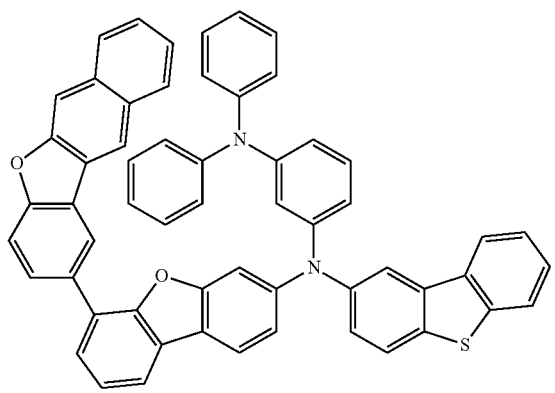

-continued
P-109
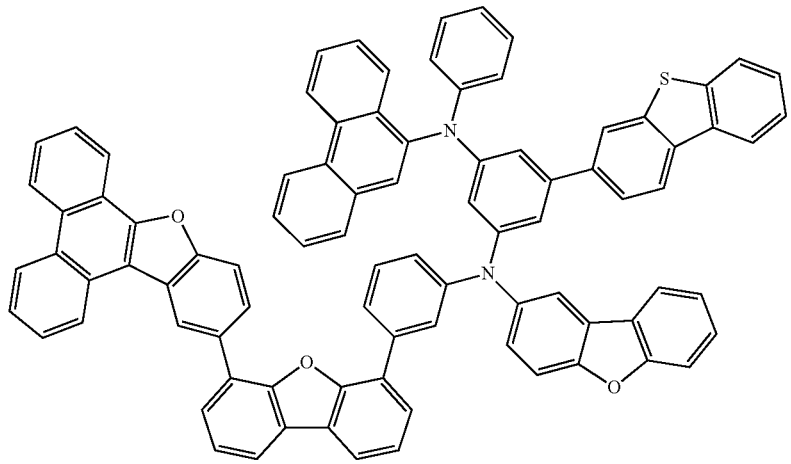
P-110
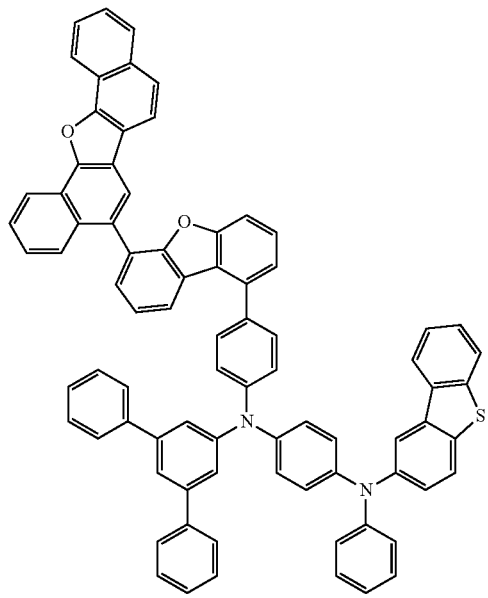
P-111
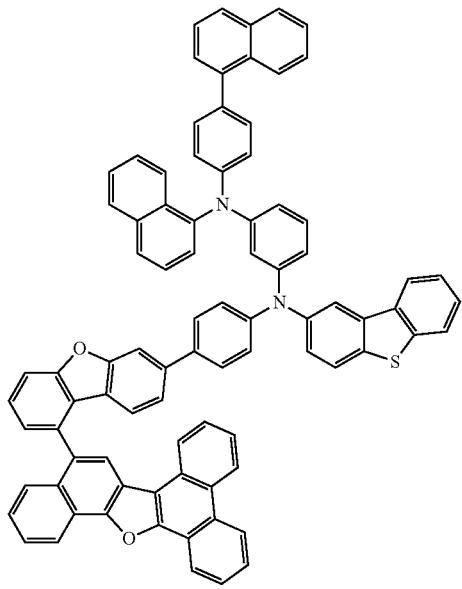
P-112
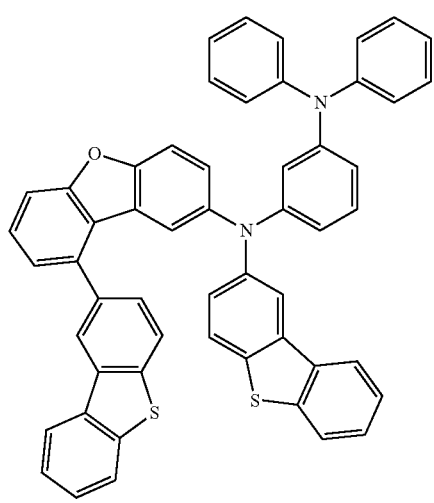
P-113
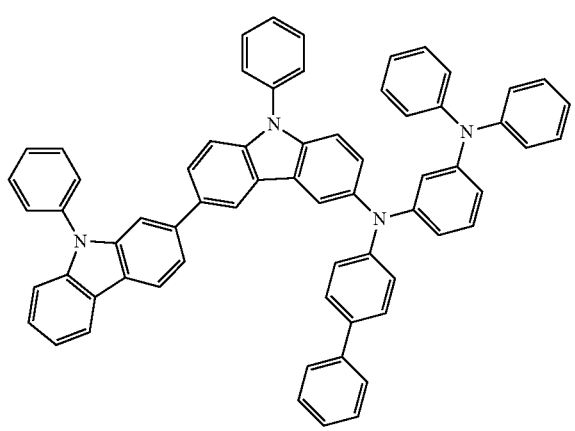

-continued
P-114
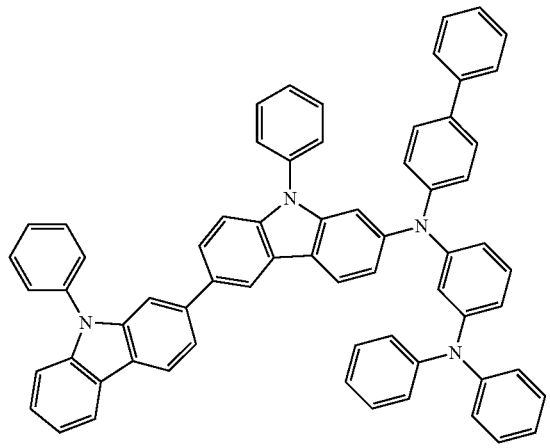
P-115
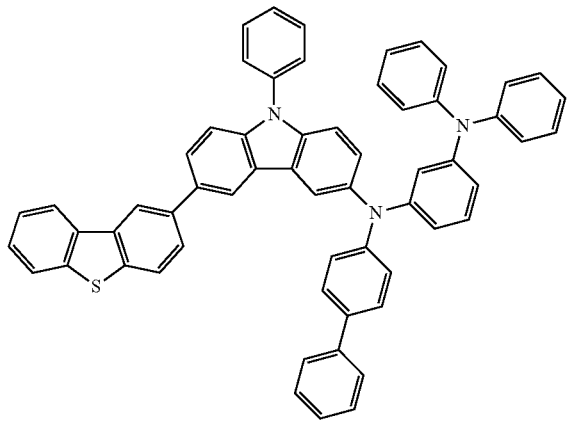
P-116
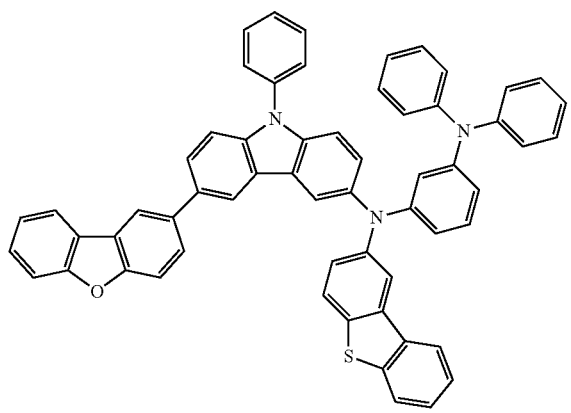
P-117
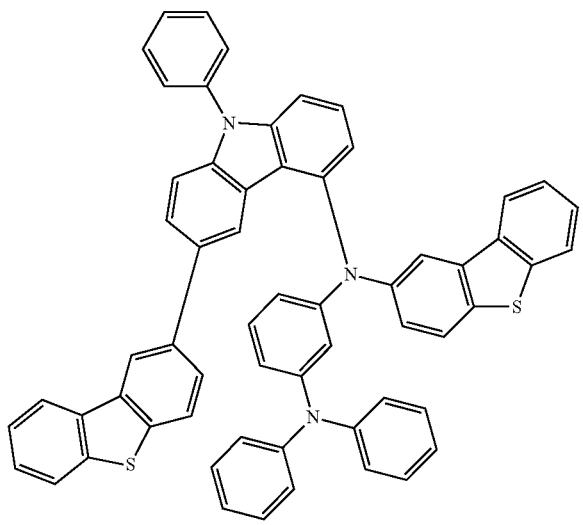
P-118
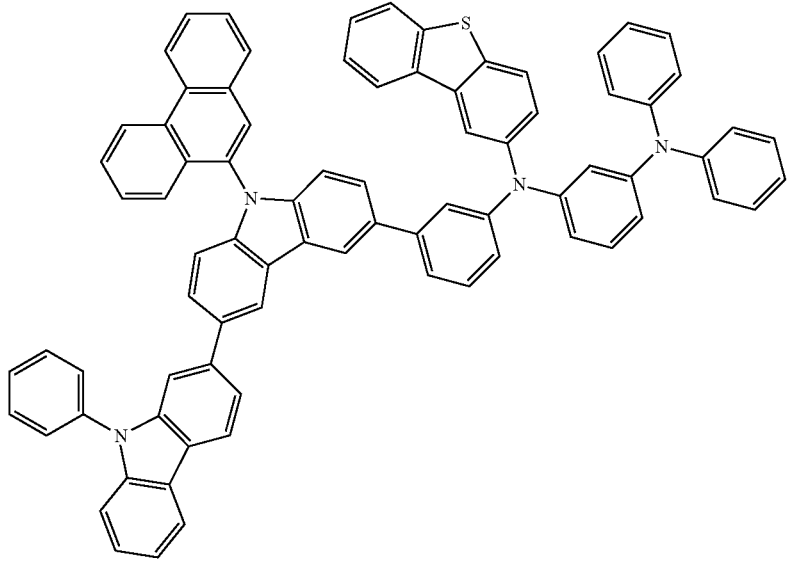

-continued
P-119
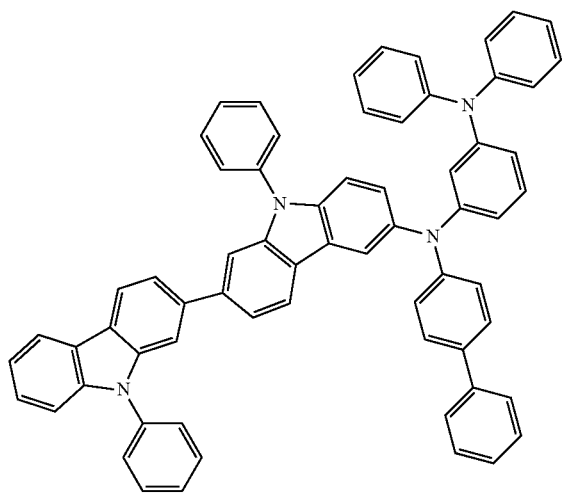
P-120
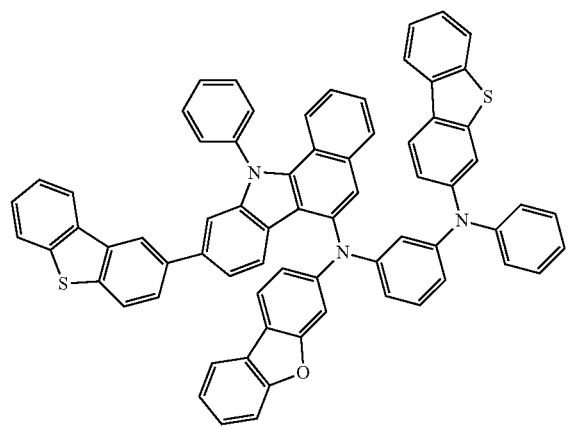
P-121
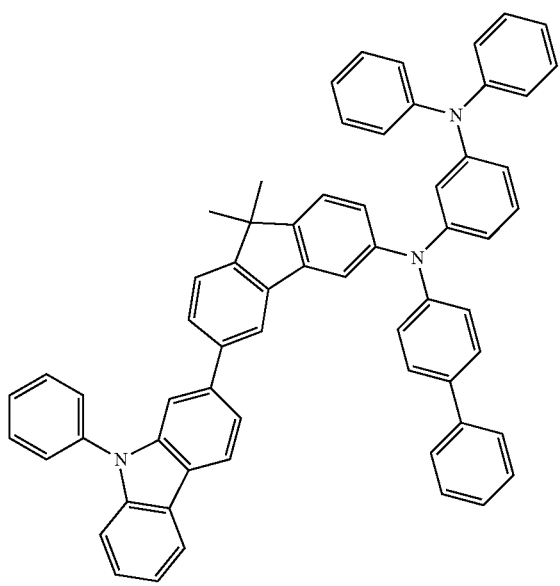
P-122
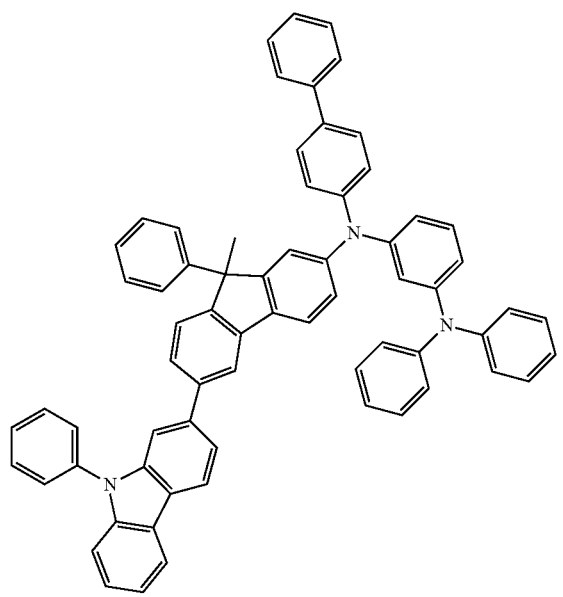
P-123
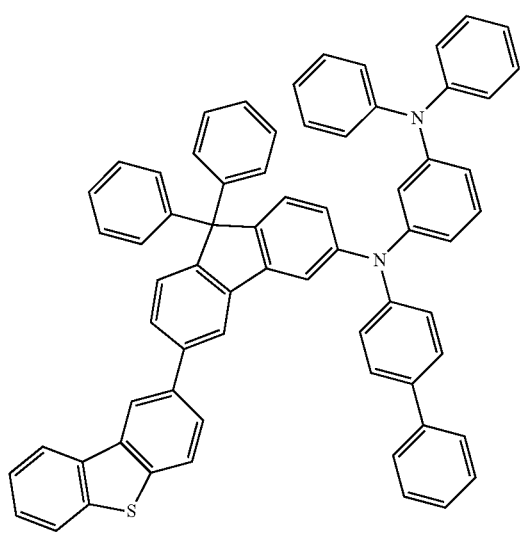
P-124
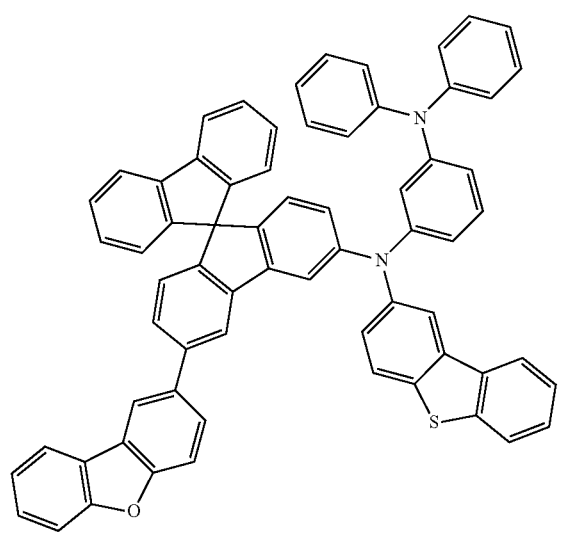

P-125

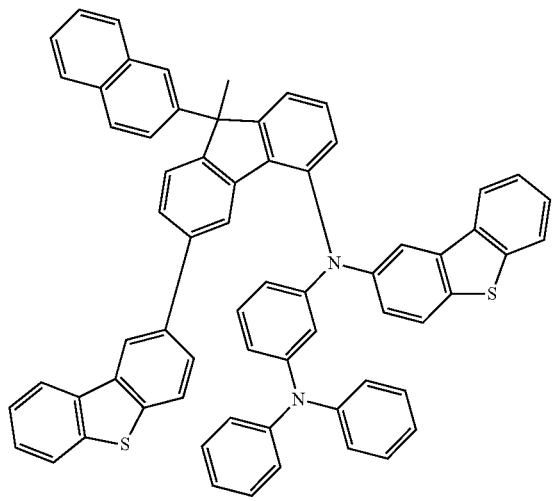

P-126

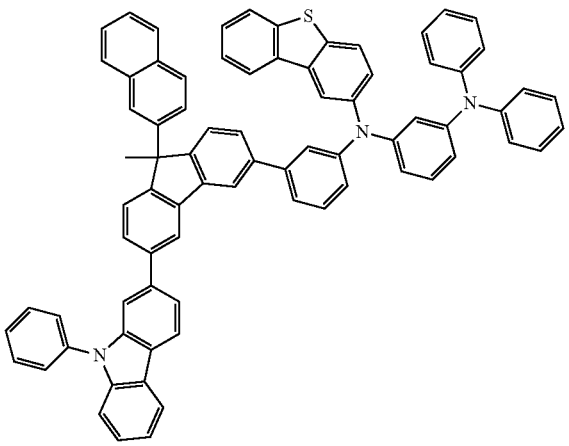

P-127

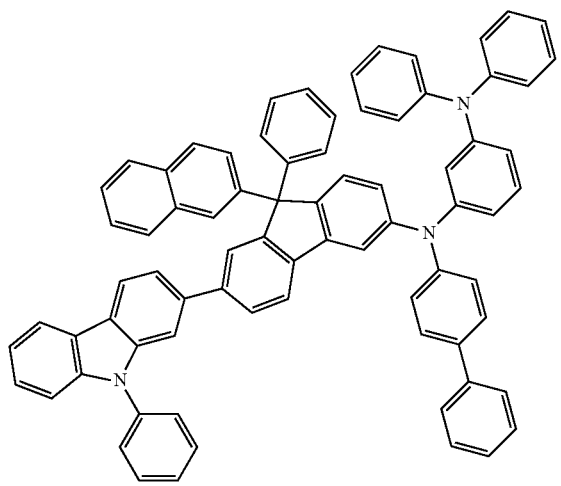

P-128

Referring to the FIGURE, the organic electric element (100) according to the present invention comprises a first electrode (120) formed on a substrate (110), a second electrode (180), and an organic material layer including the compound represented by Formula (1) between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may comprise a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further comprise a hole blocking layer, an electron blocking layer, an emitting-auxiliary layer (151), an electron transport layer, an electron transport auxiliary layer, a buffer layer (141), etc., and the electron transport layer (160) and the like may serve as a hole blocking layer.

Although not shown, the organic electric element according to the present invention may further comprise a protective layer formed on at least one surface of the first electrode and the second electrode opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emitting-auxiliary layer (151) may be further formed between the hole transport layer (140) and the emitting layer (150), and an electron transport auxiliary layer may be further formed between the emitting layer (150) and the electron transport layer (160).

The present invention may further comprise a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

In addition, the present invention provides a compound, wherein at least one of the hole injection layer, the hole transport layer, the emitting-auxiliary layer, and the emitting layer includes a compound according to Formula (1), wherein the compound provides an organic electric element comprising a composition in which one or 2 or more compounds are mixed.

As another specific example, the present invention provides an organic electric element characterized in that the organic layer is mixed with the same or different compound of the compound represented by Formula (1).

The present invention also provides an organic electric element comprising a hole transport layer containing a compound represented by Formula (1) and a emitting-auxiliary layer, and in another aspect, an organic electric element comprising a hole transport layer or an emitting-auxiliary layer containing a compound represented by Formula (1).

Also, the present invention provides an organic electric element wherein the hole transport layer or the emitting-auxiliary layer contains one or more of the above compounds.

The organic electric element according to an embodiment of the present invention may be a front emission type, a back emission type, or a both-sided emission type, depending on the material used.

WOLED (White Organic Light Emitting Device) is easy to realize high resolution and has excellent fairness, and can be manufactured using the color filter technology of the conventional LCD. Various structures for a white organic light emitting device mainly used as a backlight device have been proposed and patented. Representatively, there are side-by-side arrangement of the radiation part of the red (R), green (G) and blue (B), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, synthesis examples of the compound represented by Formula (1) according to the present invention and preparation examples of the organic electric element will be described in detail by way of example, but are not limited to the following examples of the invention.

Synthesis Example 1

The final products 1 represented by Formula (1) of the present invention can be synthesized by reaction between Sub 1 and Sub 2 as illustrated in the following Reaction Scheme 1.

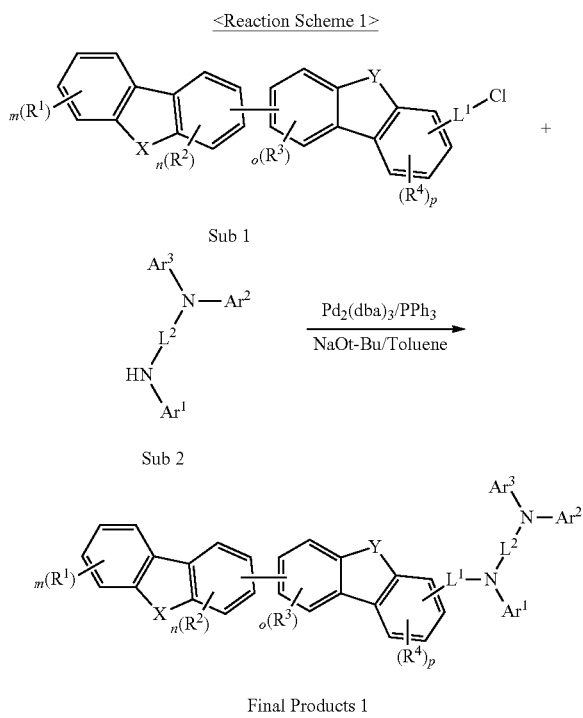

Synthesis Examples of Sub 1

Sub 1 of Reaction Scheme 1 can be synthesized by the reaction path of the following Reaction Scheme 2, but is not limited thereto.

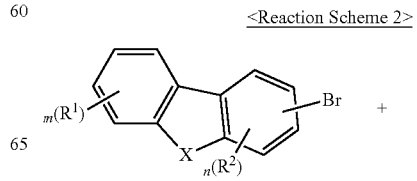

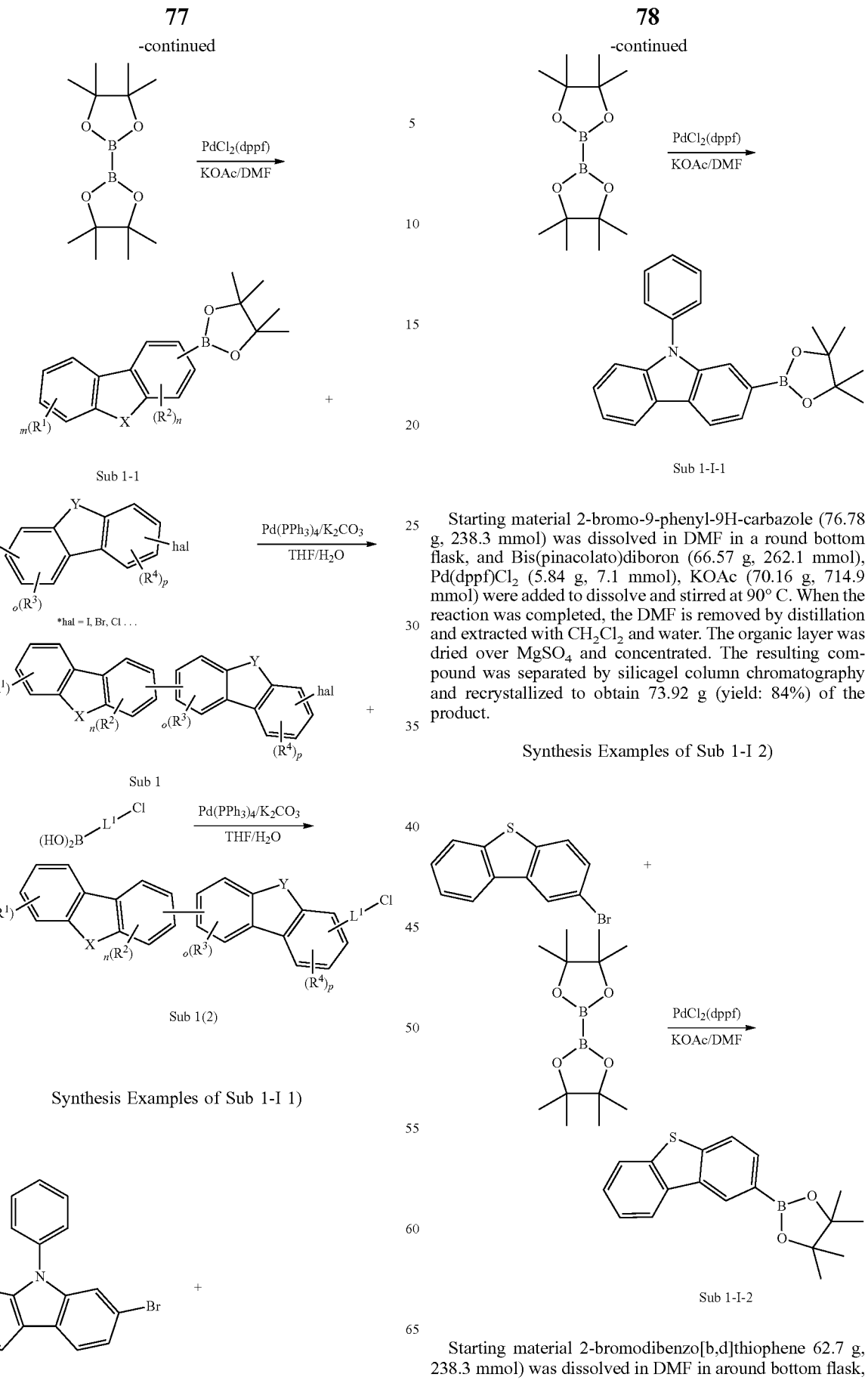

Starting material 2-bromo-9-phenyl-9H-carbazole (76.78 g, 238.3 mmol) was dissolved in DMF in a round bottom flask, and Bis(pinacolato)diboron (66.57 g, 262.1 mmol), Pd(dppf)Cl$_2$ (5.84 g, 7.1 mmol), KOAc (70.16 g, 714.9 mmol) were added to dissolve and stirred at 90° C. When the reaction was completed, the DMF is removed by distillation and extracted with CH$_2$Cl$_2$ and water. The organic layer was dried over MgSO$_4$ and concentrated. The resulting compound was separated by silicagel column chromatography and recrystallized to obtain 73.92 g (yield: 84%) of the product.

Synthesis Examples of Sub 1-I 2)

Starting material 2-bromodibenzo[b,d]thiophene 62.7 g, 238.3 mmol) was dissolved in DMF in around bottom flask, Synthesis Examples of Sub 1(1) 1)

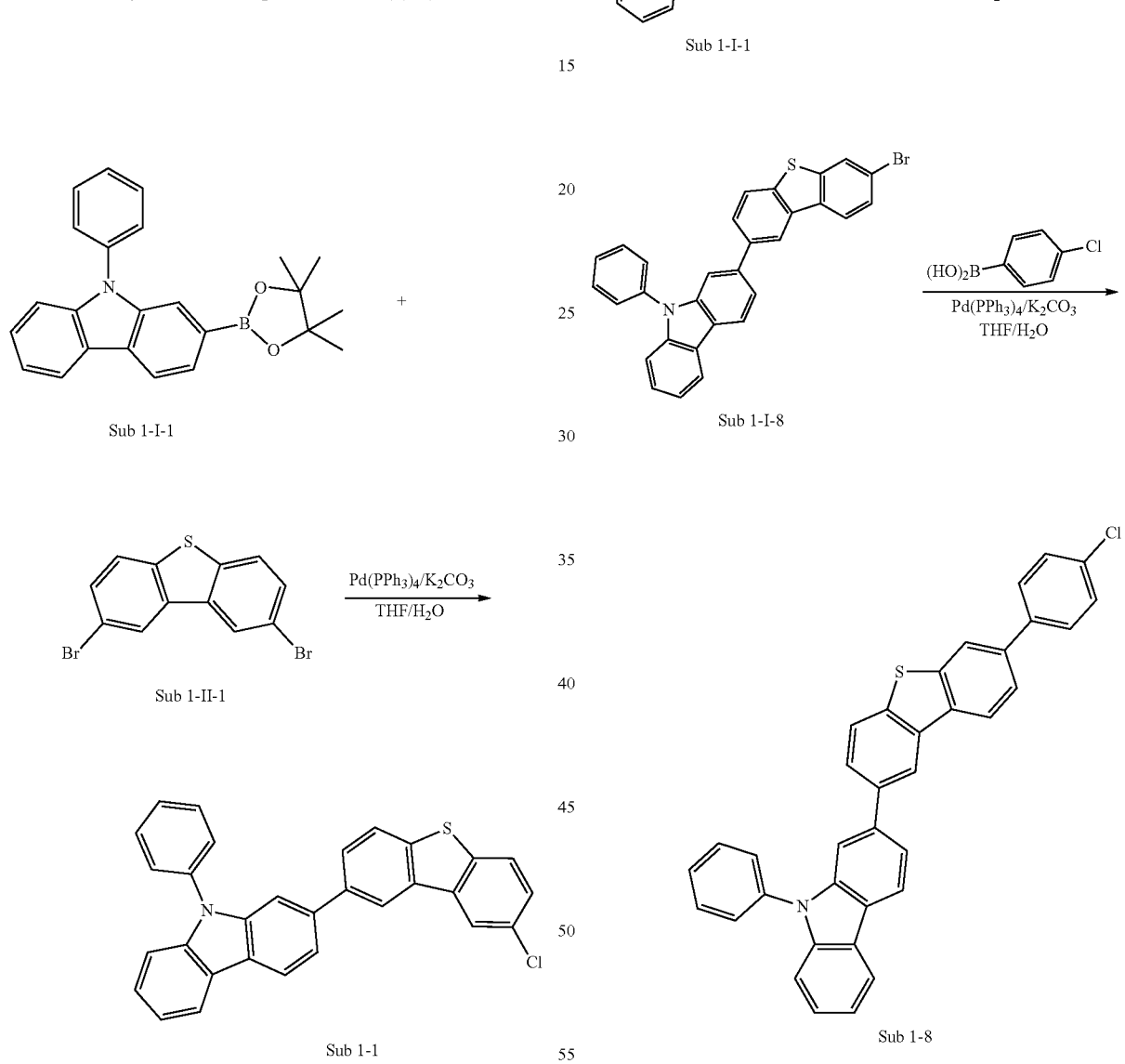

Sub 1-I-1 (73.92 g, 200.2 mmol) was dissolved in THE 880 ml in a round bottom flask, and Sub 1-II-1 (89.36 g, 300.3 mmol), Pd(PPh$_3$)$_4$ (11.6 g, 10 mmol), K$_2$CO$_3$ (83 g, 600.6 mmol) and water (440 mL) were added and stirred at 80° C. When the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 59.2 g (yield: 75%) of the product.

and Bis(pinacolato)diboron (66.57 g, 262.1 mmol), Pd(dppf)Cl$_2$ (5.84 g, 7.1 mmol), KOAc (70.16 g, 714.9 mmol) were added to dissolve and stirred at 90° C. When the reaction was completed, the DMF is removed by distillation and extracted with CH$_2$Cl$_2$ and water. The organic layer was dried over MgSO$_4$ and concentrated. The resulting compound was separated by silicagel column chromatography and recrystallized to obtain 60.02 g (yield: 81%) of the product.

Synthesis Examples of Sub 1(2) 2)

(1) Synthesis of Sub 1-I-8

Sub 1-I-1 (62.7 g, 169.79 mmol) and Sub 1-II-2 (66.06 g, 169.79 mmol) were reacted using the synthesis method of Sub 1-1 described above to give 72.0 g of the product. (yield: 84%).

(2) Synthesis of Sub 1-8

Sub 1-I-8 (72.0 g, 142.73 mmol) and 4-chlorophenylboronic acid (22.3 g, 142.73 mmol) were reacted using the synthesis method of Sub 1-1 described above to give 55.6 g of the product. (yield: 72%).

Synthesis Examples of Sub 1(1) 3)

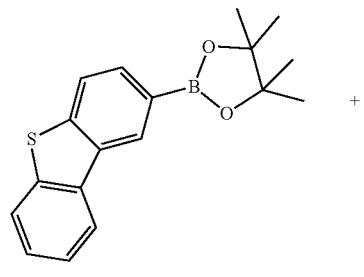
Sub 1-I-2

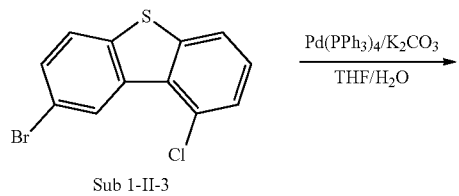
Sub 1-II-3

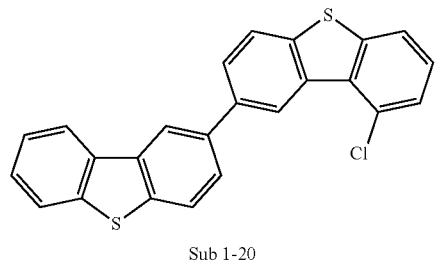
Sub 1-20

Sub 1-I-2 (50.0 g, 161.18 mmol) and Sub 1-II-3 (47.96 g, 161.18 mmol) were reacted using the synthesis method of Sub 1-1 described above to give 66.5 g of the product (yield: 77%).

Synthesis Examples of Sub 1(1) 4)

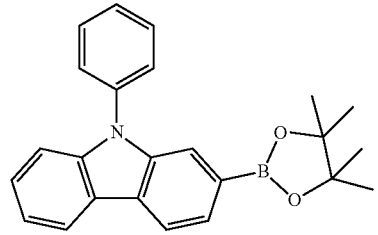
Sub 1-I-1

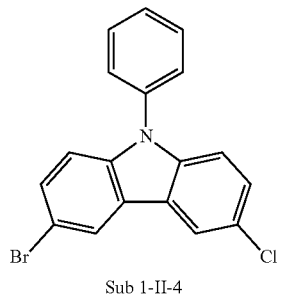
Sub 1-II-4

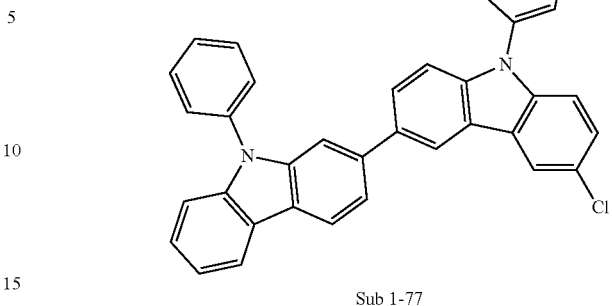
Sub 1-77

Sub 1-I-1 (45.0 g, 121.86 mmol) and Sub 1-II-4 (43.36 g, 121.86 mmol) were reacted using the synthesis method of Sub 1-1 described above to give 48 g of the product (yield: 76%).

Synthesis Examples of Sub 1(1) 5)

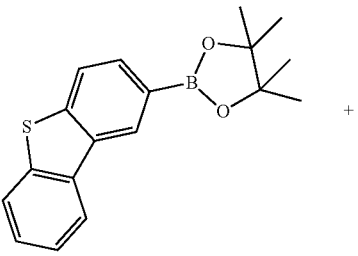
Sub 1-I-2

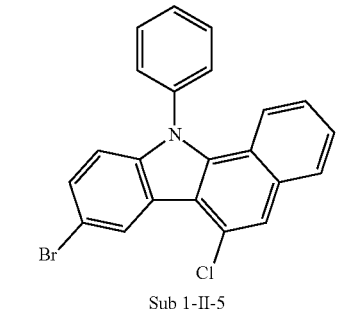
Sub 1-II-5

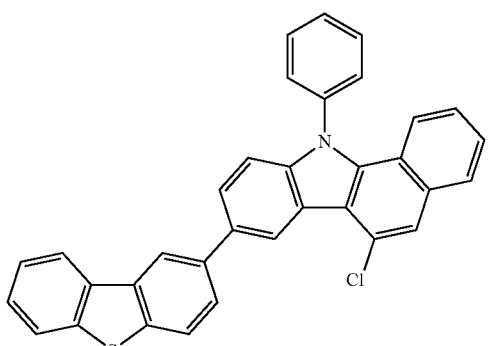
Sub 1-84

Sub 1-I-2 (38.5 g, 124.11 mmol) and Sub 1-II-5 (50.47 g, 124.11 mmol) were reacted using the synthesis method of Sub 1-1 described above to give 47.6 g of the product (yield: 75%).
Examples of Sub 1 comprise, but are not limited to, the followings.
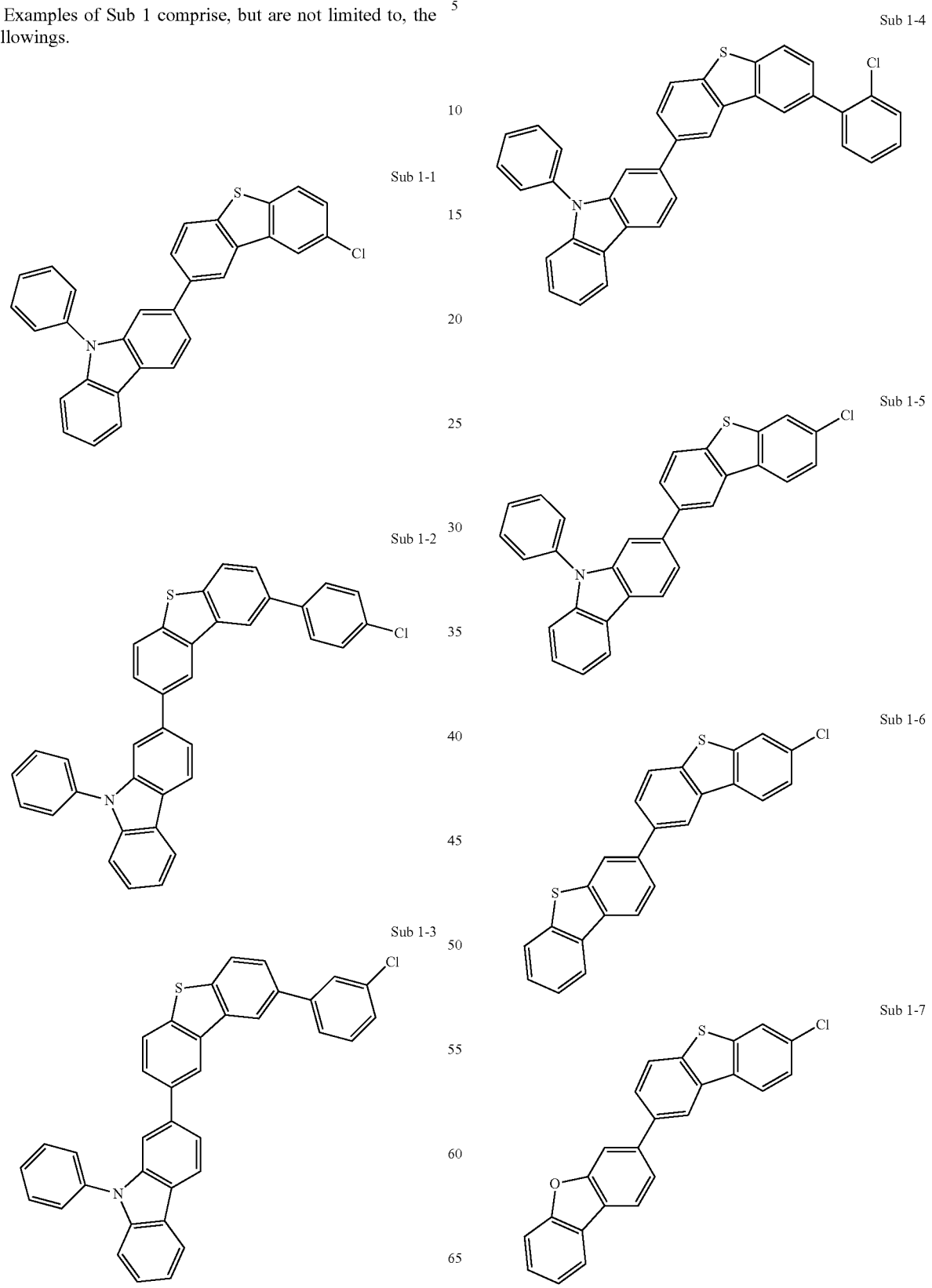

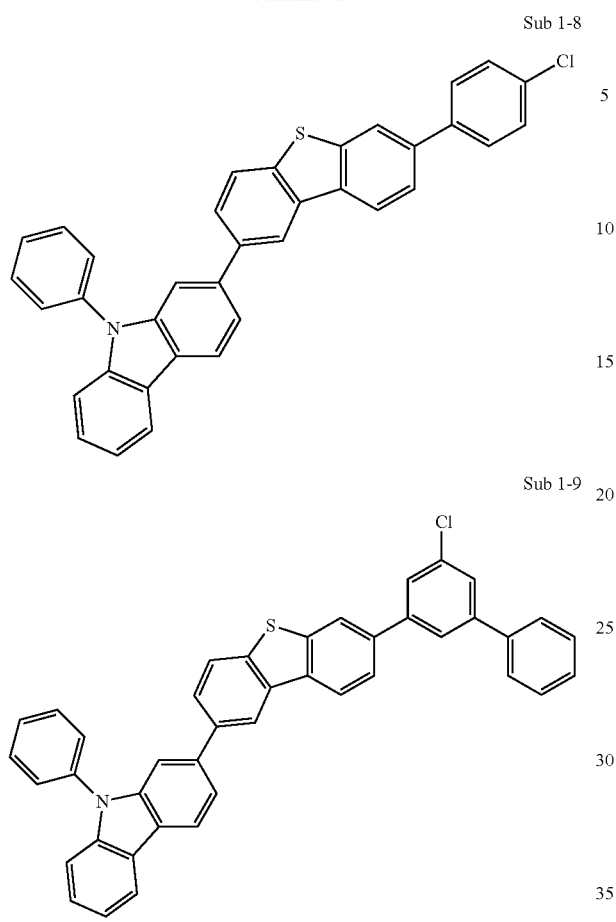
Sub 1-8
Sub 1-9
Sub 1-10
Sub 1-11
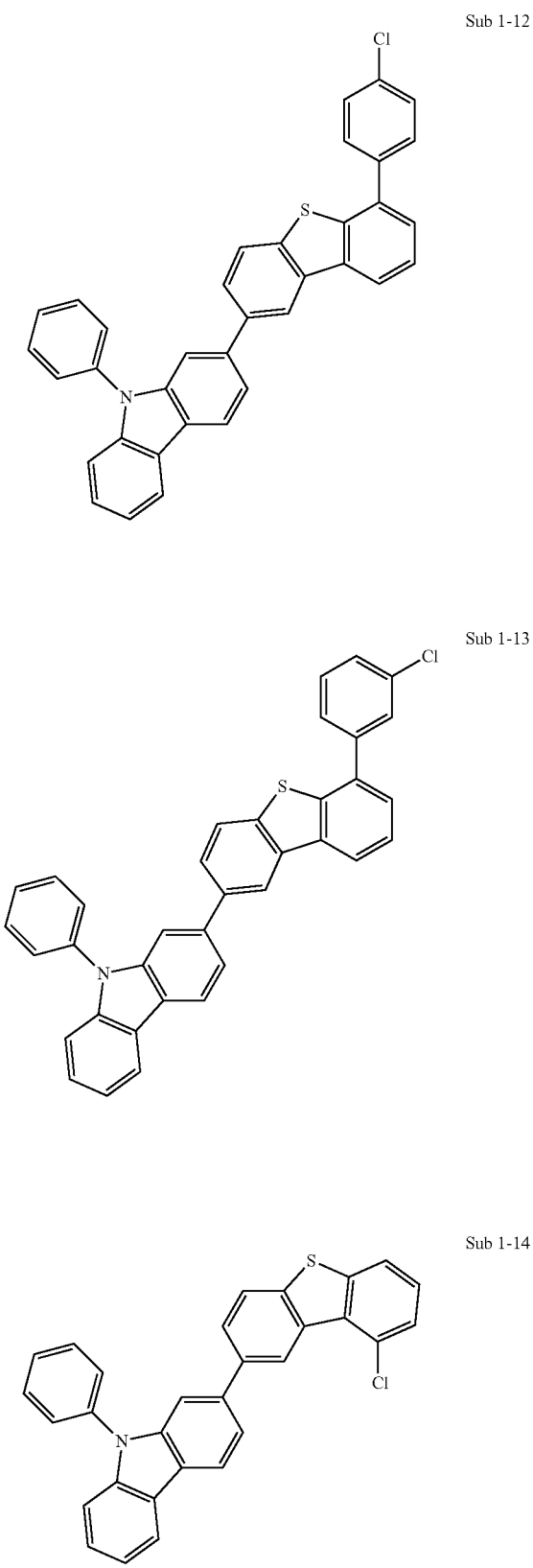
Sub 1-12
Sub 1-13
Sub 1-14

Sub 1-15
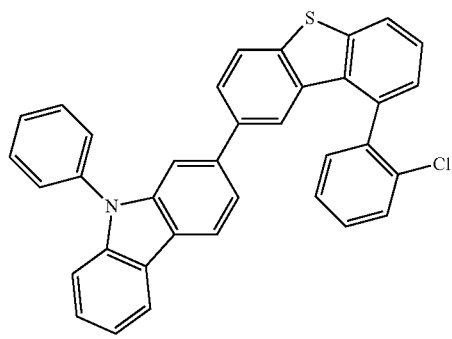
Sub 1-16
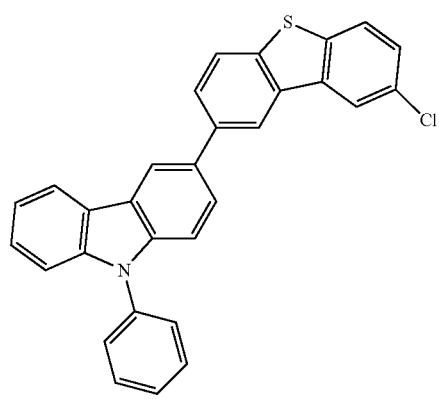
Sub 1-17
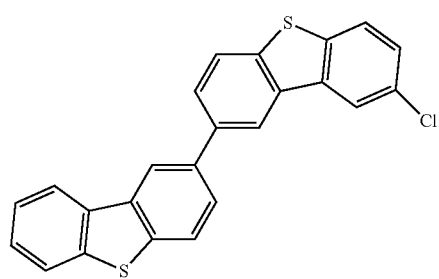
Sub 1-18
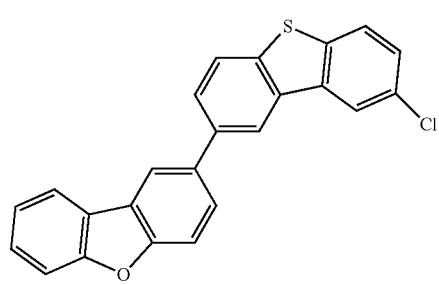
Sub 1-19
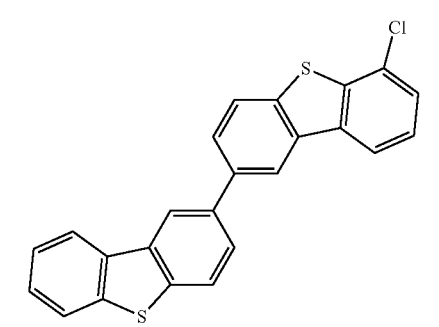
Sub 1-20
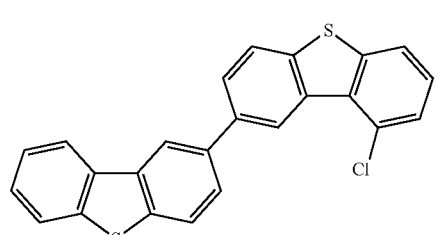
Sub 1-21
Sub 1-22
Sub 1-23

Sub 1-24
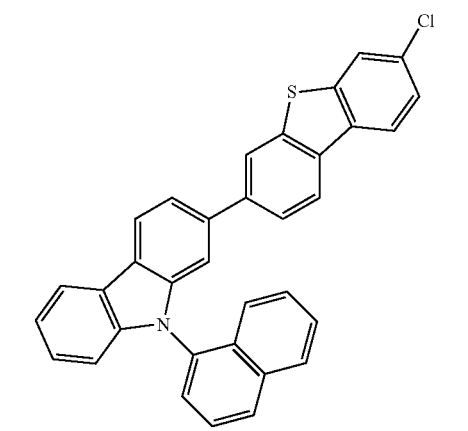
Sub 1-25
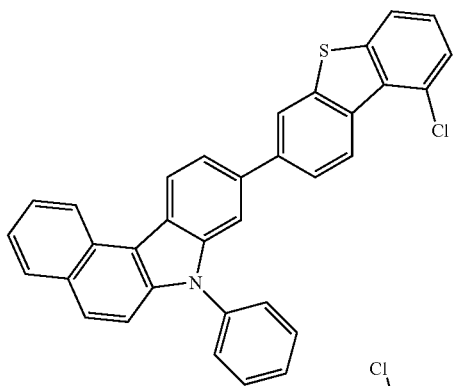
Sub 1-26
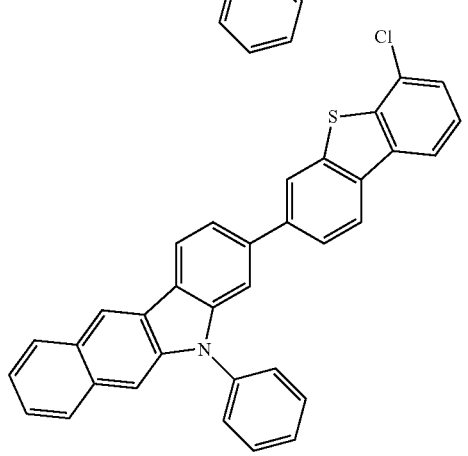
Sub 1-27
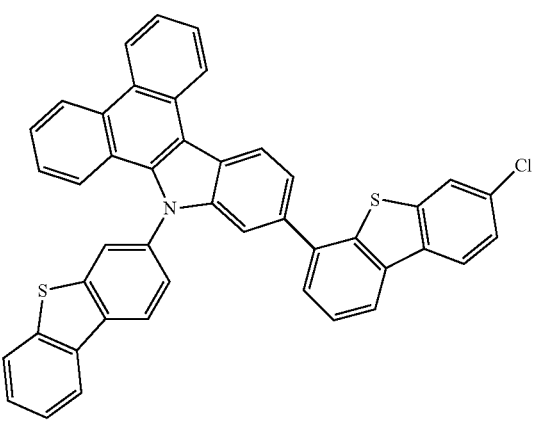
Sub 1-28
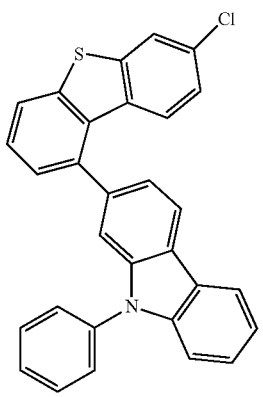
Sub 1-29
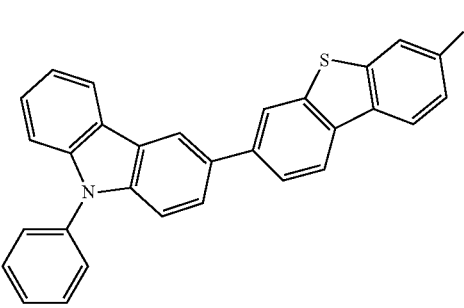
Sub 1-30
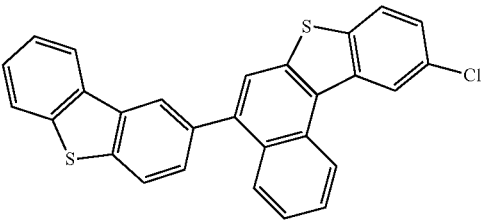
Sub 1-31
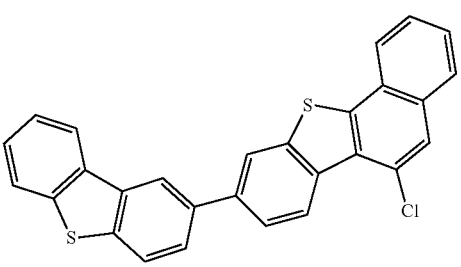
Sub 1-32
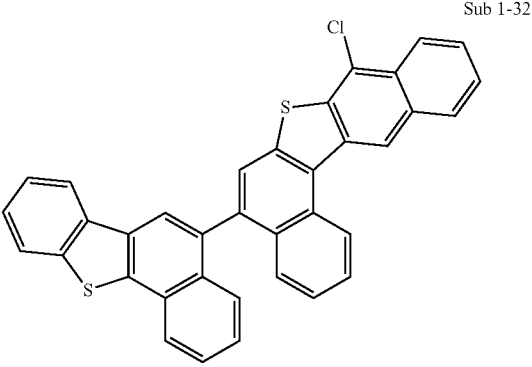

Sub 1-33
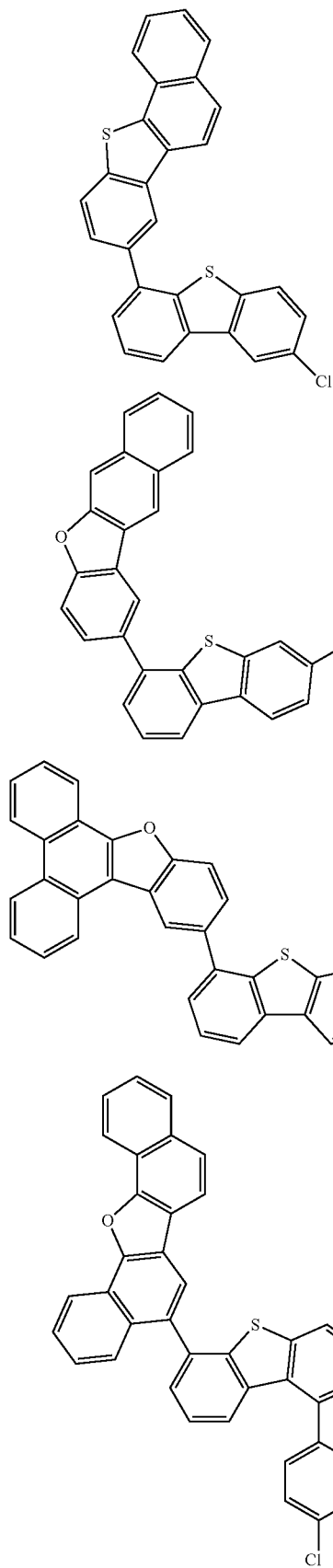
Sub 1-34
Sub 1-35
Sub 1-36
Sub 1-37
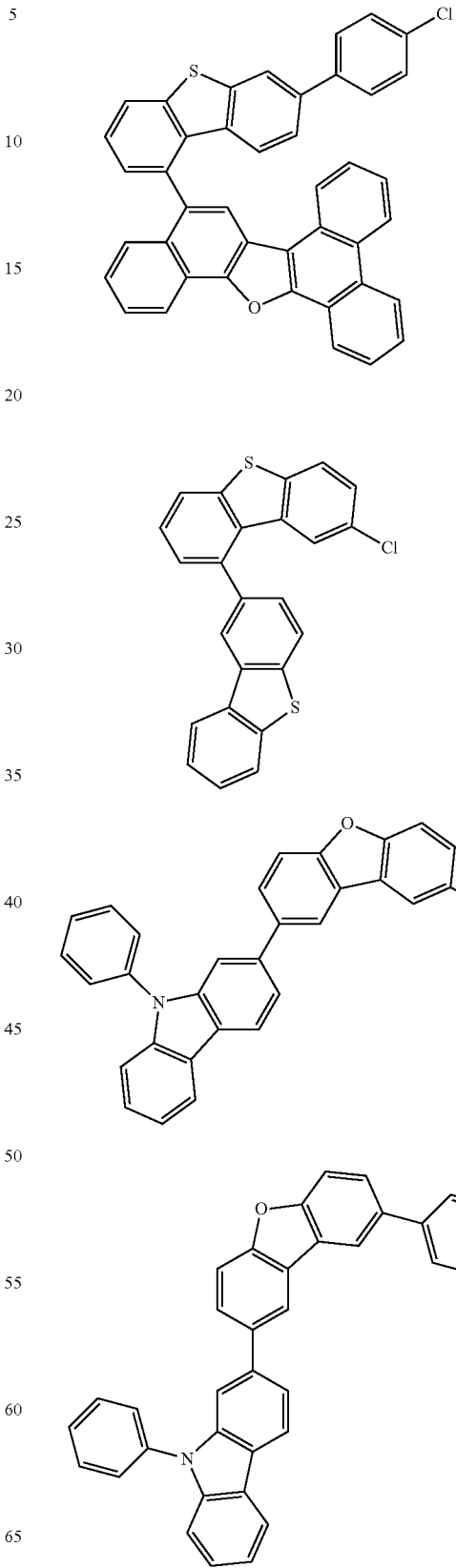
Sub 1-38
Sub 1-39
Sub 1-40

Sub 1-41
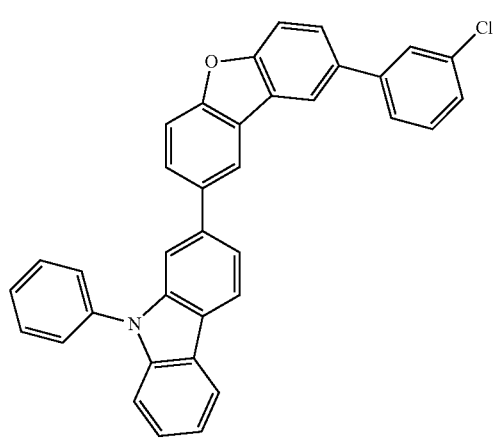
Sub 1-42
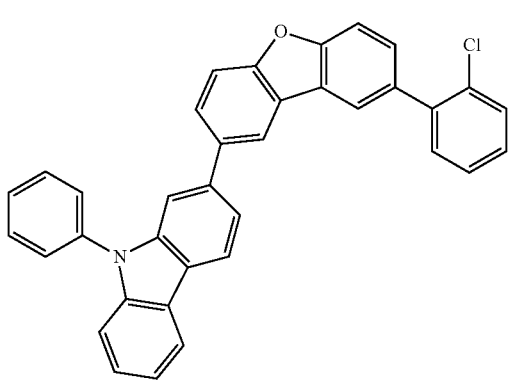
Sub 1-43
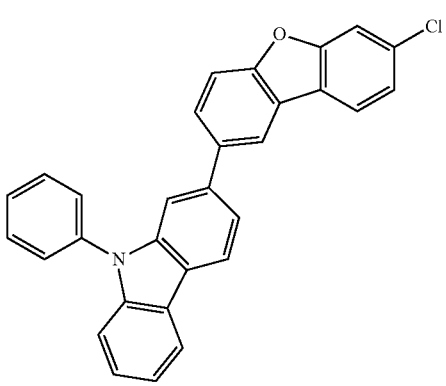
Sub 1-44
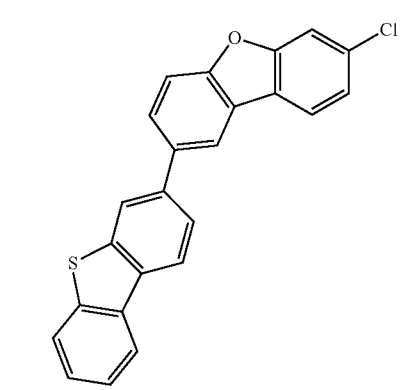
Sub 1-45
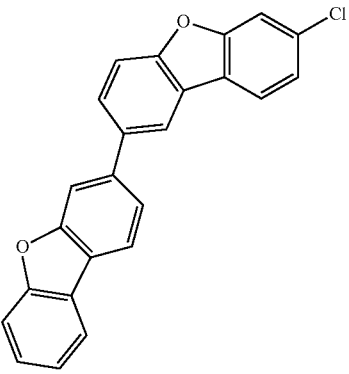
Sub 1-46
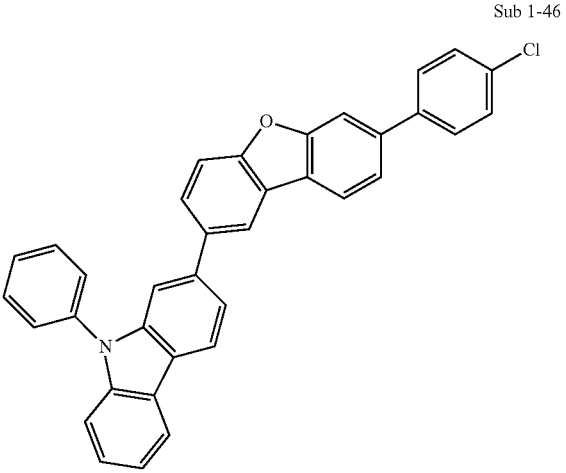
Sub 1-47
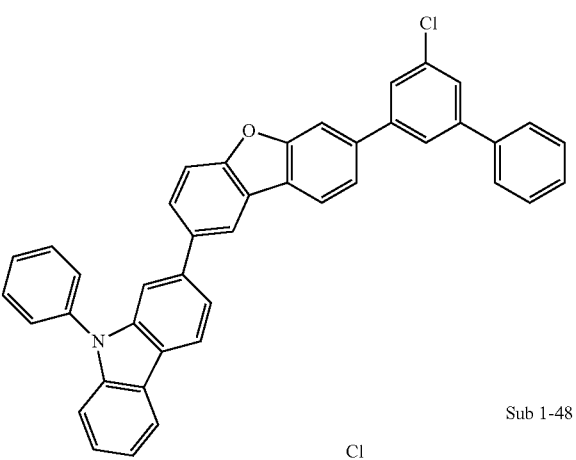
Sub 1-48
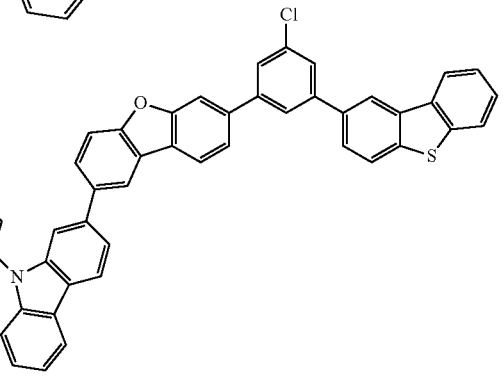

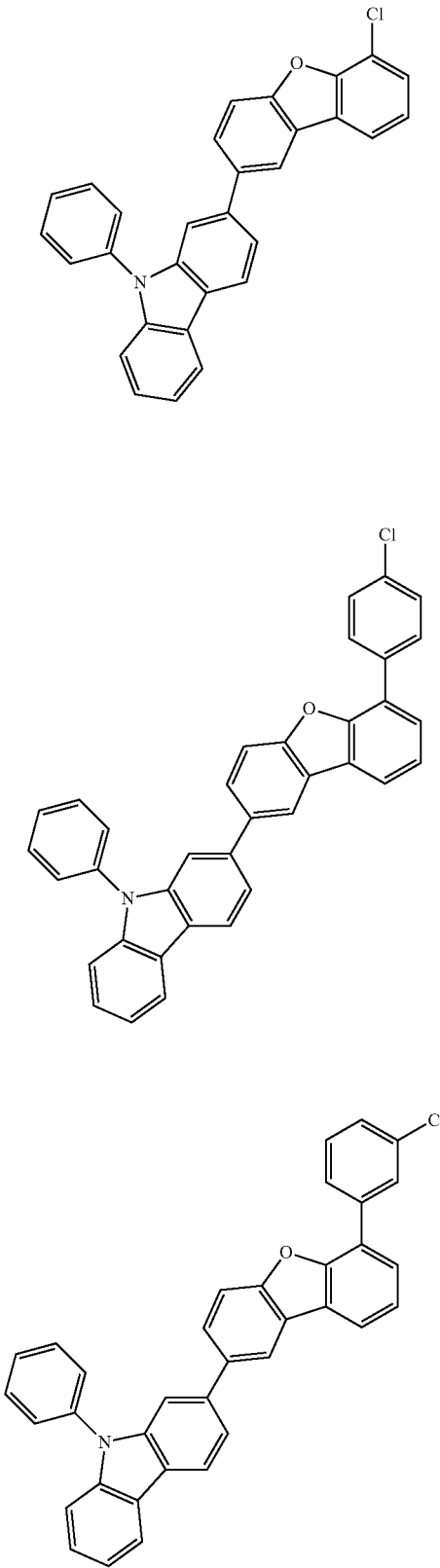
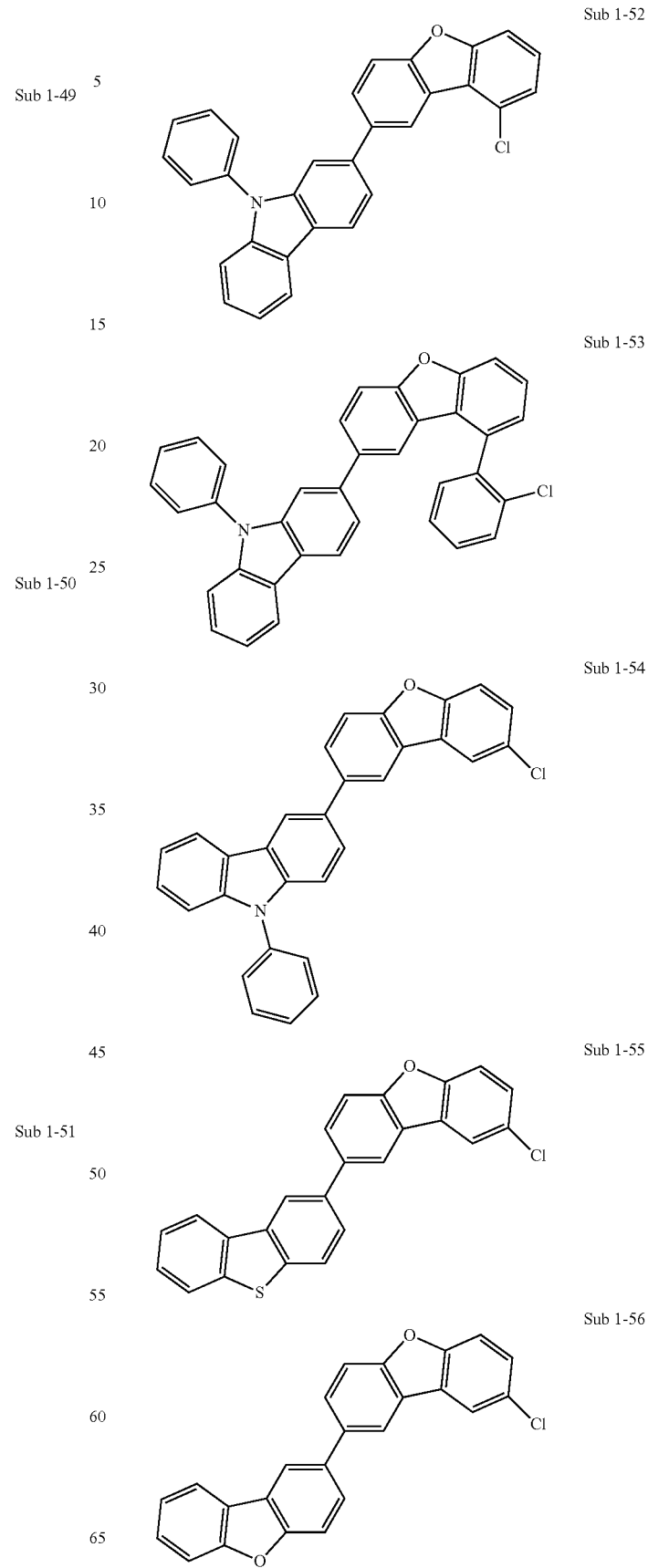

Sub 1-57
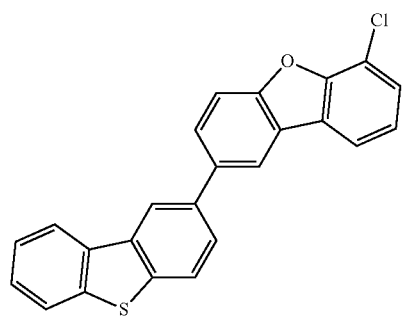
Sub 1-58
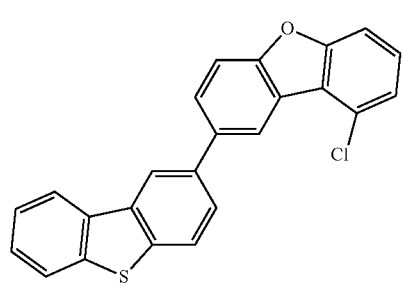
Sub 1-59
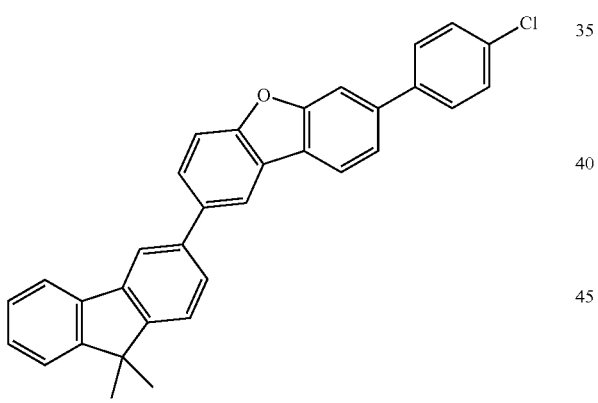
Sub 1-60
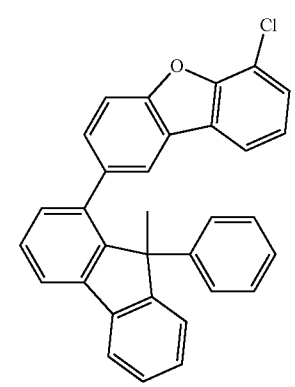
Sub 1-61
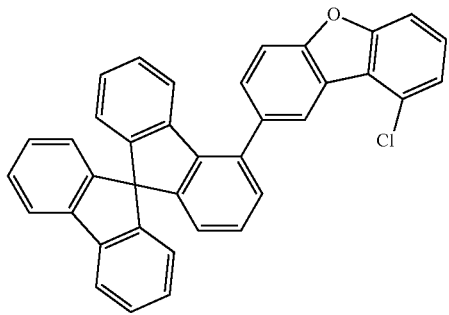
Sub 1-62
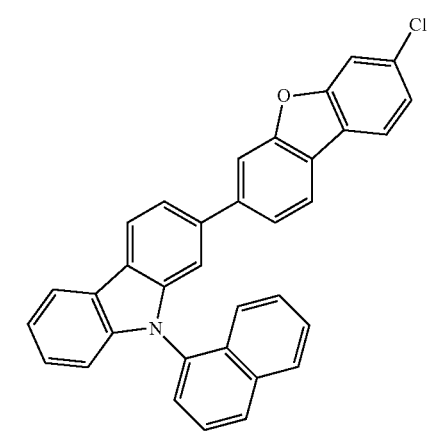
Sub 1-63
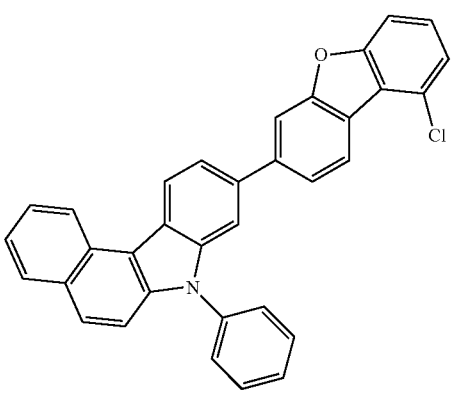
Sub 1-64
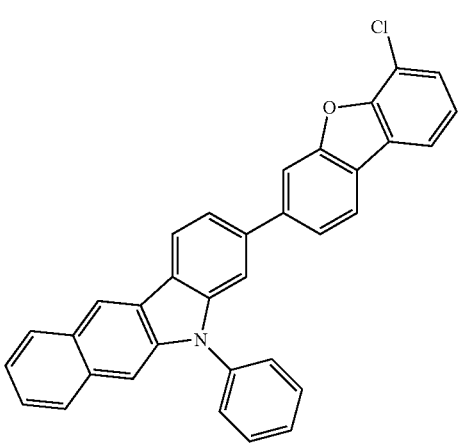

-continued
Sub 1-65
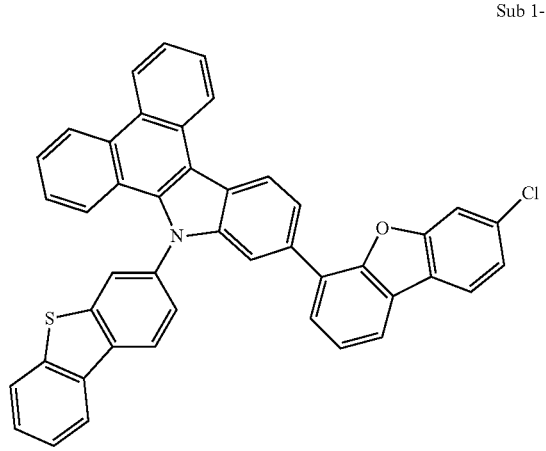
Sub 1-66
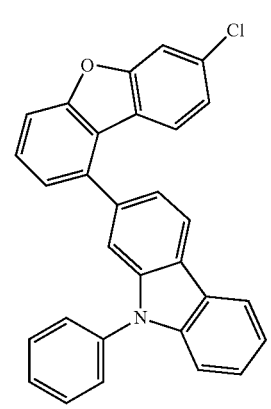
Sub 1-67
Sub 1-68
-continued
Sub 1-69
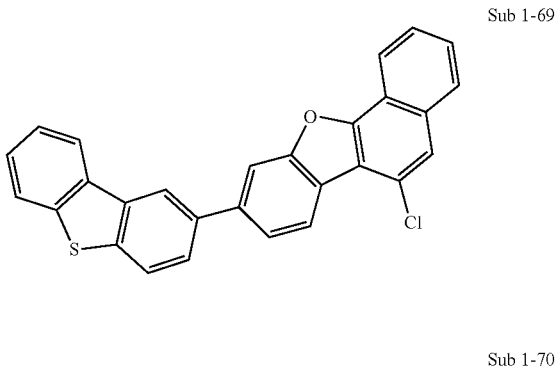
Sub 1-70
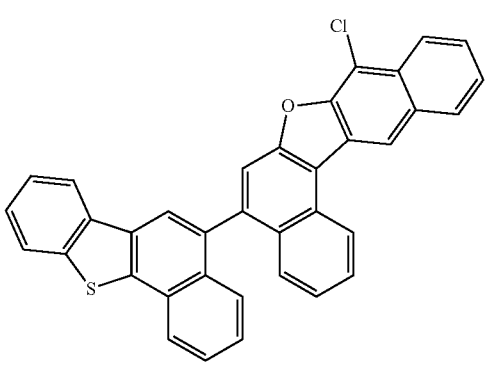
Sub 1-71
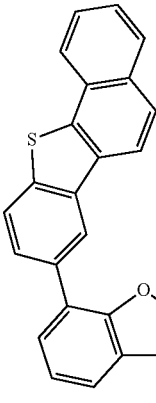
Sub 1-72
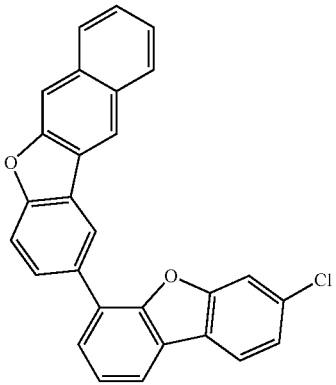

Sub 1-73
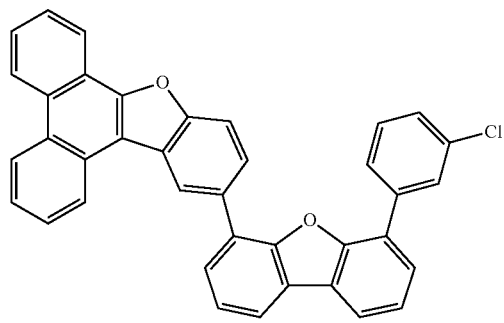
Sub 1-74
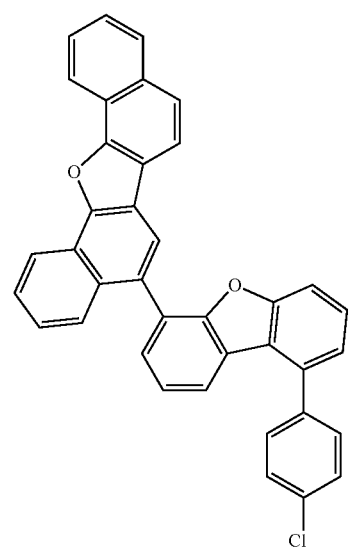
Sub 1-75
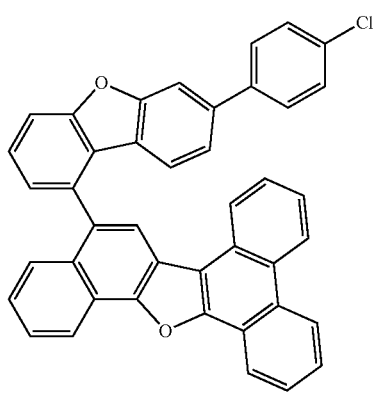
Sub 1-76
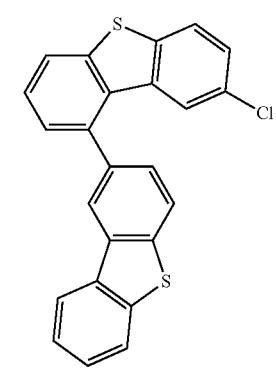
Sub 1-77
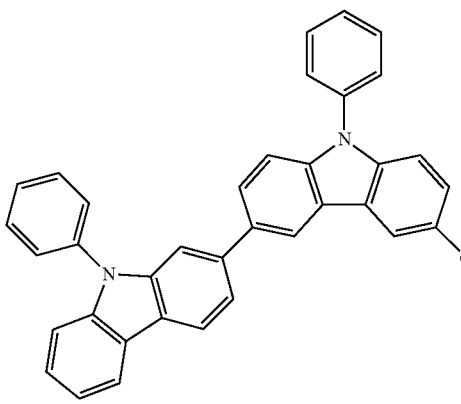
Sub 1-78
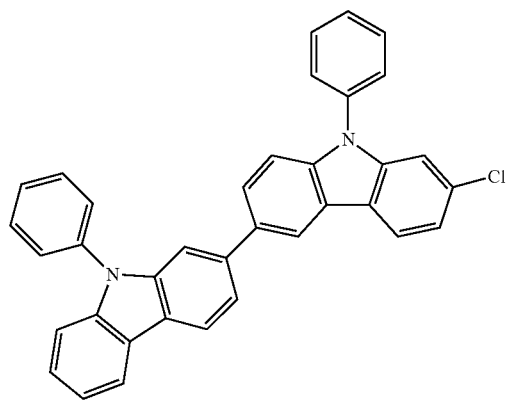
Sub 1-79
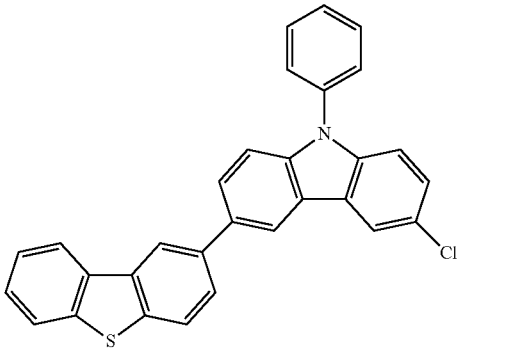
Sub 1-80
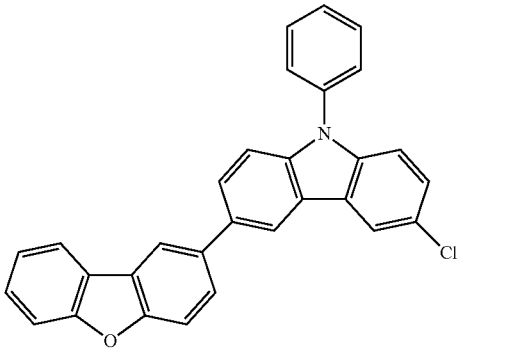

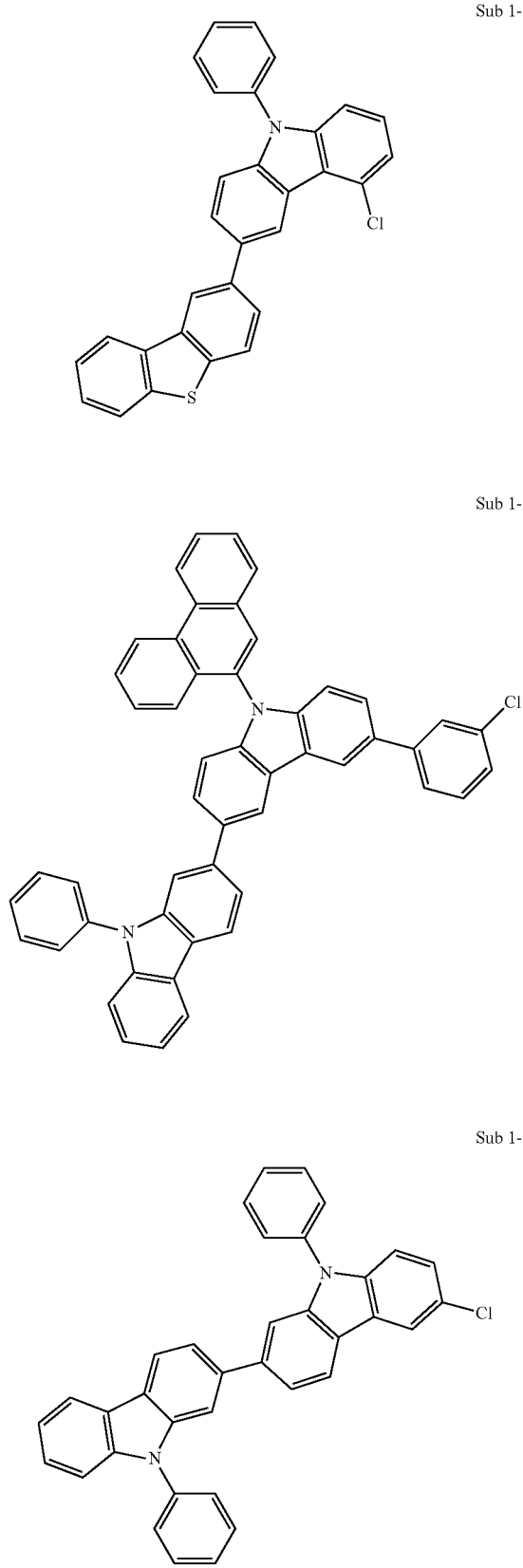
Sub 1-81
Sub 1-82
Sub 1-83
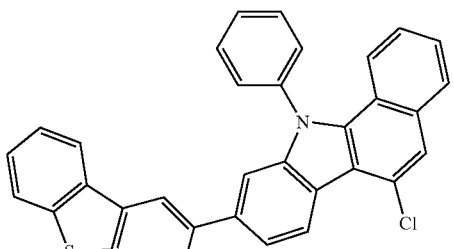
Sub 1-84
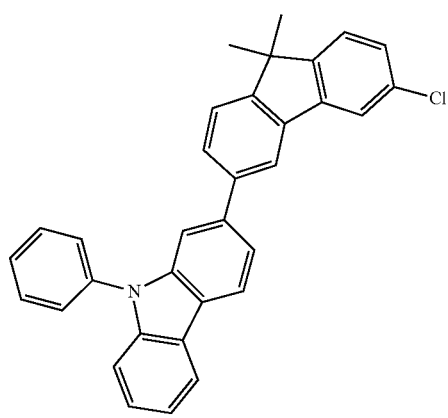
Sub 1-85
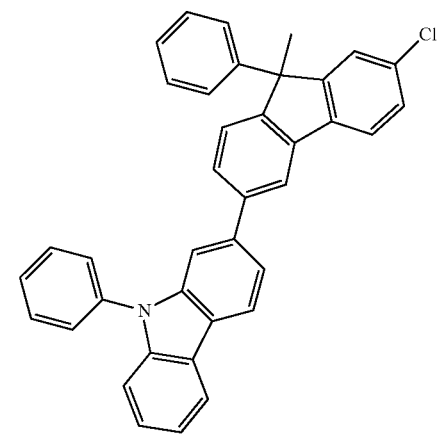
Sub 1-86
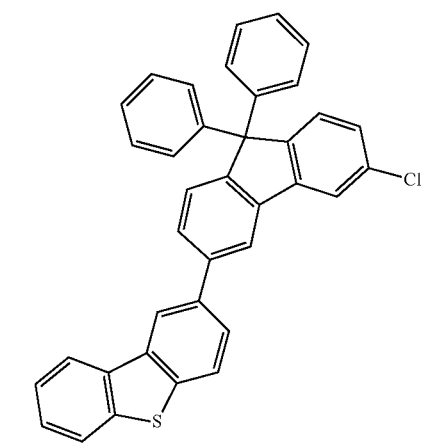
Sub 1-87

-continued

Sub 1-88

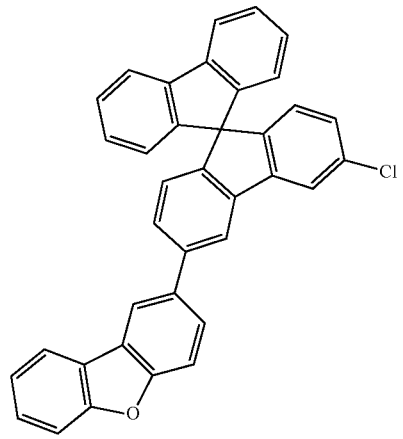

Sub 1-89

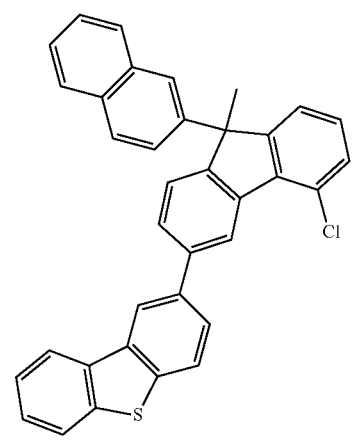

Sub 1-90

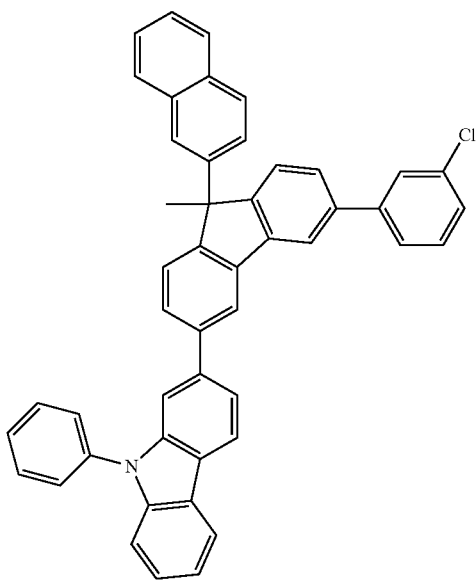

-continued

Sub 1-91

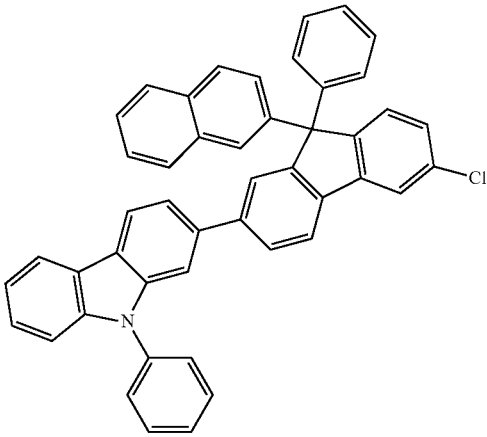

Sub 1-92

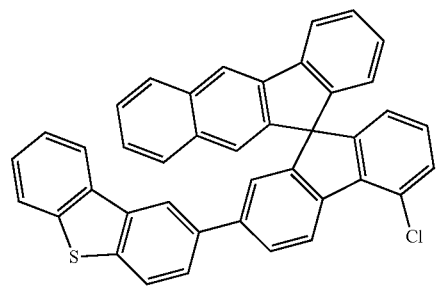

TABLE 1

| compounds | FD-MS | compounds | FD-MS |
|---|---|---|---|
| Sub 1-1 | m/z = 459.08 ($C_{30}H_{18}ClNS$ = 459.99) | Sub 1-2 | m/z = 535.12 ($C_{36}H_{22}ClNS$ = 536.09) |
| Sub 1-3 | m/z = 535.12 ($C_{36}H_{22}ClNS$ = 536.09) | Sub 1-4 | m/z = 535.12 ($C_{36}H_{22}ClNS$ = 536.09) |
| Sub 1-5 | m/z = 459.08 ($C_{30}H_{18}ClNS$ = 459.99) | Sub 1-6 | m/z = 400.01 ($C_{24}H_{13}ClS_2$ = 400.94) |
| Sub 1-7 | m/z = 384.04 ($C_{24}H_{13}ClOS$ = 384.88) | Sub 1-8 | m/z = 535.12 ($C_{36}H_{22}ClNS$ = 536.09) |
| Sub 1-9 | m/z = 611.15 ($C_{42}H_{26}ClNS$ = 612.19) | Sub 1-10 | m/z = 717.14 ($C_{48}H_{28}ClNS_2$ = 718.33) |
| Sub 1-11 | m/z = 459.08 ($C_{30}H_{18}ClNS$ = 459.99) | Sub 1-12 | m/z = 535.12 ($C_{36}H_{22}ClNS$ = 536.09) |
| Sub 1-13 | m/z = 535.12 ($C_{36}H_{22}ClNS$ = 536.09) | Sub 1-14 | m/z = 459.08 ($C_{30}H_{18}ClNS$ = 459.99) |
| Sub 1-15 | m/z = 535.12 ($C_{36}H_{22}ClNS$ = 536.09) | Sub 1-16 | m/z = 459.08 ($C_{30}H_{18}ClNS$ = 459.99) |
| Sub 1-17 | m/z = 400.01 ($C_{24}H_{13}ClS_2$ = 400.94) | Sub 1-18 | m/z = 384.04 ($C_{24}H_{13}ClOS$ = 384.88) |
| Sub 1-19 | m/z = 400.01 ($C_{24}H_{13}ClS_2$ = 400.94) | Sub 1-20 | m/z = 400.01 ($C_{24}H_{13}ClS_2$ = 400.94) |
| Sub 1-21 | m/z = 486.12 ($C_{33}H_{23}ClS$ = 487.06) | Sub 1-22 | m/z = 471.11 ($C_{32}H_{21}ClS$ = 473.03) |
| Sub 1-23 | m/z = 532.11 ($C_{37}H_{21}ClS$ = 533.09) | Sub 1-24 | m/z = 509.10 ($C_{34}H_{20}ClNS$ = 510.05) |
| Sub 1-25 | m/z = 509.10 ($C_{34}H_{20}ClNS$ = 510.05) | Sub 1-26 | m/z = 509.10 ($C_{34}H_{20}ClNS$ = 510.05) |
| Sub 1-27 | m/z = 665.10 ($C_{44}H_{24}ClNS_2$ = 666.25) | Sub 1-28 | m/z = 459.08 ($C_{30}H_{18}ClNS$ = 459.99) |
| Sub 1-29 | m/z = 459.08 ($C_{30}H_{18}ClNS$ = 459.99) | Sub 1-30 | m/z = 450.03 ($C_{28}H_{15}ClS_2$ = 451.00) |
| Sub 1-31 | m/z = 450.03 ($C_{28}H_{15}ClS_2$ = 451.00) | Sub 1-32 | m/z = 550.06 ($C_{36}H_{19}ClS_2$ = 551.12) |
| Sub 1-33 | m/z = 450.03 ($C_{28}H_{15}ClS_2$ = 451.00) | Sub 1-34 | m/z = 434.05 ($C_{28}H_{15}ClOS$ = 434.94) |
| Sub 1-35 | m/z = 560.10 ($C_{38}H_{21}ClOS$ = 561.10) | Sub 1-36 | m/z = 560.10 ($C_{38}H_{21}ClOS$ = 561.10) |

TABLE 1-continued

| compounds | FD-MS | compounds | FD-MS |
|---|---|---|---|
| Sub 1-37 | m/z = 610.12 ($C_{42}H_{23}ClOS$ = 611.16) | Sub 1-38 | m/z = 400.01 ($C_{24}H_{13}ClS_2$ = 400.94) |
| Sub 1-39 | m/z = 443.10 ($C_{30}H_{18}ClNO$ = 443.93) | Sub 1-40 | m/z = 519.14 ($C_{36}H_{22}ClNO$ = 520.03) |
| Sub 1-41 | m/z = 519.14 ($C_{36}H_{22}ClNO$ = 520.03) | Sub 1-42 | m/z = 519.14 ($C_{36}H_{22}ClNO$ = 520.03) |
| Sub 1-43 | m/z = 443.10 ($C_{30}H_{18}ClNO$ = 443.93) | Sub 1-44 | m/z = 384.03 ($C_{24}H_{13}ClS$ = 384.88) |
| Sub 1-45 | m/z = 368.06 ($C_{24}H_{13}ClO_2$ = 368.82) | Sub 1-46 | m/z = 519.14 ($C_{36}H_{22}ClNO$ = 520.03) |
| Sub 1-47 | m/z = 595.17 ($C_{42}H_{26}ClNO$ = 596.13) | Sub 1-48 | m/z = 701.16 ($C_{48}H_{28}ClNOS$ = 702.27) |
| Sub 1-49 | m/z = 443.10 ($C_{30}H_{18}ClNO$ = 443.93) | Sub 1-50 | m/z = 519.14 ($C_{36}H_{22}ClNO$ = 520.03) |
| Sub 1-51 | m/z = 519.14 ($C_{36}H_{22}ClNO$ = 520.03) | Sub 1-52 | m/z = 443.10 ($C_{30}H_{18}ClNO$ = 443.93) |
| Sub 1-53 | m/z = 519.14 ($C_{36}H_{22}ClNO$ = 520.03) | Sub 1-54 | m/z = 443.10 ($C_{30}H_{18}ClNO$ = 443.93) |
| Sub 1-55 | m/z = 384.03 ($C_{24}H_{13}ClOS$ = 384.88) | Sub 1-56 | m/z = 368.06 ($C_{24}H_{13}ClO_2$ = 368.82) |
| Sub 1-57 | m/z = 384.03 ($C_{24}H_{13}ClOS$ = 384.88) | Sub 1-58 | m/z = 384.03 ($C_{24}H_{13}ClOS$ = 384.88) |
| Sub 1-59 | m/z = 474.14 ($C_{33}H_{23}ClO$ = 471.10) | Sub 1-60 | m/z = 455.13 ($C_{32}H_{21}ClO$ = 456.97) |
| Sub 1-61 | m/z = 516.13 ($C_{37}H_{21}ClO$ = 517.03) | Sub 1-62 | m/z = 493.12 ($C_{34}H_{20}ClNO$ = 493.99) |
| Sub 1-63 | m/z = 493.12 ($C_{34}H_{20}ClNO$ = 493.99) | Sub 1-64 | m/z = 493.12 ($C_{34}H_{20}ClNO$ = 493.99) |
| Sub 1-65 | m/z = 649.12 ($C_{44}H_{24}ClNOS$ = 650.19) | Sub 1-66 | m/z = 443.10 ($C_{30}H_{18}ClNO$ = 443.93) |
| Sub 1-67 | m/z = 443.10 ($C_{30}H_{18}ClNO$ = 443.93) | Sub 1-68 | m/z = 434.05 ($C_{28}H_{15}ClOS$ = 434.94) |
| Sub 1-69 | m/z = 434.05 ($C_{28}H_{15}ClOS$ = 434.94) | Sub 1-70 | m/z = 534.08 ($C_{36}H_{19}ClOS$ = 535.06) |
| Sub 1-71 | m/z = 434.05 ($C_{28}H_{15}ClOS$ = 434.94) | Sub 1-72 | m/z = 418.07 ($C_{28}H_{15}ClO_2$ = 418.88) |
| Sub 1-73 | m/z = 544.12 ($C_{38}H_{21}ClOS$ = 545.04) | Sub 1-74 | m/z = 544.12 ($C_{38}H_{21}ClOS$ = 545.04) |
| Sub 1-75 | m/z = 594.14 ($C_{42}H_{23}ClO_2$ = 595.10) | Sub 1-76 | m/z = 384.03 ($C_{24}H_{13}ClOS$ = 384.88) |
| Sub 1-77 | m/z = 518.15 ($C_{36}H_{24}ClN_2$ = 519.04) | Sub 1-78 | m/z = 518.15 ($C_{36}H_{24}ClN_2$ = 519.04) |
| Sub 1-79 | m/z = 459.08 ($C_{30}H_{18}ClNS$ = 459.99) | Sub 1-80 | m/z = 443.10 ($C_{30}H_{18}ClNO$ = 443.93) |
| Sub 1-81 | m/z = 459.08 ($C_{30}H_{18}ClNS$ = 459.99) | Sub 1-82 | m/z = 694.22 ($C_{50}H_{31}ClN_2$ = 695.26) |
| Sub 1-83 | m/z = 518.15 ($C_{36}H_{24}ClN_2$ = 519.04) | Sub 1-84 | m/z = 509.10 ($C_{34}H_{20}ClNS$ = 510.05) |
| Sub 1-85 | m/z = 469.16 ($C_{33}H_{24}ClN$ = 470.01) | Sub 1-86 | m/z = 531.18 ($C_{38}H_{26}ClN$ = 532.08) |
| Sub 1-87 | m/z = 534.12 ($C_{37}H_{23}ClS$ = 535.10) | Sub 1-88 | m/z = 516.13 ($C_{37}H_{21}ClO$ = 517.02) |
| Sub 1-89 | m/z = 522.12 ($C_{36}H_{23}ClS$ = 523.09) | Sub 1-90 | m/z = 657.22 ($C_{48}H_{32}ClN$ = 658.24) |
| Sub 1-91 | m/z = 643.21 ($C_{47}H_{30}ClN$ = 644.21) | Sub 1-92 | m/z = 582.12 ($C_{41}H_{23}ClS$ = 583.15) |

Synthesis Example of Sub 2

Sub 2 of Reaction Scheme 1 can be synthesized by the reaction path of the following Reaction Scheme 3, but is not limited thereto.

<Reaction Scheme 3>

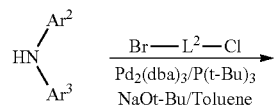

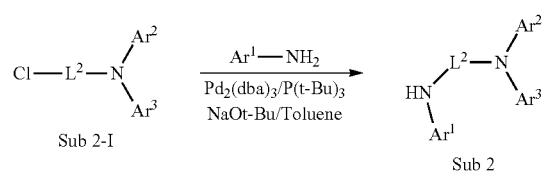

Synthesis Examples of Sub 2-1

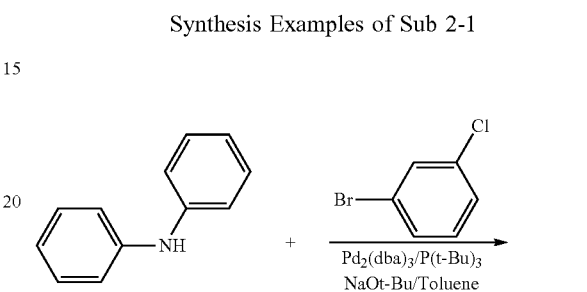

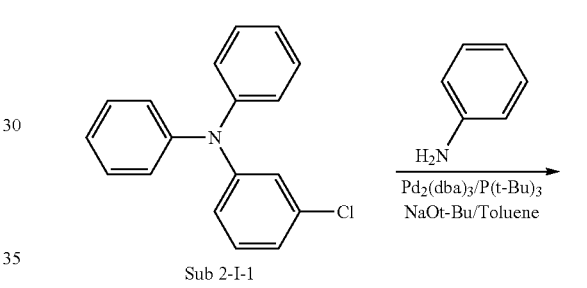

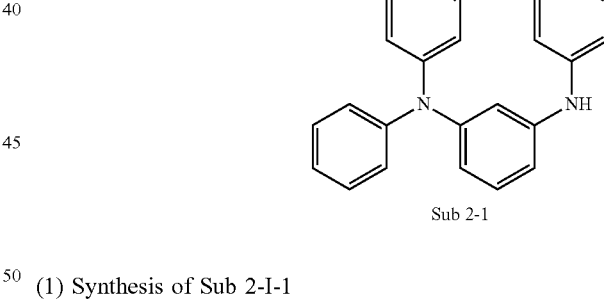

Sub 2-1

(1) Synthesis of Sub 2-I-1

Diphenylamine (37.0 g, 218.64 mmol) was added to a round bottom flask and dissolved in toluene (1100 mL), and 1-bromo-3-chlorobenzene 41.86 g, 218.64 mmol), $Pd_2(dba)_3$ (6.01 g, 6.56 mmol), $P(t-Bu)_3$ (2.65 g, 13.12 mmol), NaOt-Bu (63.03 g, 655.9 mmol) were added in the order and stirred at 100° C. After the reaction was completed, the reaction mixture was extracted with ether and water. The organic layer was dried over $MgSO_4$ and concentrated. The resulting compound was separated by silicagel column chromatography and recrystallized to obtain 47.6 g of the product. (yield: 78%)

(2) Synthesis of Sub 2-1

Sub 2-I-1 (47.6 g, 170.14 mmol) and aniline (23.7 g, 255.21 mmol) were reacted using the synthesis method of Sub 2-I-1 described above to give 42 g of the product (yield: 73%).

Synthesis Example of Sub 2-13

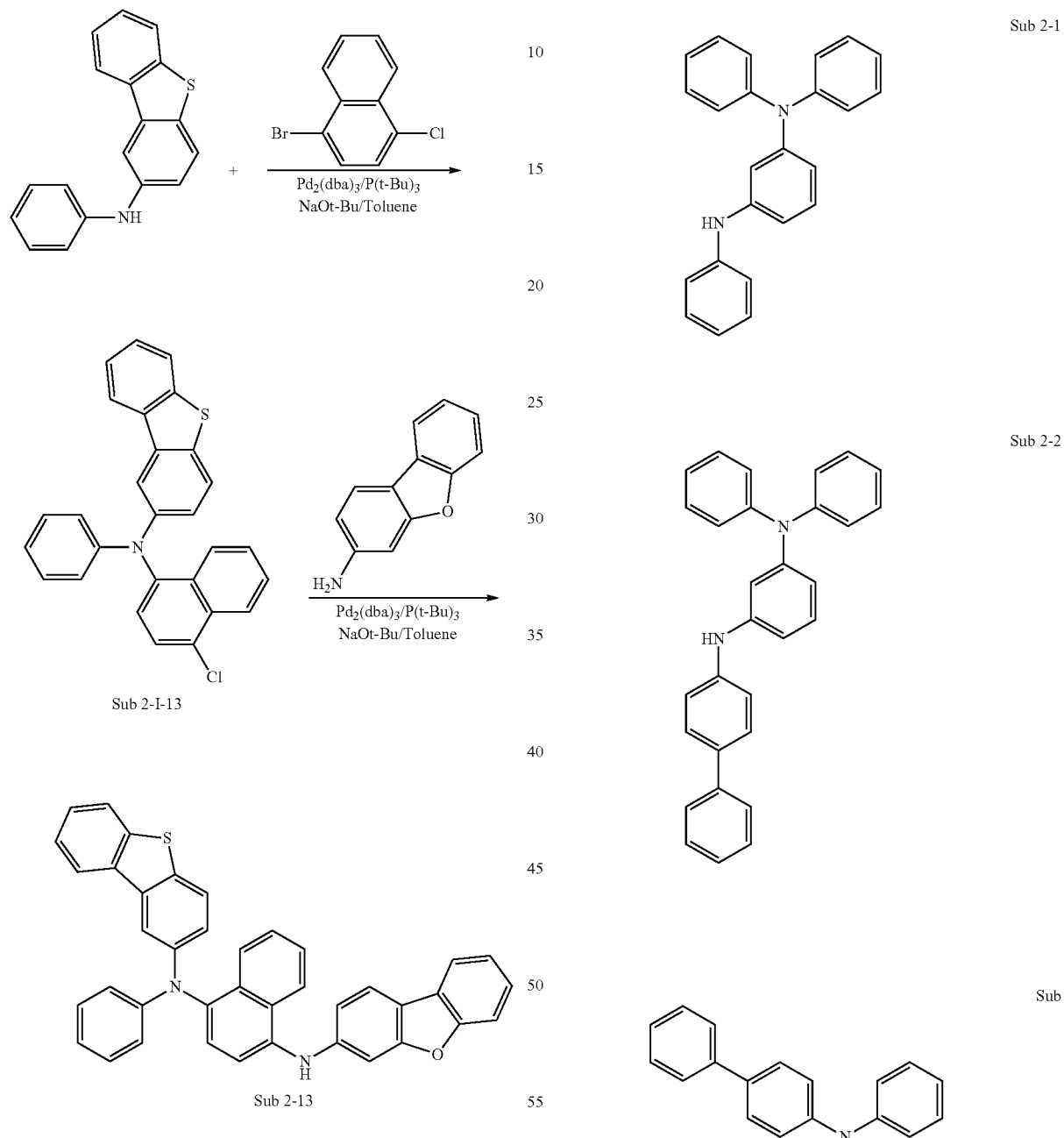

Examples of Sub 2 comprise, but are not limited to, the followings.

(1) Synthesis of Sub 2-I-13

N-phenyldibenzo[b,d]thiophen-2-amine (30.0 g, 108.94 mmol) and 1-bromo-4-chloronaphthalene (26.3 g, 108.94 mmol) were reacted using the synthesis method of Sub 2-I-1 described above to give 34.8 g of the product (yield: 73%).

(2) Synthesis of Sub 2-1

Sub 2-I-13 (34.8 g, 79.82 mmol) and aniline (21.94 g, 119.73 mmol) were reacted using the synthesis method of Sub 2-I-1 described above to give 40.6 g of the product (yield: 87%).

Sub 2-4
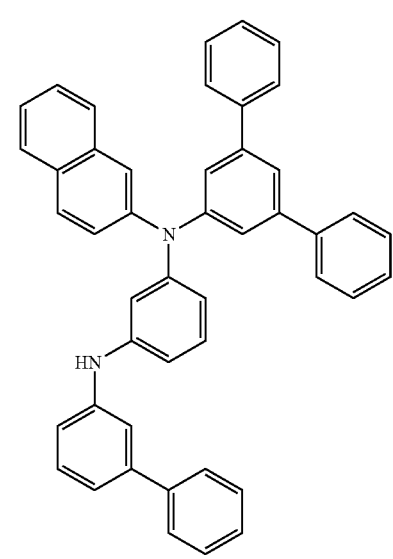
Sub 2-7
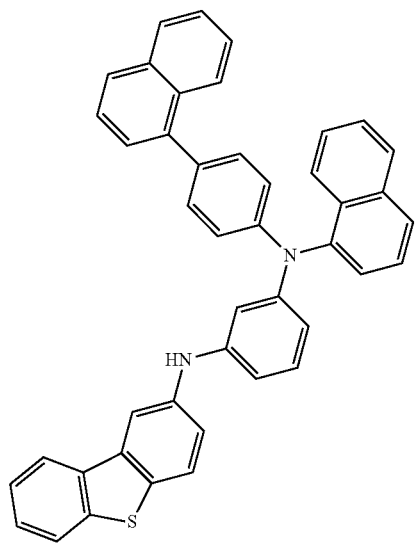
Sub 2-5
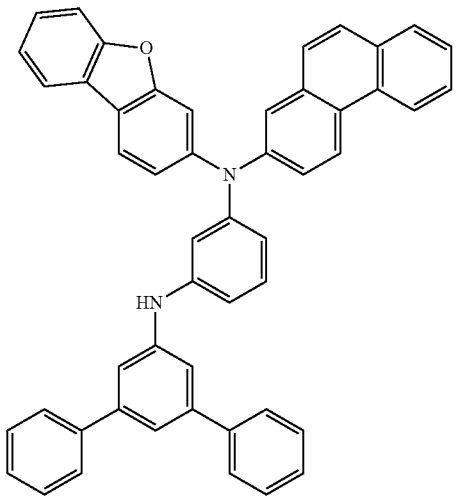
Sub 2-8
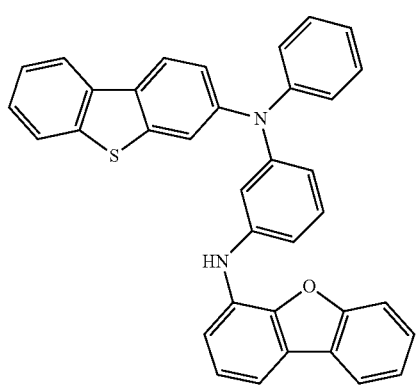
Sub 2-6
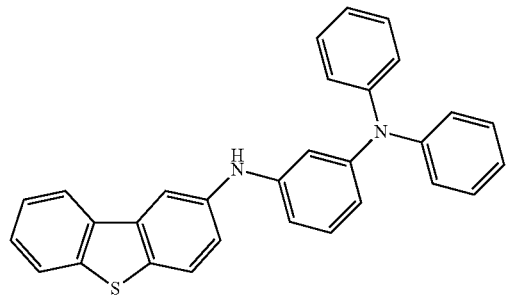
Sub 2-9
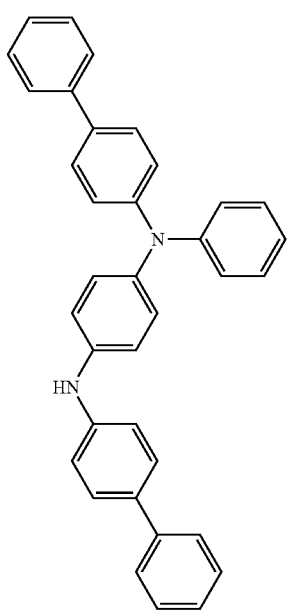

Sub 2-10
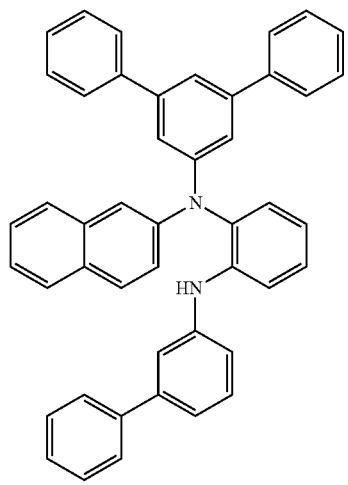
Sub 2-13
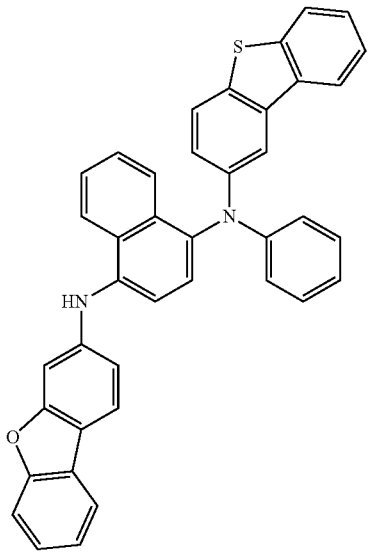
Sub 2-11
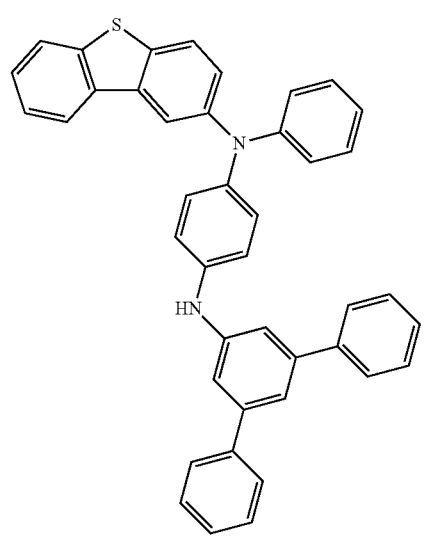
Sub 2-14
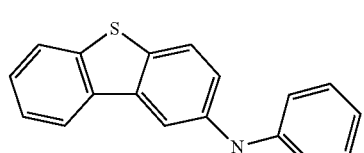
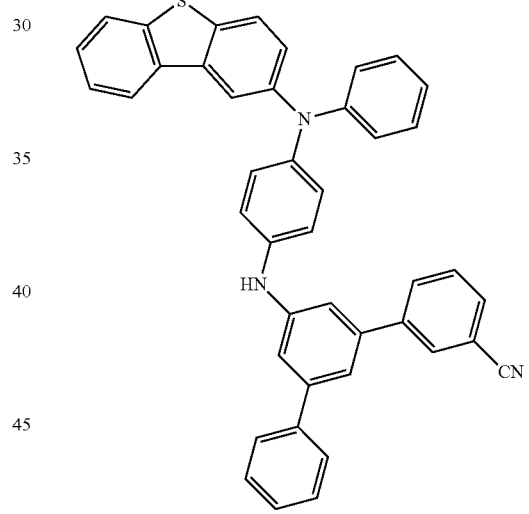
Sub 2-12
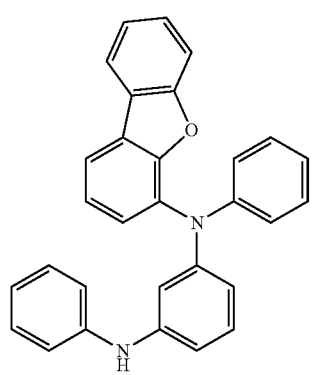
Sub 2-15
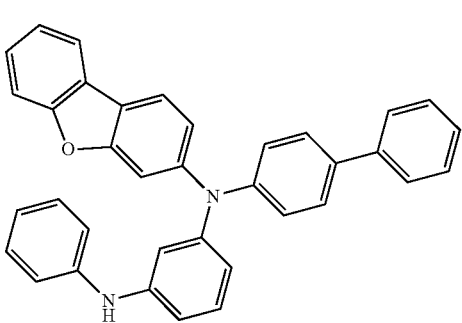

Sub 2-16
Sub 2-17
Sub 2-18
Sub 2-19
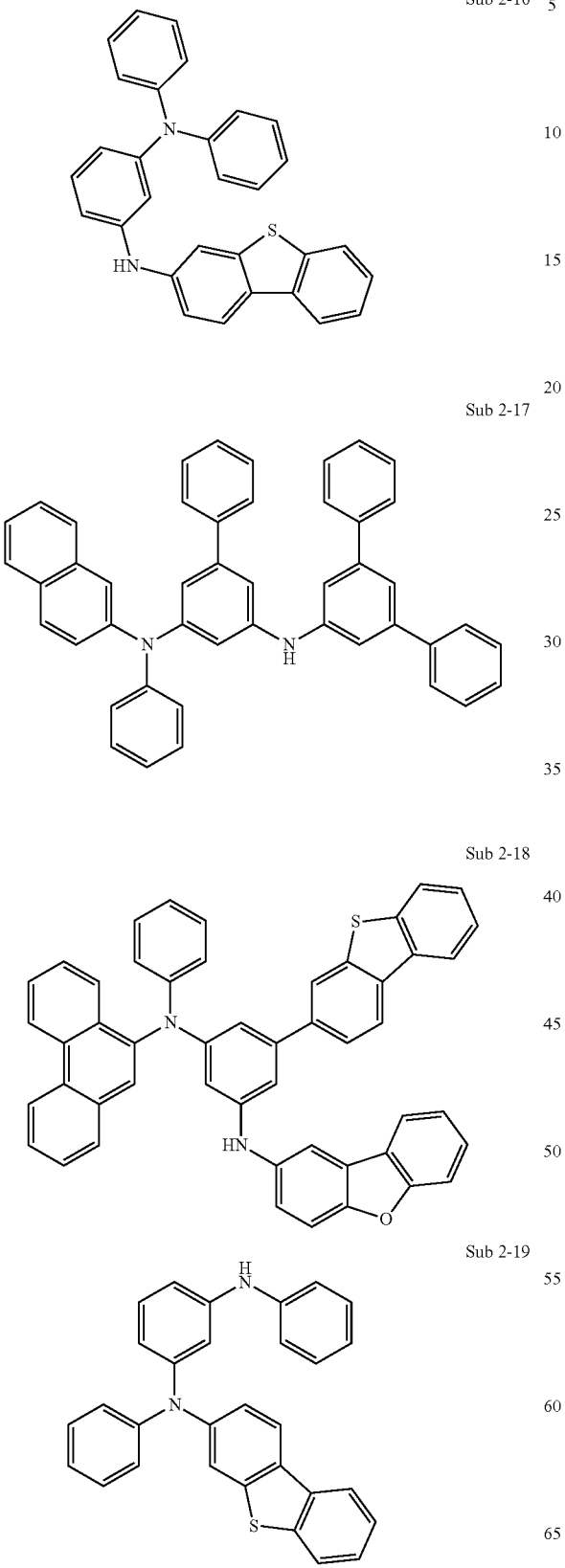
Sub 2-20
Sub 2-21
Sub 2-22
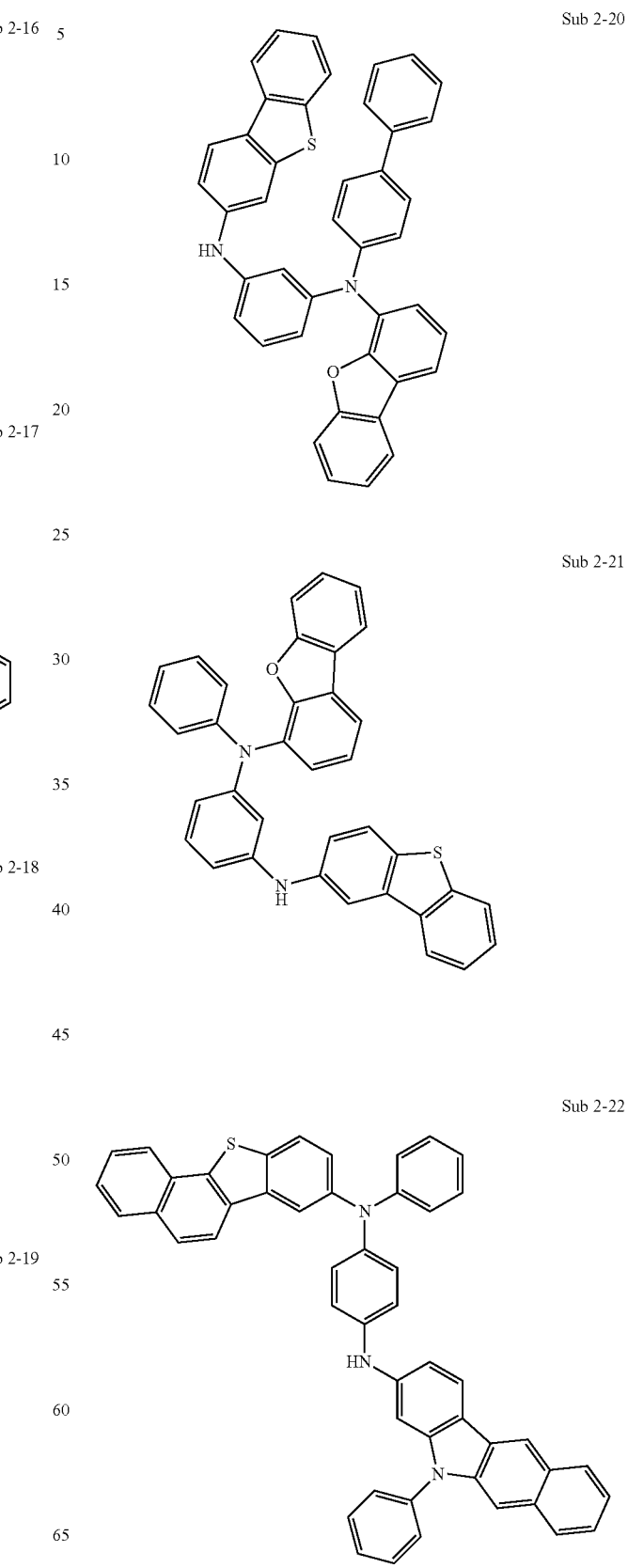

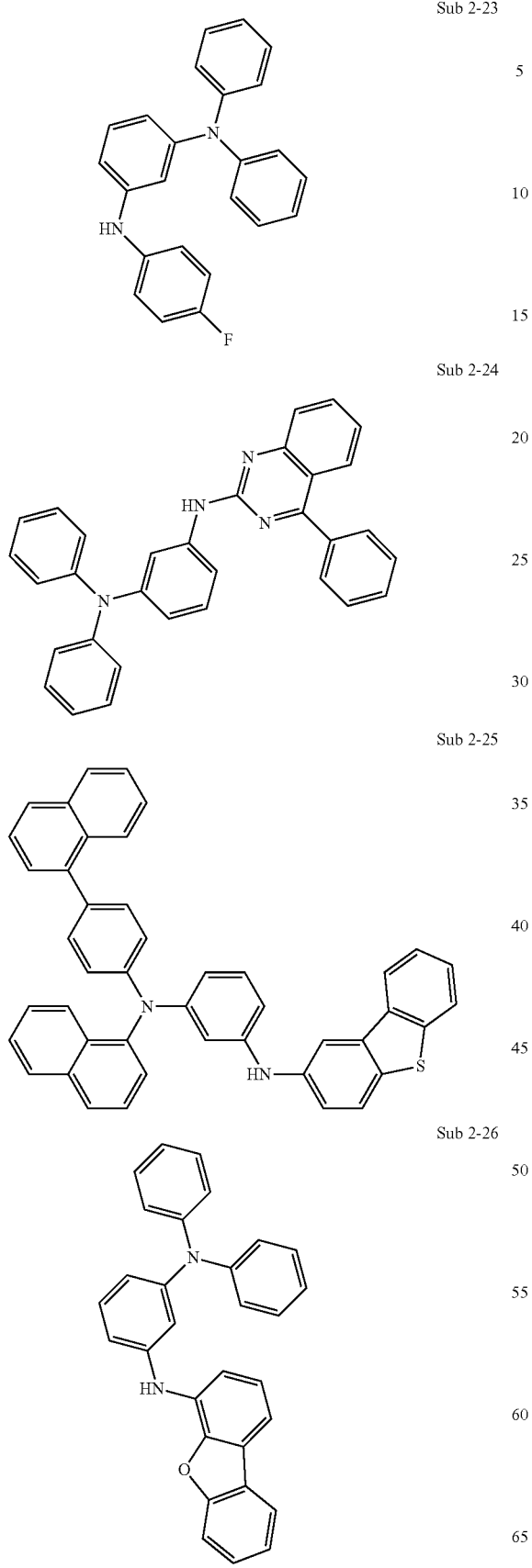
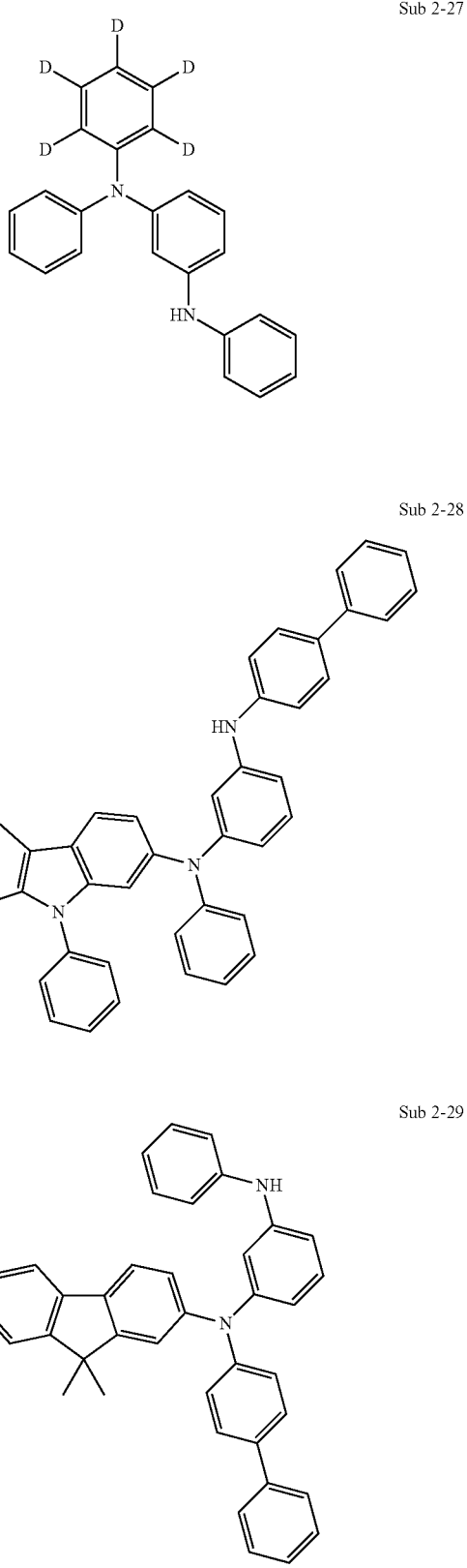

-continued

Sub 2-30

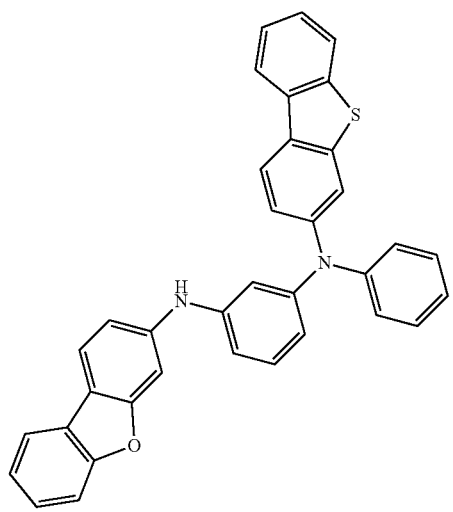

TABLE 2

| compound | FD-MS | compound | FD-MS |
|---|---|---|---|
| Sub 2-1 | m/z = 336.16 ($C_{24}H_{20}N_2$ = 336.44) | Sub 2-2 | m/z = 412.19 ($C_{30}H_{24}N_2$ = 412.54) |
| Sub 2-3 | m/z = 412.19 ($C_{30}H_{24}N_2$ = 412.54) | Sub 2-4 | m/z = 614.27 ($C_{46}H_{34}N_2$ = 614.79) |
| Sub 2-5 | m/z = 678.27 ($C_{50}H_{34}N_2O$ = 678.84) | Sub 2-6 | m/z = 442.15 ($C_{30}H_{22}N_2S$ = 442.58) |
| Sub 2-7 | m/z = 618.21 ($C_{44}H_{30}N_2S$ = 618.80) | Sub 2-8 | m/z = 532.16 ($C_{36}H_{24}N_2OS$ = 532.66) |
| Sub 2-9 | m/z = 488.23 ($C_{36}H_{28}N_2$ = 488.63) | Sub 2-10 | m/z = 614.27 ($C_{46}H_{34}N_2$ = 614.79) |
| Sub 2-11 | m/z = 594.21 ($C_{42}H_{30}N_2S$ = 594.78) | Sub 2-12 | m/z = 426.17 ($C_{30}H_{22}N_2O$ = 426.52) |
| Sub 2-13 | m/z = 582.18 ($C_{40}H_{26}N_2OS$ = 582.72) | Sub 2-14 | m/z = 619.21 ($C_{43}H_{29}N_3S$ = 619.79) |
| Sub 2-15 | m/z = 502.20 ($C_{36}H_{26}N_2O$ = 502.62) | Sub 2-16 | m/z = 442.15 ($C_{30}H_{22}N_2S$ = 442.58) |
| Sub 2-17 | m/z = 614.27 ($C_{46}H_{34}N_2$ = 614.79) | Sub 2-18 | m/z = 708.22 ($C_{50}H_{32}N_2OS$ = 708.88) |
| Sub 2-19 | m/z = 442.15 ($C_{30}H_{22}N_2S$ = 442.58) | Sub 2-20 | m/z = 608.19 ($C_{42}H_{28}N_2S$ = 608.76) |
| Sub 2-21 | m/z = 532.16 ($C_{36}H_{24}N_2OS$ = 532.66) | Sub 2-22 | m/z = 707.24 ($C_{50}H_{33}N_3S$ = 707.90) |
| Sub 2-23 | m/z = 354.15 ($C_{24}H_{19}FN_2$ = 354.43) | Sub 2-24 | m/z = 464.20 ($C_{32}H_{24}N_4$ = 464.57) |
| Sub 2-25 | m/z = 618.21 ($C_{44}H_{30}N_2S$ = 618.80) | Sub 2-26 | m/z = 426.17 ($C_{30}H_{22}N_2O$ = 426.52) |
| Sub 2-27 | m/z = 341.19 ($C_{24}H_{15}D_5N_2$ = 341.47) | Sub 2-28 | m/z = 577.25 ($C_{42}H_{31}N_3$ = 577.73) |
| Sub 2-29 | m/z = 528.26 ($C_{39}H_{32}N_2$ = 528.70) | Sub 2-30 | m/z = 532.16 ($C_{36}H_{24}N_2OS$ = 532.66) |

Synthesis Example of Final Products 1

Synthesis Example of P-1

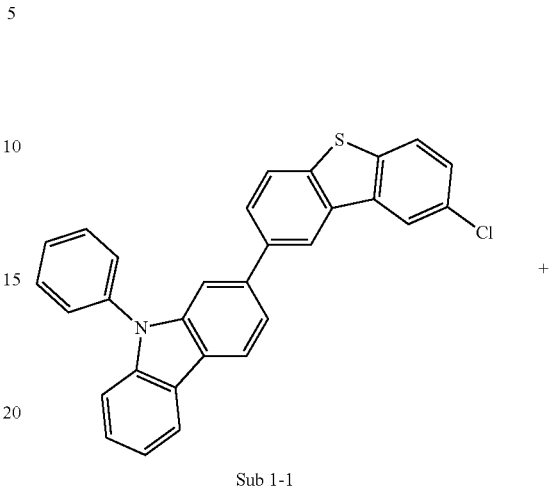

Sub 1-1

+

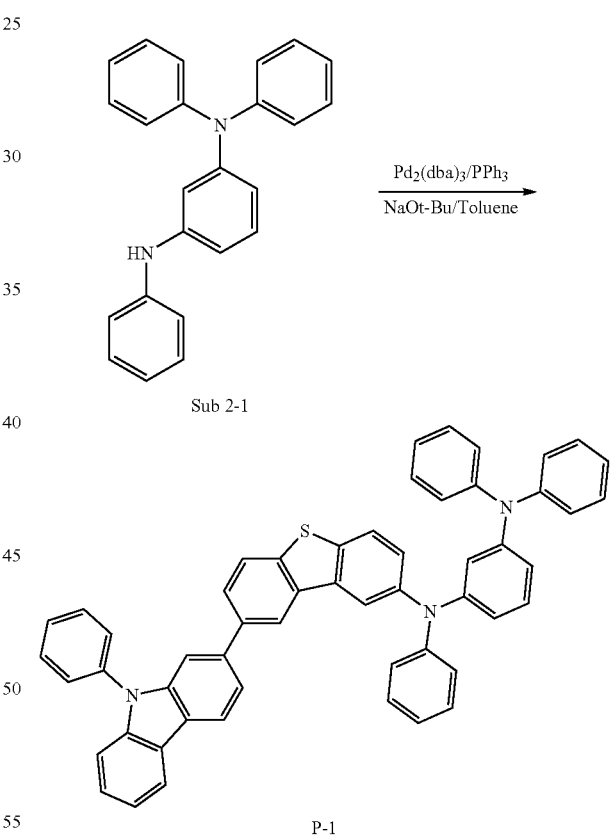

Sub 2-1 (5.85 g, 17.39 mmol) was added to around bottom flask and dissolved in toluene (500 mL), and Sub 1-1 (8.0 g, 17.39 mmol), Pd$_2$(dba)$_3$ (0.48 g, 0.52 mmol), P(t-Bu)$_3$ (0.21 g, 1.04 mmol), NaOt-Bu (5.01 g, 52.18 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 10.8 g of the product. (yield: 81%)

Synthesis Example of P-12
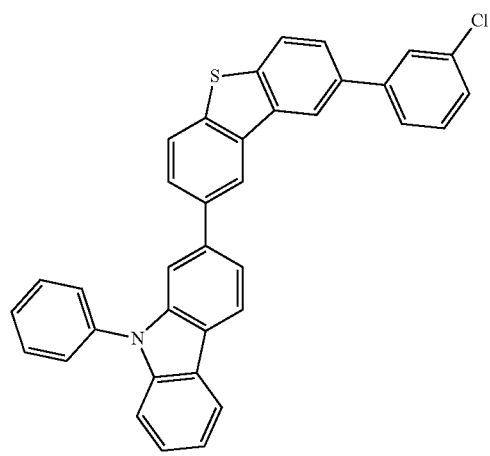
Sub 1-3
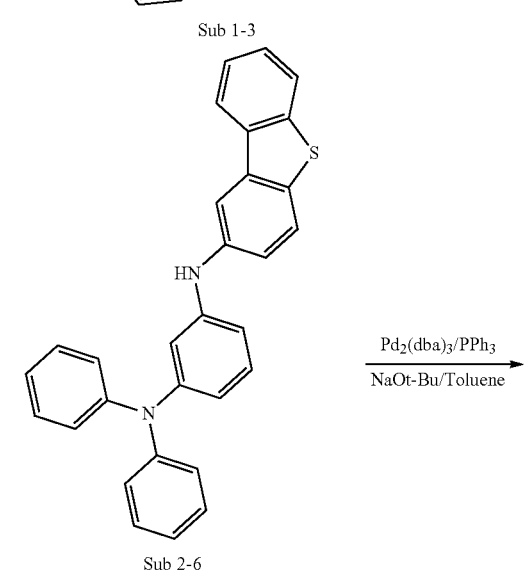
Sub 2-6
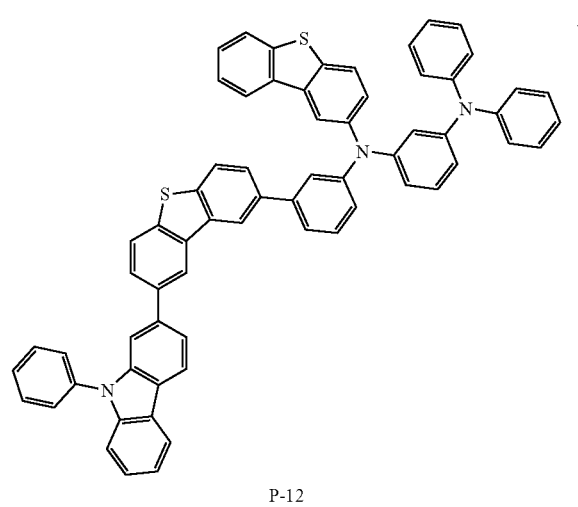
P-12
Sub 1-3 (10.0 g, 18.65 mmol) and Sub 2-6 (8.26 g, 18.65 mmol) were reacted using the synthesis method of Sub 2-I-1 described above to give 14.1 g of the product (yield: 79%).
Synthesis Example of P-34
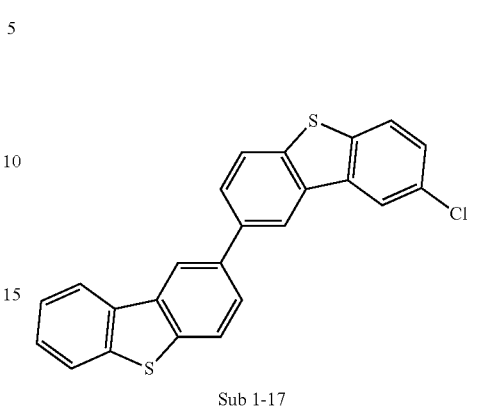
Sub 1-17
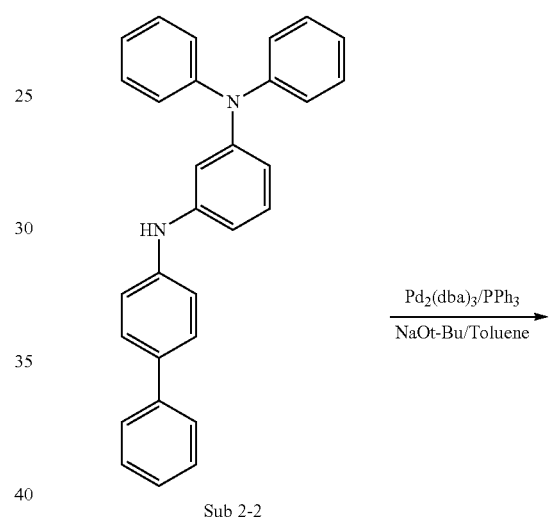
Sub 2-2
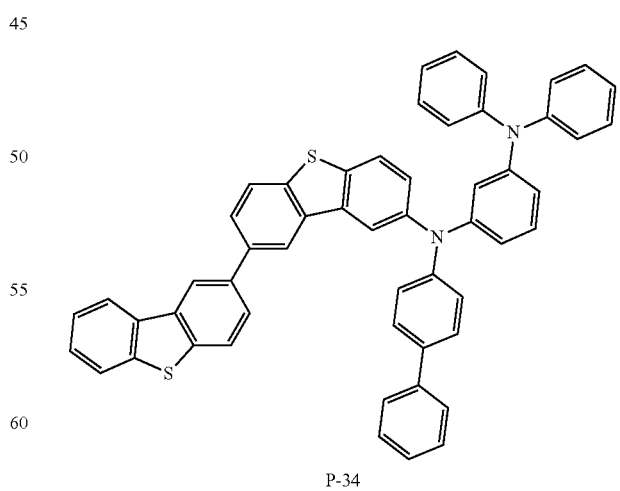
P-34
Sub 1-17 (9.2 g, 22.95 mmol) and Sub 2-2 (9.4 g, 22.95 mmol) were reacted using the synthesis method of Sub 2-I-1 described above to give 14.3 g of the product (yield: 80%).

Synthesis Example of P-76
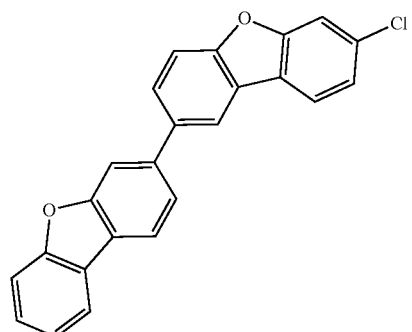
Sub 1-45
+
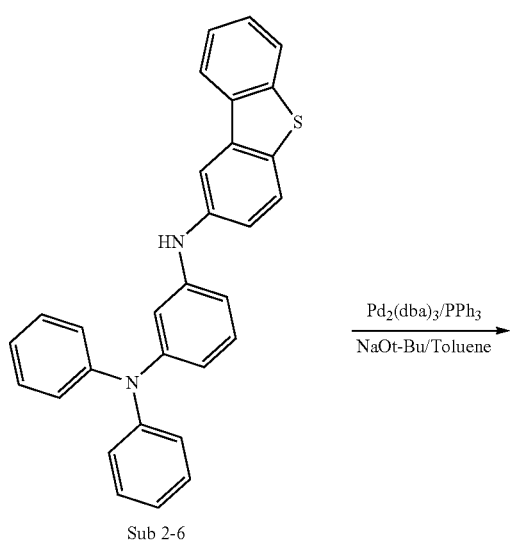
Sub 2-6
→ P-76
Sub 1-45 (8.8 g, 23.86 mmol) and Sub 2-6 (10.56 g, 23.86 mmol) were reacted using the synthesis method of Sub 2-I-1 described above to give 13.1 g of the product (yield: 71%).
Synthesis Example of P-95
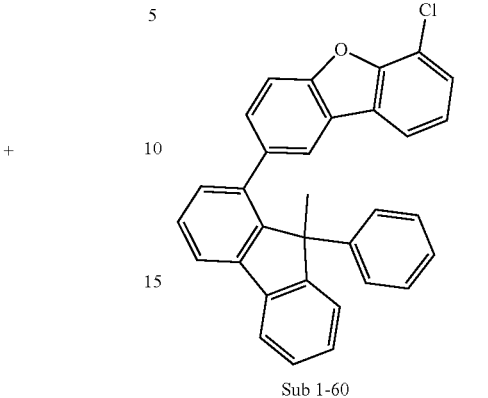
Sub 1-60
+
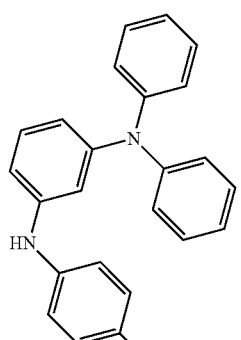
Sub 2-23
→ 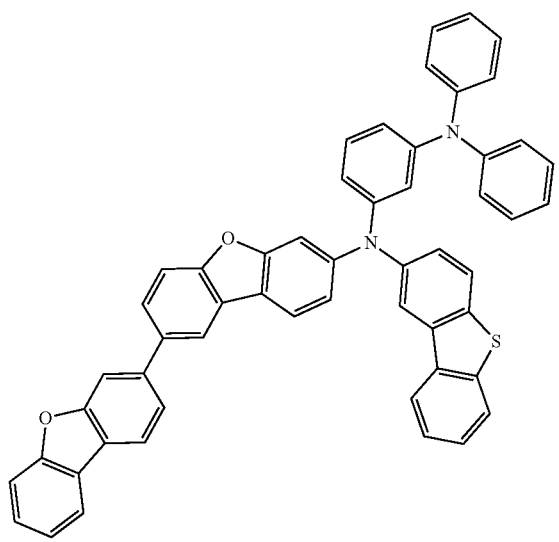
P-95
Sub 1-60 (8.7 g, 19.04 mmol) and Sub 2-23 (6.75 g, 19.04 mmol) were reacted using the synthesis method of Sub 2-I-1 described above to give 13.8 g of the product (yield: 78%).

Synthesis Example of P-105
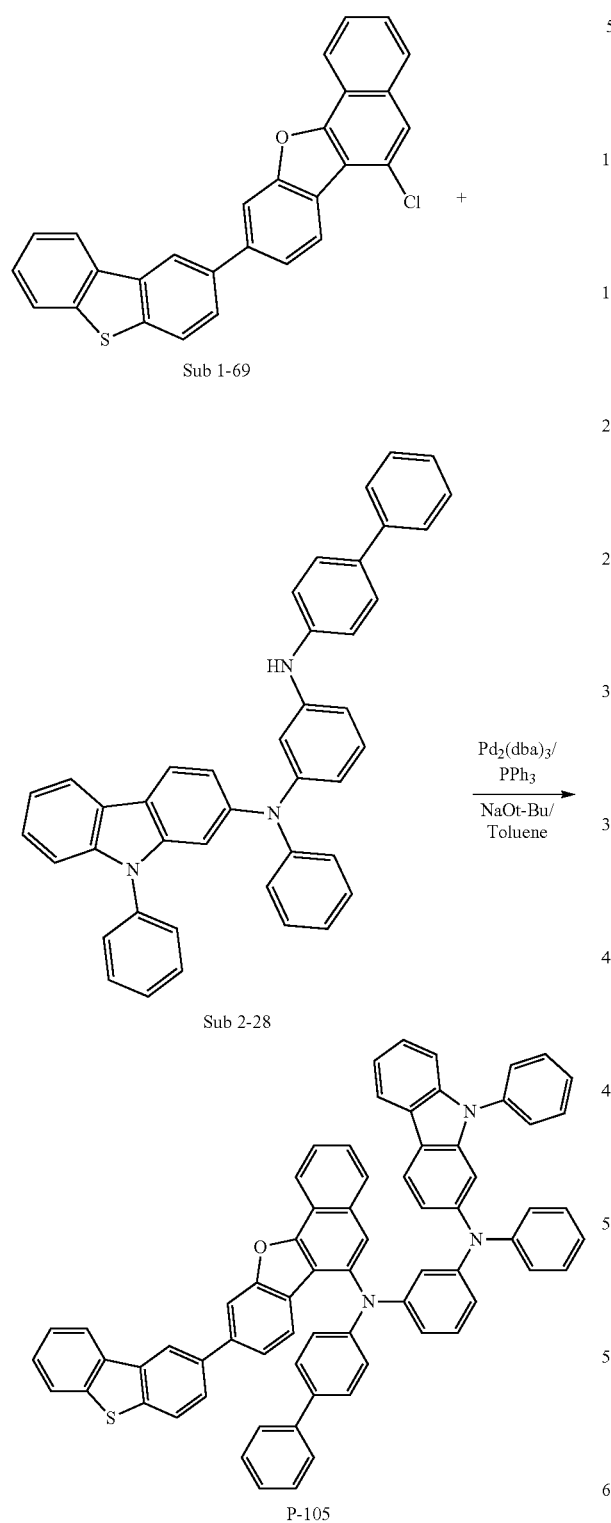
Sub 1-69 (7.9 g, 18.16 mmol) and Sub 2-28 (10.49 g, 18.16 mmol) were reacted using the synthesis method of Sub 2-I-1 described above to give 14.2 g of the product (yield: 80%).
Synthesis Example of P-116
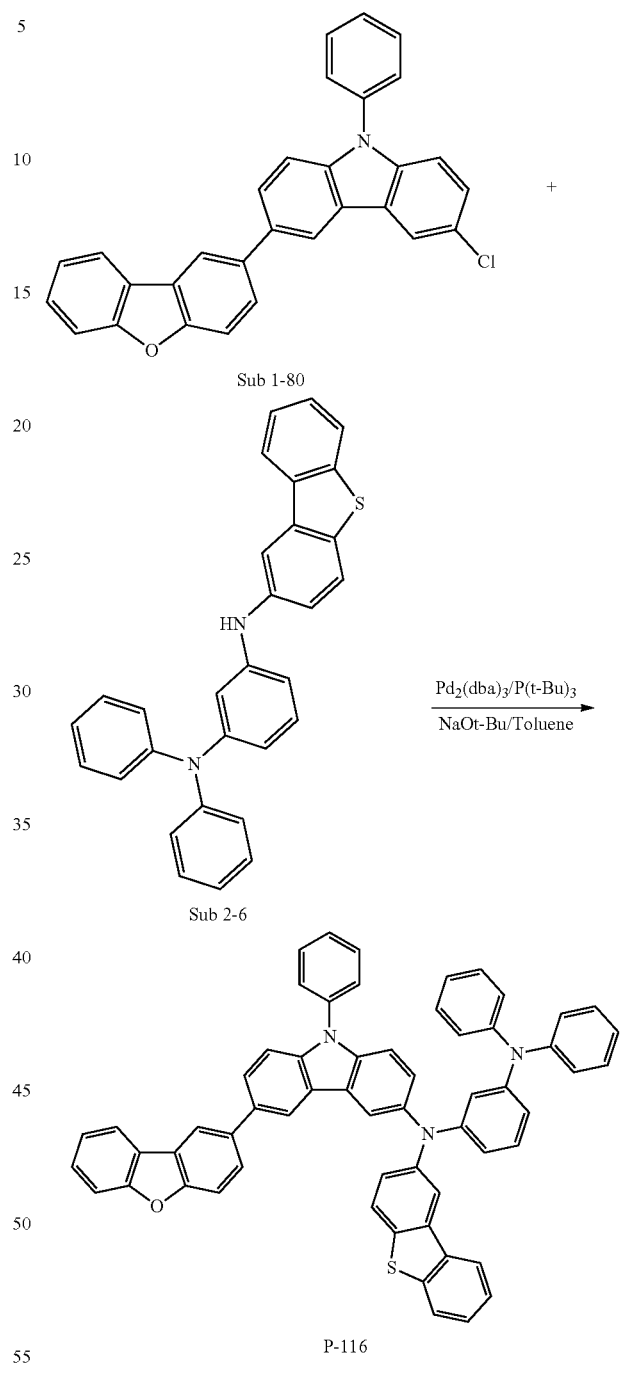
Sub 1-80 (8.9 g, 20.05 mmol) and Sub 2-6 (8.87 g, 20.05 mmol) were reacted using the synthesis method of Sub 2-I-1 described above to give 13.5 g of the product (yield: 79%).
TABLE 3
| compound | FD-MS | compound | FD-MS |
|---|---|---|---|
| P-1 | m/z = 759.27 ($C_{54}H_{37}N_3S$ = 759.97) | P-2 | m/z = 835.30 ($C_{60}H_{41}N_3S$ = 836.07) |

TABLE 3-continued

| compound | FD-MS | compound | FD-MS |
|---|---|---|---|
| P-3 | m/z = 835.30 ($C_{60}H_{41}N_3S$ = 836.07) | P-4 | m/z = 1037.38 ($C_{76}H_{51}N_3S$ = 1038.33) |
| P-5 | m/z = 1101.38 ($C_{80}H_{51}N_3OS$ = 1102.37) | P-6 | m/z = 865.26 ($C_{60}H_{39}N_3S_2$ = 866.11) |
| P-7 | m/z = 1041.32 ($C_{74}H_{47}N_3S_2$ = 1042.33) | P-8 | m/z = 955.27 ($C_{66}H_{41}N_3OS_2$ = 956.19) |
| P-9 | m/z = 911.33 ($C_{66}H_{45}N_3S$ = 912.17) | P-10 | m/z = 1037.38 ($C_{76}H_{51}N_3S$ = 1038.33) |
| P-11 | m/z = 1093.35 ($C_{78}H_{51}N_3S_2$ = 1094.41) | P-12 | m/z = 941.29 ($C_{66}H_{43}N_3OS_2$ = 942.21) |
| P-13 | m/z = 925.31 ($C_{66}H_{43}N_3OS$ = 926.15) | P-14 | m/z = 1005.28 ($C_{70}H_{43}N_3OS_2$ = 1006.25) |
| P-15 | m/z = 759.27 ($C_{54}H_{37}N_3S$ = 759.97) | P-16 | m/z = 835.30 ($C_{60}H_{41}N_3S$ = 836.07) |
| P-17 | m/z = 835.30 ($C_{60}H_{41}N_3S$ = 836.07) | P-18 | m/z = 865.26 ($C_{60}H_{39}N_3S_2$ = 866.11) |
| P-19 | m/z = 776.23 ($C_{54}H_{36}N_2OS_2$ = 777.02) | P-20 | m/z = 790.21 ($C_{54}H_{34}N_2OS_2$ = 791.00) |
| P-21 | m/z = 1037.38 ($C_{76}H_{51}N_3S$ = 1038.33) | P-22 | m/z = 1118.35 ($C_{79}H_{50}N_4S_2$ = 1119.42) |
| P-23 | m/z = 1017.32 ($C_{72}H_{47}N_3OS$ = 1018.31) | P-24 | m/z = 1183.36 ($C_{84}H_{53}N_3OS_2$ = 1184.49) |
| P-25 | m/z = 835.30 ($C_{60}H_{41}N_3S$ = 836.07) | P-26 | m/z = 865.26 ($C_{60}H_{39}N_3S_2$ = 866.11) |
| P-27 | m/z = 1113.41 ($C_{82}H_{55}N_3S$ = 1114.42) | P-28 | m/z = 1207.36 ($C_{86}H_{53}N_3OS_2$ = 1208.51) |
| P-29 | m/z = 835.30 ($C_{60}H_{41}N_3S$ = 836.07) | P-30 | m/z = 865.26 ($C_{60}H_{39}N_3S_2$ = 866.11) |
| P-31 | m/z = 865.26 ($C_{60}H_{39}N_3S_2$ = 866.11) | P-32 | m/z = 1107.33 ($C_{78}H_{49}N_3OS_2$ = 1108.39) |
| P-33 | m/z = 759.27 ($C_{54}H_{37}N_3S$ = 759.97) | P-34 | m/z = 776.23 ($C_{54}H_{36}N_2OS_2$ = 777.02) |
| P-35 | m/z = 790.21 ($C_{54}H_{34}N_2OS_2$ = 791.00) | P-36 | m/z = 896.20 ($C_{60}H_{36}N_4{_2}OS_3$ = 897.14) |
| P-37 | m/z = 806.19 ($C_{54}H_{34}N_2S_3$ = 807.06) | P-38 | m/z = 1157.38 ($C_{83}H_{55}N_3S_2$ = 1158.49) |
| P-39 | m/z = 942.34 ($C_{68}H_{47}FN_2S$ = 943.20) | P-40 | m/z = 1086.38 ($C_{79}H_{50}N_4S$ = 1087.36) |
| P-41 | m/z = 911.33 ($C_{66}H_{45}N_3S$ = 912.17) | P-42 | m/z = 1091.34 ($C_{78}H_{49}N_3OS$ = 1092.39) |
| P-43 | m/z = 1087.40 ($C_{80}H_{53}N_3S$ = 1088.39) | P-44 | m/z = 899.30 ($C_{64}H_{41}N_3OS$ = 900.11) |
| P-45 | m/z = 1147.31 ($C_{80}H_{49}N_3S_3$ = 1148.47) | P-46 | m/z = 865.26 ($C_{60}H_{39}N_3S_2$ = 866.11) |
| P-47 | m/z = 764.30 ($C_{54}H_{32}D_5N_3S$ = N765.00) | P-48 | m/z = 1022.25 ($C_{70}H_{42}N_2OS_{23}$ = 1023.30) |
| P-49 | m/z = 991.31 ($C_{70}H_{45}N_3S_2$ = 992.27) | P-50 | m/z = 1042.34 ($C_{75}H_{50}N_2S_2$ = 1043.36) |
| P-51 | m/z = 1022.25 ($C_{70}H_{42}N_2OS_3$ = 1023.30) | P-52 | m/z = 840.23 ($C_{58}H_{36}N_2OS_2$ = 841.06) |
| P-53 | m/z = 1232.35 ($C_{88}H_{52}N_2S_2O_2$ = 1233.52) | P-54 | m/z = 1118.34 ($C_{80}H_{50}N_2OS_2$ = 1119.41) |
| P-55 | m/z = 1192.35 ($C_{86}H_{52}N_2OS_2$ = 1193.50) | P-56 | m/z = 806.19 ($C_{54}H_{34}N_2S_3$ = 807.06) |
| P-57 | m/z = 743.29 ($C_{54}H_{37}N_3O$ = 743.91) | P-58 | m/z = 819.32 ($C_{60}H_{41}N_3O$ = 820.01) |
| P-59 | m/z = 819.32 ($C_{60}H_{41}N_3O$ = 820.01) | P-60 | m/z = 1021.40 ($C_{76}H_{51}N_3O$ = 1022.26) |
| P-61 | m/z = 1085.40 ($C_{80}H_{51}N_3O_2$ = 1086.31) | P-62 | m/z = 849.28 ($C_{60}H_{39}N_3OS$ = 850.05) |
| P-63 | m/z = 1025.34 ($C_{74}H_{47}N_3OS$ = 1026.27) | P-64 | m/z = 939.29 ($C_{66}H_{41}N_3O_2S$ = 940.13) |
| P-65 | m/z = 895.35 ($C_{66}H_{45}N_3O$ = 896.21) | P-66 | m/z = 1021.40 ($C_{76}H_{51}N_3O$ = 1022.26) |
| P-67 | m/z = 1077.37 ($C_{78}H_{51}N_3OS$ = 1078.35) | P-68 | m/z = 925.31 ($C_{66}H_{43}N_3OS$ = 926.15) |
| P-69 | m/z = 909.33 ($C_{66}H_{43}N_3O_2$ = 910.09) | P-70 | m/z = 989.30 ($C_{70}H_{43}N_3O_2S$ = 990.19) |
| P-71 | m/z = 743.29 ($C_{54}H_{37}N_3O$ = 743.91) | P-72 | m/z = 819.32 ($C_{60}H_{41}N_3O$ = 820.01) |
| P-73 | m/z = 819.32 ($C_{60}H_{41}N_3O$ = 820.01) | P-74 | m/z = 849.28 ($C_{60}H_{39}N_3OS$ = 850.05) |
| P-75 | m/z = 760.25 ($C_{54}H_{36}N_2OS$ = 760.96) | P-76 | m/z = 774.23 ($C_{54}H_{34}N_2O_2S$ = 774.94) |
| P-77 | m/z = 1021.40 ($C_{76}H_{51}N_3O$ = 1022.26) | P-78 | m/z = 1102.37 ($C_{79}H_{50}N_4OS$ = 1103.36) |
| P-79 | m/z = 1001.34 ($C_{72}H_{47}N_3OS$ = 1002.25) | P-80 | m/z = 1167.38 ($C_{84}H_{53}N_3O_2S$ = 1168.43) |
| P-81 | m/z = 819.32 ($C_{60}H_{41}N_3O$ = 820.01) | P-82 | m/z = 849.28 ($C_{60}H_{39}N_3OS$ = 850.05) |
| P-83 | m/z = 1097.43 ($C_{82}H_{55}N_3O$ = 1098.36) | P-84 | m/z = 1191.38 ($C_{86}H_{53}N_3O_2S$ = 1192.45) |
| P-85 | m/z = 819.32 ($C_{60}H_{41}N_3O$ = 820.01) | P-86 | m/z = 849.28 ($C_{60}H_{39}N_3OS$ = 850.05) |
| P-87 | m/z = 849.28 ($C_{60}H_{39}N_3OS$ = 850.05) | P-88 | m/z = 1091.35 ($C_{78}H_{49}N_3OS_2$ = 1092.33) |
| P-89 | m/z = 743.29 ($C_{54}H_{37}N_3O$ = 743.91) | P-90 | m/z = 760.25 ($C_{54}H_{36}N_2OS$ = 760.96) |
| P-91 | m/z = 774.23 ($C_{54}H_{34}N_2O_2S$ = 774.94) | P-92 | m/z = 880.22 ($C_{60}H_{36}N_2O_2S_2$ = 881.08) |
| P-93 | m/z = 790.21 ($C_{54}H_{34}N_2O_2S_2$ = 791.00) | P-94 | m/z = 1141.41 ($C_{83}H_{55}N_3OS$ = 1029.32) |
| P-95 | m/z = 926.36 ($C_{68}H_{47}FN_2O$ = 927.14) | P-96 | m/z = 928.2 ($C_{68}H_{40}N_4O$ = 929.10) |
| P-97 | m/z = 895.35 ($C_{66}H_{45}N_3O$ = 896.21) | P-98 | m/z = 1075.36 ($C_{78}H_{49}N_3OS$ = 1076.33) |
| P-99 | m/z = 1071.42 ($C_{80}H_{53}N_3O$ = 1072.33) | P-100 | m/z = 883.32 ($C_{64}H_{41}N_3O_2$ = 884.05) |
| P-101 | m/z = 1131.33 ($C_{80}H_{49}N_3O_2S_2$ = 1132.41) | P-102 | m/z = 849.28 ($C_{60}H_{39}N_3OS$ = 850.05) |
| P-103 | m/z = 748.32 ($C_{54}H_{32}D_5N_3O$ = 748.94) | P-104 | m/z = 1006.27 ($C_{70}H_{42}N_2O_2S_2$ = 1007.24) |
| P-105 | m/z = 975.33 ($C_{70}H_{45}N_3OS$ = 976.21) | P-106 | m/z = 1026.36 ($C_{75}H_{50}N_2OS$ = 1027.30) |
| P-107 | m/z = 1006.27 ($C_{70}H_{42}N_2O_2S_2$ = 1007.24) | P-108 | m/z = 824.25 ($C_{58}H_{36}N_2O_2S$ = 825.00) |
| P-109 | m/z = 1216.37 ($C_{88}H_{52}N_2O_3S$ = 1217.46) | P-110 | m/z = 1102.36 ($C_{80}H_{50}N_2O_2S$ = 1103.35) |
| P-111 | m/z = 1176.37 ($C_{86}H_{52}N_2O_2S$ = 1177.44) | P-112 | m/z-790.21 ($C_{54}H_{34}N_2OS_2$ = 791.00) |
| P-113 | m/z = 894.37 ($C_{66}H_{46}N_4$ = 895.12) | P-114 | m/z = 894.37 ($C_{66}H_{46}N_4$ = 895.12) |
| P-115 | m/z = 835.30 ($C_{60}H_{41}N_3S$ = 836.07) | P-116 | m/z = 849.28 ($C_{60}H_{39}N_3OS$ = 850.05) |
| P-117 | m/z = 865.26 ($C_{60}H_{39}N_3S_2$ = 866.11) | P-118 | m/z = 1100.39 ($C_{80}H_{52}N_4S$ = 1101.38) |
| P-119 | m/z = 894.37 ($C_{66}H_{46}N_4$ = 895.12) | P-120 | m/z = 1005.28 ($C_{70}H_{43}N_3OS_2$ = 1006.25) |
| P-121 | m/z = 845.38 ($C_{63}H_{47}N_3$ = 846.09) | P-122 | m/z = 907.39 ($C_{68}H_{49}N_3$ = 908.16) |
| P-123 | m/z = 910.34 ($C_{67}H_{46}N_2S$ = 911.18) | P-124 | m/z = 922.30 ($C_{67}H_{42}N_2OS$ = 923.15) |
| P-125 | m/z = 928.29 ($C_{66}H_{44}N_2S_2$ = 929.21) | P-126 | m/z = 1063.40 ($C_{78}H_{53}N_3S$ = 1064.36) |
| P-127 | m/z = 1019.42 ($C_{77}H_{53}N_3$ = 1020.29) | P-128 | m/z = 1078.31 ($C_{77}H_{46}N_2OS_2$ = 1079.35) |

Manufacture and Evaluation of Organic Electric Element

Example 1) Manufacture and Testing of a Red Organic Light Emitting Diode

First, on an ITO layer(anode) formed on a glass substrate, $N^1$-(naphthalen-2-yl)-$N^4$,$N^4$-bis(4-(naphthalen-2-yl(phenyl)amino)phenyl)-N-phenyl benzene-1,4-diamine (hereinafter will be abbreviated as 2-TNATA) was vacuum-deposited to form a hole injection layer with a thickness of 60 nm, and N,N'-bis(1-naphthalenyl)-N,N'-bis-phenyl-(1,1'-biphenyl)-4,4'-diamine (hereinafter will be abbreviated as NPB) was vacuum-deposited to form a hole transport layer with a thickness of 60 nm. Subsequently, the inventive compound represented by Formula (1) was vacuum-deposited as an emitting-auxiliary layer material to a thickness of 20 nm to form an emitting-auxiliary layer. After forming the emitting-auxiliary layer, CBP [4,4'-N, N-dicarbazole-biphenyl] as a host was used in the upper of an emitting auxiliary layer, and (piq)$_2$Ir(acac) [bis-(1-phenylisoquinolyl)iridium(III) acetylacetonate] as a dopant was vacuum deposited to form an emitting layer with a thickness of 30 nm by doping with a weight ratio of 95:5. (1,1'-biphenyl)-4-olato)bis(2-methyl-8-quinolinolato)aluminum (hereinafter will be abbreviated as BAlq) was vacuum-deposited to a thickness of 10 nm as a hole blocking layer, and tris(8-quinolinol)aluminum (hereinafter will be abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 500 cd/m$^2$. In the following table, the manufacture of a device and the results of evaluation are shown.

Comparative 1

An organic electroluminescent device was manufactured in the same manner as in Example 1, except that the emitting-auxiliary layer was not used.

Comparative Examples 2 to 5

An organic electroluminescent device was manufactured in the same manner as in Example 1, except that Comparative Compounds A to D were used as the emitting-auxiliary layer material.

Comparative Compound A

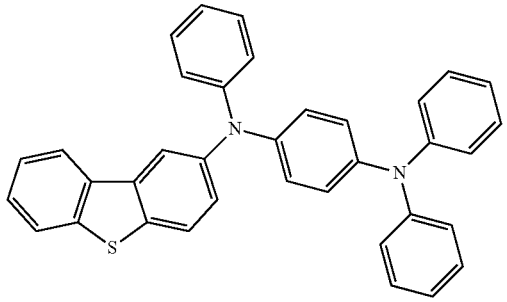

Comparative Compound B

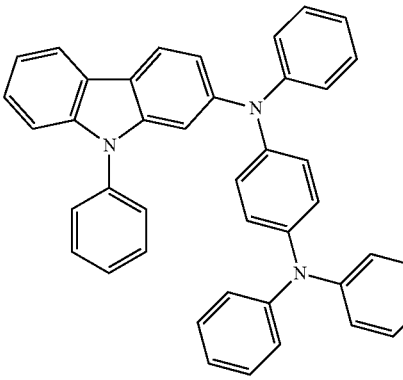

Comparative Compound C

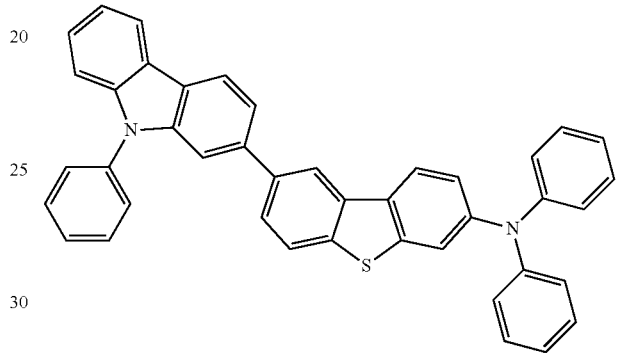

Comparative Compound D

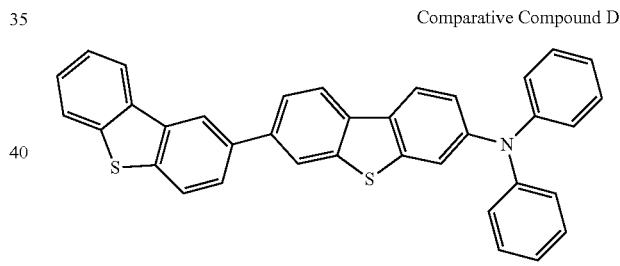

TABLE 4

| | compound | Voltage | Current Density | Brightness (cd/m$^2$) | Efficiency | Lifetime T(95) | CIE (x, y) |
|---|---|---|---|---|---|---|---|
| comparative example(1) | — | 6.0 | 32.9 | 2500.0 | 7.6 | 61.8 | (0.66, 0.32) |
| comparative example(2) | comparative compound A | 5.9 | 24.3 | 2500.0 | 10.3 | 88.7 | (0.67, 0.32) |
| comparative example(3) | comparative compound B | 5.7 | 19.8 | 2500.0 | 12.6 | 90.1 | (0.66, 0.35) |
| comparative example(4) | comparative compound C | 5.3 | 15.5 | 2500.0 | 16.1 | 104.3 | (0.66, 0.35) |
| comparative example(5) | comparative compound D | 5.5 | 17.1 | 2500.0 | 14.6 | 92.9 | (0.67, 0.32) |
| example(1) | compound(P-1) | 4.5 | 8.9 | 2500.0 | 28.0 | 124.9 | (0.66, 0.32) |
| example(2) | compound(P-2) | 4.2 | 7.6 | 2500.0 | 32.8 | 123.7 | (0.66, 0.35) |
| example(3) | compound(P-3) | 4.4 | 8.5 | 2500.0 | 29.5 | 124.0 | (0.66, 0.35) |
| example(4) | compound(P-4) | 4.5 | 8.6 | 2500.0 | 29.2 | 119.2 | (0.65, 0.35) |
| example(5) | compound(P-5) | 4.4 | 8.8 | 2500.0 | 28.3 | 124.9 | (0.65, 0.35) |
| example(6) | compound(P-6) | 4.5 | 8.9 | 2500.0 | 28.2 | 120.2 | (0.66, 0.35) |
| example(7) | compound(P-7) | 4.5 | 8.4 | 2500.0 | 29.8 | 122.2 | (0.66, 0.35) |
| example(8) | compound(P-8) | 4.5 | 8.6 | 2500.0 | 29.1 | 124.6 | (0.66, 0.35) |
| example(9) | compound(P-9) | 4.4 | 8.8 | 2500.0 | 28.5 | 123.2 | (0.66, 0.35) |
| example(10) | compound(P-10) | 4.4 | 8.6 | 2500.0 | 29.2 | 124.9 | (0.66, 0.35) |

TABLE 4-continued

| | compound | Voltage | Current Density | Brightness (cd/m$^2$) | Efficiency | Lifetime T(95) | CIE (x, y) |
|---|---|---|---|---|---|---|---|
| example(11) | compound(P-11) | 4.4 | 8.8 | 2500.0 | 28.3 | 123.8 | (0.66, 0.35) |
| example(12) | compound(P-12) | 4.4 | 8.7 | 2500.0 | 28.8 | 120.9 | (0.66, 0.35) |
| example(13) | compound(P-13) | 4.4 | 8.4 | 2500.0 | 29.8 | 120.6 | (0.66, 0.35) |
| example(14) | compound(P-14) | 4.5 | 8.4 | 2500.0 | 29.9 | 121.3 | (0.66, 0.35) |
| example(15) | compound(P-15) | 4.5 | 8.4 | 2500.0 | 29.6 | 123.5 | (0.66, 0.35) |
| example(16) | compound(P-16) | 4.4 | 8.7 | 2500.0 | 28.6 | 121.6 | (0.66, 0.35) |
| example(17) | compound(P-17) | 4.4 | 8.4 | 2500.0 | 29.6 | 124.7 | (0.66, 0.35) |
| example(18) | compound(P-18) | 4.4 | 8.4 | 2500.0 | 29.6 | 123.3 | (0.66, 0.35) |
| example(19) | compound(P-19) | 4.5 | 9.5 | 2500.0 | 26.3 | 122.7 | (0.66, 0.35) |
| example(20) | compound(P-20) | 4.5 | 8.9 | 2500.0 | 28.0 | 122.7 | (0.66, 0.35) |
| example(21) | compound(P-21) | 4.4 | 8.8 | 2500.0 | 28.3 | 124.0 | (0.66, 0.35) |
| example(22) | compound(P-22) | 4.4 | 8.5 | 2500.0 | 29.4 | 121.7 | (0.66, 0.35) |
| example(23) | compound(P-23) | 4.4 | 8.7 | 2500.0 | 28.9 | 121.0 | (0.66, 0.35) |
| example(24) | compound(P-24) | 4.5 | 8.6 | 2500.0 | 29.1 | 123.9 | (0.66, 0.35) |
| example(25) | compound(P-25) | 4.5 | 8.8 | 2500.0 | 28.4 | 123.8 | (0.66, 0.35) |
| example(26) | compound(P-26) | 4.4 | 8.6 | 2500.0 | 29.0 | 119.6 | (0.66, 0.35) |
| example(27) | compound(P-27) | 4.4 | 8.5 | 2500.0 | 29.5 | 120.2 | (0.66, 0.35) |
| example(28) | compound(P-28) | 4.4 | 8.4 | 2500.0 | 29.9 | 122.7 | (0.66, 0.35) |
| example(29) | compound(P-29) | 4.4 | 8.6 | 2500.0 | 29.2 | 123.3 | (0.66, 0.35) |
| example(30) | compound(P-30) | 4.5 | 8.7 | 2500.0 | 28.9 | 121.3 | (0.66, 0.35) |
| example(31) | compound(P-31) | 4.4 | 8.8 | 2500.0 | 28.4 | 124.3 | (0.66, 0.35) |
| example(32) | compound(P-32) | 4.5 | 8.9 | 2500.0 | 28.2 | 124.8 | (0.66, 0.35) |
| example(33) | compound(P-33) | 4.4 | 8.7 | 2500.0 | 28.9 | 123.5 | (0.66, 0.35) |
| example(34) | compound(P-34) | 4.6 | 9.5 | 2500.0 | 26.3 | 122.2 | (0.66, 0.35) |
| example(35) | compound(P-35) | 4.6 | 9.3 | 2500.0 | 26.9 | 119.9 | (0.66, 0.35) |
| example(36) | compound(P-36) | 4.6 | 9.0 | 2500.0 | 27.7 | 119.2 | (0.66, 0.35) |
| example(37) | compound(P-37) | 4.5 | 9.4 | 2500.0 | 26.6 | 122.7 | (0.66, 0.35) |
| example(38) | compound(P-38) | 4.9 | 12.6 | 2500.0 | 19.9 | 114.4 | (0.66, 0.35) |
| example(39) | compound(P-39) | 4.9 | 13.2 | 2500.0 | 18.9 | 114.1 | (0.66, 0.35) |
| example(40) | compound(P-40) | 4.9 | 13.7 | 2500.0 | 18.3 | 110.0 | (0.66, 0.35) |
| example(41) | compound(P-41) | 4.4 | 8.6 | 2500.0 | 29.0 | 123.5 | (0.66, 0.35) |
| example(42) | compound(P-42) | 4.5 | 8.7 | 2500.0 | 28.7 | 120.3 | (0.66, 0.35) |
| example(43) | compound(P-43) | 4.4 | 8.6 | 2500.0 | 29.2 | 124.7 | (0.66, 0.35) |
| example(44) | compound(P-44) | 4.4 | 8.5 | 2500.0 | 29.4 | 123.9 | (0.66, 0.35) |
| example(45) | compound(P-45) | 4.4 | 8.6 | 2500.0 | 29.0 | 124.5 | (0.66, 0.35) |
| example(46) | compound(P-46) | 4.4 | 8.7 | 2500.0 | 28.7 | 119.3 | (0.66, 0.35) |
| example(47) | compound(P-47) | 4.4 | 8.4 | 2500.0 | 29.8 | 120.1 | (0.66, 0.32) |
| example(48) | compound(P-48) | 4.5 | 9.3 | 2500.0 | 26.9 | 122.3 | (0.67, 0.32) |
| example(49) | compound(P-49) | 4.5 | 9.3 | 2500.0 | 26.8 | 123.6 | (0.66, 0.32) |
| example(50) | compound(P-50) | 4.5 | 9.3 | 2500.0 | 27.0 | 125.0 | (0.66, 0.32) |
| example(51) | compound(P-51) | 4.5 | 9.5 | 2500.0 | 26.3 | 122.5 | (0.66, 0.35) |
| example(52) | compound(P-52) | 4.6 | 9.5 | 2500.0 | 26.4 | 122.2 | (0.65, 0.35) |
| example(53) | compound(P-53) | 4.5 | 9.5 | 2500.0 | 26.3 | 120.9 | (0.65, 0.35) |
| example(54) | compound(P-54) | 4.5 | 9.2 | 2500.0 | 27.2 | 121.7 | (0.66, 0.32) |
| example(55) | compound(P-55) | 4.6 | 9.2 | 2500.0 | 27.2 | 124.9 | (0.67, 0.32) |
| example(56) | compound(P-56) | 4.6 | 9.0 | 2500.0 | 27.9 | 119.1 | (0.66, 0.35) |
| example(57) | compound(P-57) | 4.7 | 11.3 | 2500.0 | 22.1 | 117.2 | (0.66, 0.35) |
| example(58) | compound(P-58) | 4.7 | 11.2 | 2500.0 | 22.4 | 116.2 | (0.66, 0.32) |
| example(59) | compound(P-59) | 4.7 | 10.6 | 2500.0 | 23.6 | 116.4 | (0.66, 0.35) |
| example(60) | compound(P-60) | 4.8 | 11.1 | 2500.0 | 22.5 | 117.1 | (0.66, 0.35) |
| example(61) | compound(P-61) | 4.7 | 11.3 | 2500.0 | 22.2 | 117.4 | (0.65, 0.35) |
| example(62) | compound(P-62) | 4.8 | 10.8 | 2500.0 | 23.2 | 115.1 | (0.65, 0.35) |
| example(63) | compound(P-63) | 4.7 | 10.9 | 2500.0 | 23.0 | 116.3 | (0.66, 0.35) |
| example(64) | compound(P-64) | 4.7 | 10.8 | 2500.0 | 23.1 | 116.6 | (0.66, 0.35) |
| example(65) | compound(P-65) | 4.7 | 11.0 | 2500.0 | 22.8 | 117.9 | (0.66, 0.35) |
| example(66) | compound(P-66) | 4.7 | 10.6 | 2500.0 | 23.7 | 117.5 | (0.66, 0.35) |
| example(67) | compound(P-67) | 4.8 | 10.6 | 2500.0 | 23.6 | 115.1 | (0.66, 0.35) |
| example(68) | compound(P-68) | 4.7 | 11.4 | 2500.0 | 22.0 | 116.4 | (0.66, 0.35) |
| example(69) | compound(P-69) | 4.8 | 11.3 | 2500.0 | 22.2 | 117.4 | (0.66, 0.35) |
| example(70) | compound(P-70) | 4.8 | 10.9 | 2500.0 | 22.9 | 117.0 | (0.66, 0.35) |
| example(71) | compound(P-71) | 4.7 | 11.1 | 2500.0 | 22.5 | 115.4 | (0.66, 0.35) |
| example(72) | compound(P-72) | 4.8 | 10.9 | 2500.0 | 23.0 | 116.8 | (0.66, 0.35) |
| example(73) | compound(P-73) | 4.8 | 11.0 | 2500.0 | 22.8 | 117.3 | (0.66, 0.35) |
| example(74) | compound(P-74) | 4.8 | 11.0 | 2500.0 | 22.7 | 117.2 | (0.66, 0.35) |
| example(75) | compound(P-75) | 4.5 | 9.4 | 2500.0 | 26.7 | 124.9 | (0.66, 0.35) |
| example(76) | compound(P-76) | 4.5 | 9.2 | 2500.0 | 27.3 | 119.5 | (0.66, 0.35) |
| example(77) | compound(P-77) | 4.7 | 11.2 | 2500.0 | 22.3 | 117.2 | (0.66, 0.32) |
| example(78) | compound(P-78) | 4.8 | 10.7 | 2500.0 | 23.3 | 115.3 | (0.66, 0.35) |
| example(79) | compound(P-79) | 4.8 | 10.7 | 2500.0 | 23.3 | 115.3 | (0.66, 0.35) |
| example(80) | compound(P-80) | 4.7 | 10.8 | 2500.0 | 23.2 | 116.5 | (0.65, 0.35) |
| example(81) | compound(P-81) | 4.7 | 11.1 | 2500.0 | 22.5 | 116.1 | (0.65, 0.35) |
| example(82) | compound(P-82) | 4.7 | 10.6 | 2500.0 | 23.6 | 116.2 | (0.66, 0.35) |
| example(83) | compound(P-83) | 4.7 | 10.7 | 2500.0 | 23.5 | 116.2 | (0.66, 0.35) |
| example(84) | compound(P-84) | 4.8 | 11.2 | 2500.0 | 22.4 | 116.4 | (0.66, 0.35) |
| example(85) | compound(P-85) | 4.8 | 10.6 | 2500.0 | 23.7 | 117.4 | (0.66, 0.35) |
| example(86) | compound(P-86) | 4.7 | 11.1 | 2500.0 | 22.6 | 117.9 | (0.66, 0.35) |
| example(87) | compound(P-87) | 4.7 | 10.5 | 2500.0 | 23.8 | 116.8 | (0.66, 0.35) |

TABLE 4-continued

| compound | | Voltage | Current Density | Brightness (cd/m²) | Efficiency | Lifetime T(95) | CIE (x, y) |
|---|---|---|---|---|---|---|---|
| example(88) | compound(P-88) | 4.7 | 11.0 | 2500.0 | 22.8 | 116.8 | (0.66, 0.35) |
| example(89) | compound(P-89) | 4.8 | 10.8 | 2500.0 | 23.1 | 117.2 | (0.66, 0.35) |
| example(90) | compound(P-90) | 4.6 | 9.6 | 2500.0 | 26.1 | 120.4 | (0.66, 0.35) |
| example(91) | compound(P-91) | 4.6 | 9.4 | 2500.0 | 26.5 | 119.7 | (0.66, 0.35) |
| example(92) | compound(P-92) | 4.6 | 8.9 | 2500.0 | 28.0 | 119.3 | (0.66, 0.35) |
| example(93) | compound(P-93) | 4.5 | 9.0 | 2500.0 | 27.8 | 120.6 | (0.66, 0.35) |
| example(94) | compound(P-94) | 4.9 | 13.9 | 2500.0 | 18.0 | 112.9 | (0.66, 0.35) |
| example(95) | compound(P-95) | 4.9 | 12.8 | 2500.0 | 19.6 | 113.7 | (0.66, 0.35) |
| example(96) | compound(P-96) | 4.9 | 13.4 | 2500.0 | 18.6 | 112.0 | (0.66, 0.35) |
| example(97) | compound(P-97) | 4.7 | 10.8 | 2500.0 | 23.2 | 115.7 | (0.66, 0.35) |
| example(98) | compound(P-98) | 4.8 | 11.0 | 2500.0 | 22.7 | 117.9 | (0.66, 0.35) |
| example(99) | compound(P-99) | 4.8 | 11.0 | 2500.0 | 22.7 | 117.8 | (0.66, 0.35) |
| example(100) | compound(P-100) | 4.7 | 10.5 | 2500.0 | 23.7 | 115.0 | (0.66, 0.35) |
| example(101) | compound(P-101) | 4.7 | 10.5 | 2500.0 | 23.8 | 115.7 | (0.66, 0.35) |
| example(102) | compound(P-102) | 4.7 | 10.8 | 2500.0 | 23.2 | 115.4 | (0.66, 0.35) |
| example(103) | compound(P-103) | 4.8 | 11.4 | 2500.0 | 22.0 | 116.1 | (0.66, 0.35) |
| example(104) | compound(P-104) | 4.5 | 9.2 | 2500.0 | 27.2 | 122.7 | (0.66, 0.35) |
| example(105) | compound(P-105) | 4.5 | 9.6 | 2500.0 | 26.1 | 119.8 | (0.66, 0.35) |
| example(106) | compound(P-106) | 4.5 | 9.2 | 2500.0 | 27.1 | 121.8 | (0.66, 0.35) |
| example(107) | compound(P-107) | 4.5 | 9.6 | 2500.0 | 26.1 | 121.2 | (0.66, 0.35) |
| example(108) | compound(P-108) | 4.6 | 9.1 | 2500.0 | 27.6 | 123.4 | (0.66, 0.35) |
| example(109) | compound(P-109) | 4.6 | 9.6 | 2500.0 | 26.1 | 124.7 | (0.66, 0.35) |
| example(110) | compound(P-110) | 4.6 | 9.6 | 2500.0 | 26.1 | 118.5 | (0.66, 0.35) |
| example(111) | compound(P-111) | 4.5 | 9.2 | 2500.0 | 27.3 | 121.8 | (0.66, 0.35) |
| example(112) | compound(P-112) | 4.5 | 9.6 | 2500.0 | 26.1 | 121.0 | (0.66, 0.35) |
| example(113) | compound(P-113) | 4.9 | 11.7 | 2500.0 | 21.4 | 116.5 | (0.66, 0.35) |
| example(114) | compound(P-114) | 4.9 | 12.4 | 2500.0 | 20.2 | 117.4 | (0.66, 0.35) |
| example(115) | compound(P-115) | 4.6 | 10.3 | 2500.0 | 24.3 | 117.0 | (0.66, 0.35) |
| example(116) | compound(P-116) | 4.7 | 10.4 | 2500.0 | 24.2 | 116.8 | (0.66, 0.35) |
| example(117) | compound(P-117) | 4.7 | 9.7 | 2500.0 | 25.8 | 116.0 | (0.66, 0.35) |
| example(118) | compound(P-118) | 4.8 | 12.3 | 2500.0 | 20.3 | 115.7 | (0.66, 0.35) |
| example(119) | compound(P-119) | 4.9 | 11.6 | 2500.0 | 21.6 | 117.8 | (0.66, 0.35) |
| example(120) | compound(P-120) | 4.7 | 10.4 | 2500.0 | 24.1 | 112.7 | (0.66, 0.35) |
| example(121) | compound(P-121) | 5.0 | 13.8 | 2500.0 | 18.2 | 111.4 | (0.66, 0.35) |
| example(122) | compound(P-122) | 5.0 | 12.6 | 2500.0 | 19.9 | 113.6 | (0.66, 0.35) |
| example(123) | compound(P-123) | 4.9 | 13.8 | 2500.0 | 18.1 | 110.3 | (0.66, 0.32) |
| example(124) | compound(P-124) | 5.0 | 13.4 | 2500.0 | 18.7 | 111.0 | (0.67, 0.32) |
| example(125) | compound(P-125) | 4.9 | 13.0 | 2500.0 | 19.3 | 110.8 | (0.66, 0.32) |
| example(126) | compound(P-126) | 5.0 | 13.1 | 2500.0 | 19.1 | 110.5 | (0.66, 0.35) |
| example(127) | compound(P-127) | 4.9 | 12.7 | 2500.0 | 19.6 | 112.2 | (0.66, 0.35) |
| example(128) | compound(P-128) | 4.9 | 13.0 | 2500.0 | 19.2 | 111.4 | (0.65, 0.35) |

As it is apparent from the results of Table 4, when a red organic electroluminescent device is manufactured using the material for an organic electric element of the present invention as an emitting-auxiliary layer material, the driving voltage and life span can be remarkably improved as compared with the comparative examples not using the emitting-auxiliary layer or using the comparative compounds A to D.

In other words, the results of Comparative Examples 2 to 5 using the comparative compounds A to D were superior to those of Comparative Example 1 not using the emitting-auxiliary layer, and Examples 1 to 128 of the compound of the present invention in which specific substituents were further added to the comparative compounds showed the best results.

Comparing the results of the inventive compounds with the comparative compounds A and B, the inventive compound is a compound in which specific substituents such as dibenzothiophen or cabazole or dibenzofuran or fluorene are further substituted as secondary substituents to dibenzothiophen or cabazole of the comparative compounds A and B, and as the specific substituent is further added, the physical properties of compounds such as hole characteristics, light efficiency characteristics, energy levels (LUMO and HOMO levels), hole injection and mobility characteristics, and electron blocking characteristics are changed. Therefore, it is confirmed that these different results are obtained because they act as a main factor in improving the device performance (in particular, the efficiency improvement) in the device deposition.

Comparing the results of the inventive compounds with the comparative compounds C and D, the inventive compound is a compound in which one additional amine group is added as a secondary substituent to the comparative compounds C and D. As the amine groups are added, the hole properties are improved and the hole injection and mobility ability are improved, as a result, it can be confirmed that these different results are obtained as a major factor in improving the performance of the device (in particular, driving voltage and life span).

Accordingly, it can be seen that the inventive compound having a specific substituent introduced into the comparative compounds has far superior performance to the conventional compounds in terms of driving voltage, efficiency and lifespan.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas comprised within the scope equivalent to the claims belong to the present invention.

| Reference Numerals | | | |
|---|---|---|---|
| 100: | organic electric element, | 110: | substrate |
| 120: | the first electrode(anode), | 130: | the hole injection layer |
| 140: | the hole transport layer, | 141: | a buffer layer |
| 150: | the emitting layer, | 151: | the emitting auxiliary layer |
| 160: | the electron transport layer, | 170: | the electron injection layer |
| 180: | the second electrode(cathode) | | |

What is claimed is:

1. A compound of Formula (1):

Formula (1)

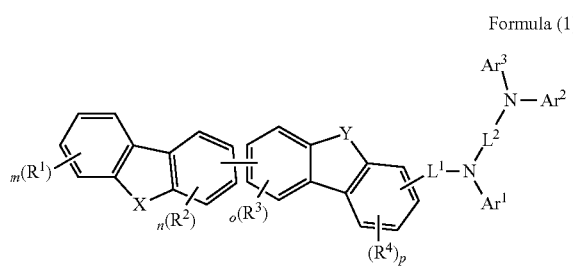

wherein:

1) m is an integer of 0 to 4, and n, o and p are an integer of 0 to 3, 2) when m, n, o and p are 1 or more, $R^1$, $R^2$, $R^3$, and $R^4$ are each independently selected from the group consisting of hydrogen; deuterium; a halogen; a $C_6$-$C_{60}$ aryl group; a fluorenyl group; a $C_2$-$C_{60}$ heterocyclic group comprising at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group;

when m, n, o and p are 2 or more, adjacent $R^1$s or adjacent Res or adjacent $R^3$s or adjacent $R^4$s are optionally combined to each other to form an aromatic or a heteroaromatic ring, 3) X is O, S, or CR'R", and Y is O, NR' or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; and R' and R" are optionally combined to each other to form a spiro ring, 4) $L^1$ is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group, 5) $L^2$ is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group, 6) $Ar^1$, $Ar^2$ and $Ar^3$ are each independently selected from the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group, wherein $Ar^2$ and $Ar^3$, $Ar^3$ and $L^2$, $Ar^2$ and $L^2$, $Ar^1$ and $L^1$, or $Ar^1$ and $L^2$ are optionally bonded to each other to form a ring, wherein the aryl group, fluorenyl group, arylene group, heterocyclic group, fused ring group, alkyl group, alkenyl group, alkoxy group or aryloxy group in $R^1$ to $R^4$, R', R", $L^1$, $L^2$ and $Ar^1$ to $Ar^3$ are optionally substituted with one or more substituents selected from the group consisting of deuterium; halogen; a silane group substituted or unsubstituted with $C_1$-$C_{20}$ alkyl group or $C_6$-$C_{20}$ aryl group; siloxane group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine to each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination thereof.

2. The compound of claim 1, wherein the compound of Formula (1) is represented by one of Formulas (2) to (5):

Formula (2)

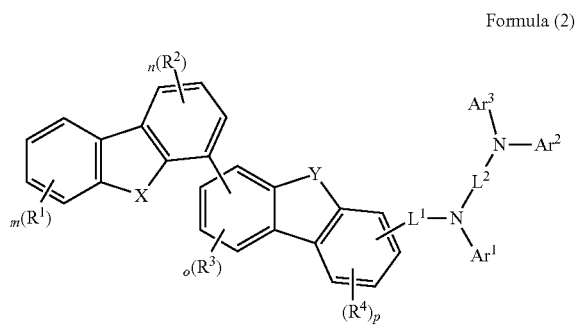

Formula (3)

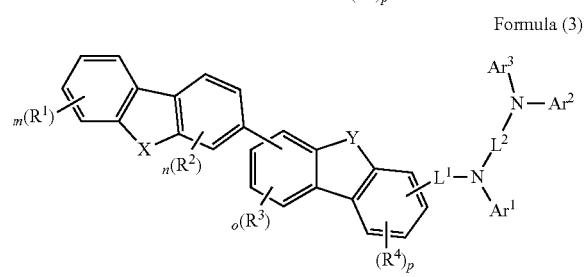

Formula (4)

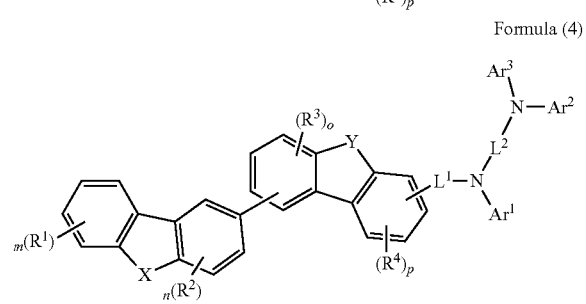

Formula (5)

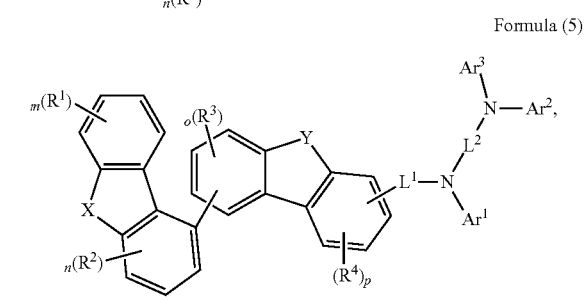

wherein $R^1$, $R^2$, $R^3$, $R^4$, m, n, o, p, $L^1$, $L^2$, $Ar^1$, $Ar^2$, $Ar^3$, X and Y are the same as defined in claim 1.

3. The compound of claim 1, wherein the compound of Formula (1) is represented by one of Formulas (6) to (9):

Formula (6)
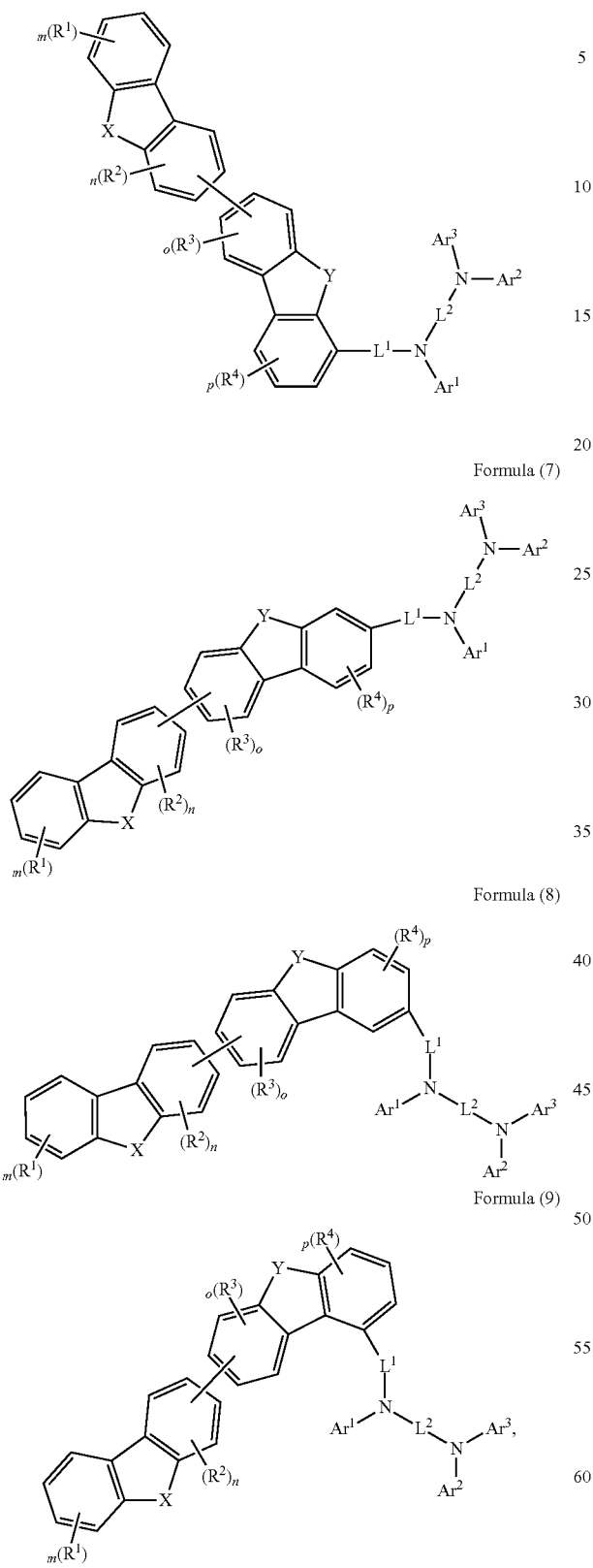
Formula (7)
Formula (8)
Formula (9)
wherein $R^1$, $R^2$, $R^3$, $R^4$, m, n, o, p, $L^1$, $L^2$, $Ar^1$, $Ar^2$, $Ar^3$, X and Y are the same as defined in claim 1.
4. The compound of claim 1, wherein the Y-containing ring in Formula (1) is represented by one of Formulas [A-1] to [A-16]:
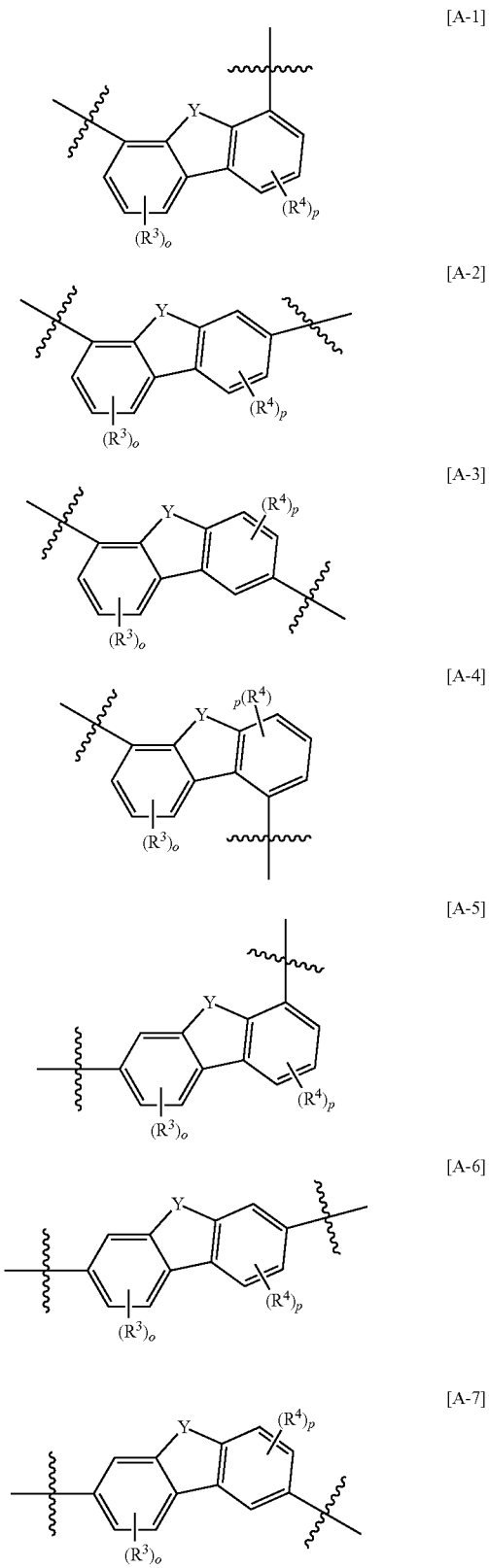
[A-1]
[A-2]
[A-3]
[A-4]
[A-5]
[A-6]
[A-7]

[A-8] 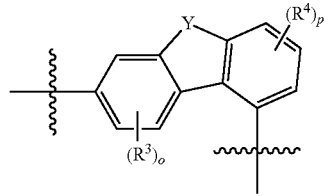
[A-9] 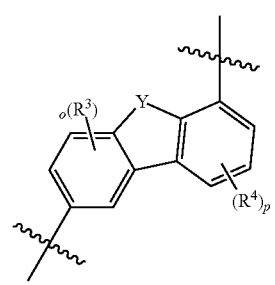
[A-10] 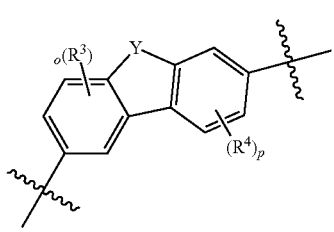
[A-11] 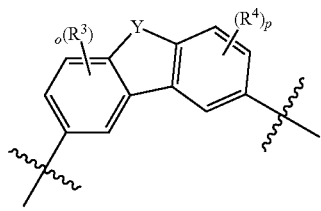
[A-12] 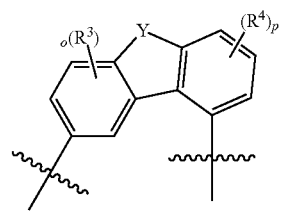
[A-13] 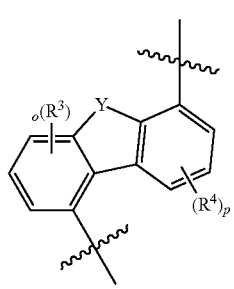
[A-14] 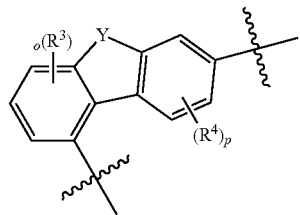
[A-15] 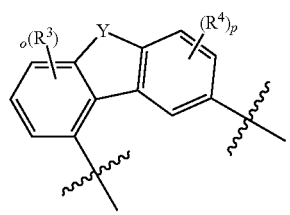
[A-16] 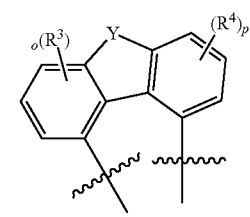
wherein $R^3$, $R^4$, o, p and Y are the same as defined in claim 1.
5. The compound of claim 1, wherein the compound of Formula (1) is represented by one of Formula (10), Formula (11) and Formula (13):
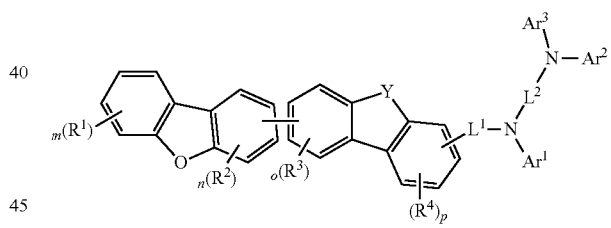
Formula (10)
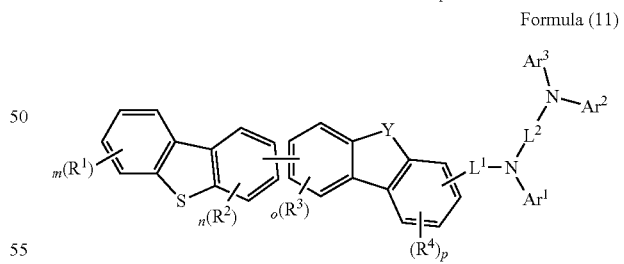
Formula (11)
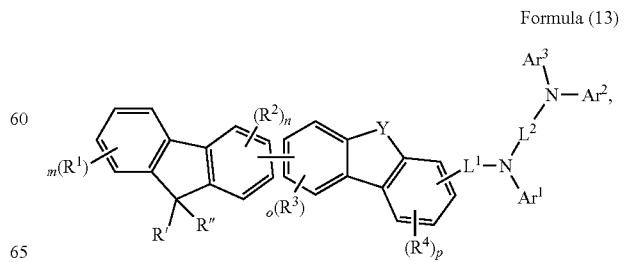
Formula (13)

wherein $R^1$, $R^2$, $R^3$, $R^4$, m, n, o, p, $L^1$, $L^2$, $Ar^1$, $Ar^2$, $Ar^3$, X and Y are the same as defined in claim 1.

6. The compound of claim 1, wherein the compound of Formula (1) is represented by one of Formula (14), Formula (16) and Formula (17):

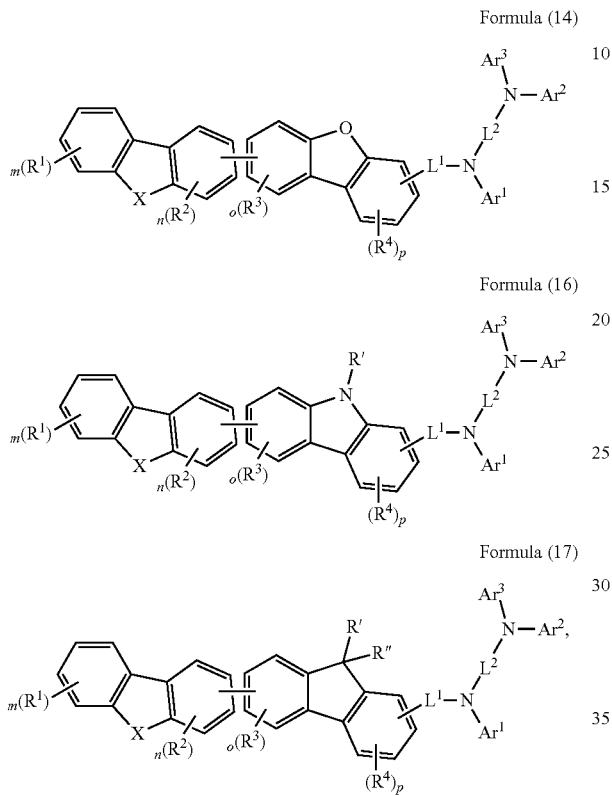

Formula (14)

Formula (16)

Formula (17)

wherein $R^1$, $R^2$, $R^3$, $R^4$, m, n, o, p, $L^1$, $L^2$, $Ar^1$, $Ar^2$, $Ar^3$, and X are the same as defined in claim 1.

7. The compound of claim 1, wherein $L^1$ and $L^2$ in Formula (1) are selected from the group consisting of Formula (B-1) to Formula (B-12):

(B-1)

(B-2)

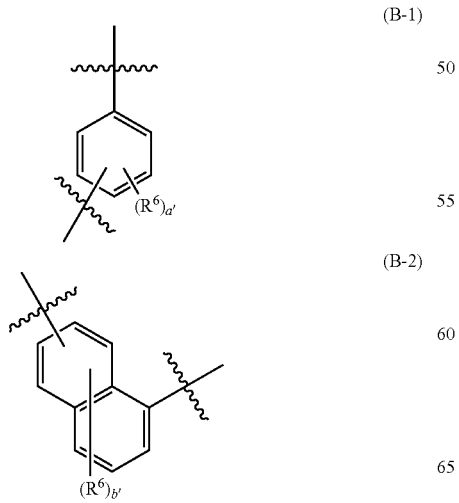

(B-3)

(B-4)

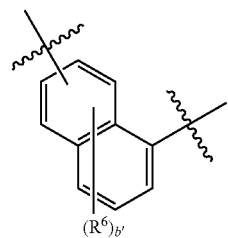

(B-5)

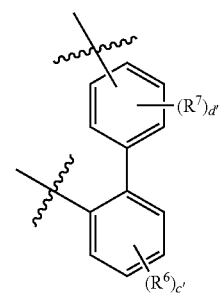

(B-6)

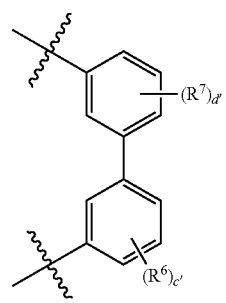

(B-7)

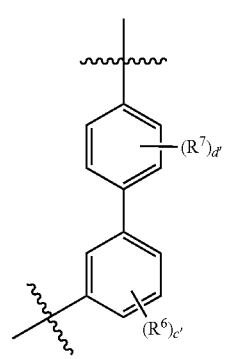

-continued

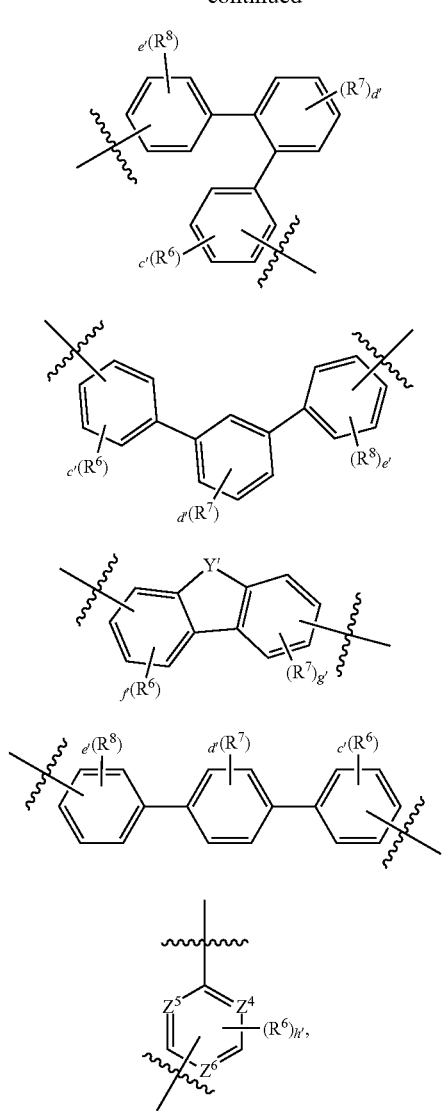

wherein:
1) a', c', d' and e' are each an integer of 0 to 4, b' is an integer of 0 to 6, h' is an integer of 0 to 1, and f' and g' are each an integer of 0 to 3,
2) $R^6$, $R^7$ and $R^8$, being the same or different from each other, are each independently selected from the group consisting of deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_5$-$C_{30}$ aryloxy group; and -L'-N($R_a$)($R_b$), wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P, or in the case where a', b', c', d', e', f' and g' are 2 or more and d is 2, $R^6$, $R^7$ and $R^8$ are each in plural being the same or different from each other, and a plurality of $R^6$ or a plurality of $R^7$ or a plurality of $R^8$ may be bonded to each other to form a ring, or adjacent $R^6$ and $R^7$, or adjacent $R^7$ and $R^8$ may be bonded to each other to form an aromatic or a heteroaromatic ring, 3) Y' is NR', O, S, or CR'R", wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; and R' and R" may be bonded to each other to form a spiro ring, 4) $Z^4$, $Z^5$ and $Z^6$ are each independently CR' or N, and at least one is N.

8. The compound of claim 1, wherein at least one of $L^1$ and $L^2$ in Formula (1) is substituted at a meta position.

9. The compound of claim 1, wherein the compound of Formula (1) is selected from the group consisting of Formula (P-123) to Formula (P-125) and Formula (P-128):

P-123

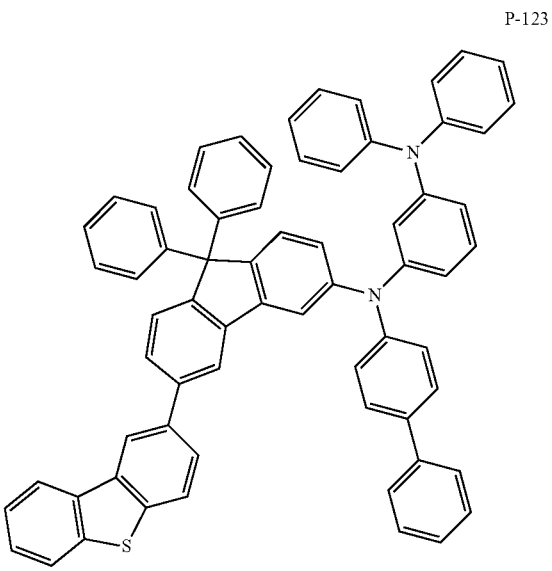

P-124

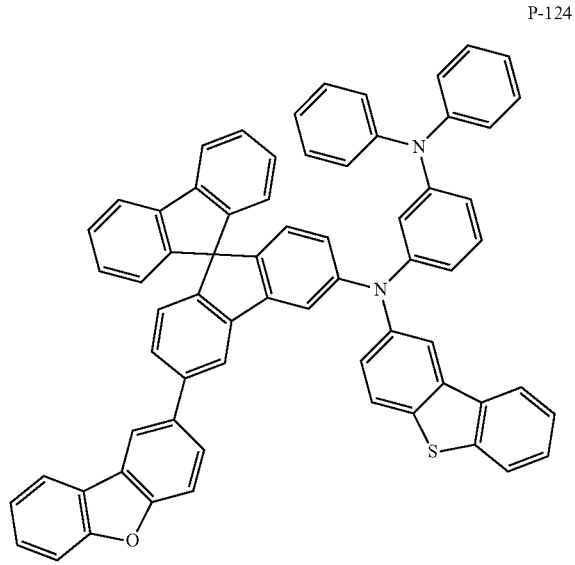

P-125

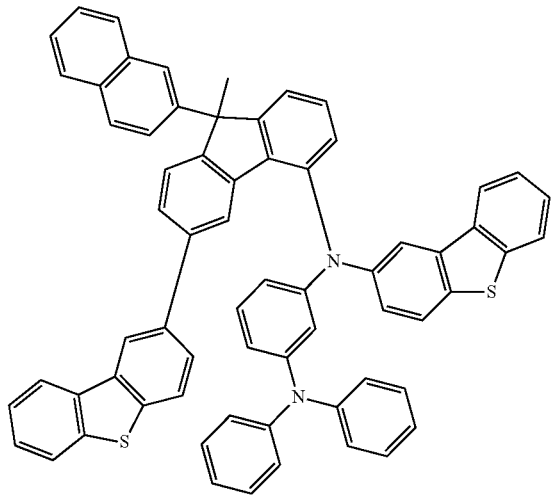

P-128

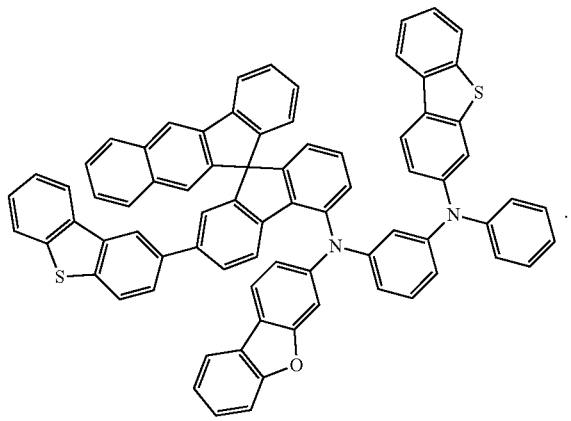

10. An organic electric element comprising a first electrode, a second electrode, and an organic material layer between the first electrode and the second electrode, wherein the organic material layer comprises one or more of a hole injection layer, a hole transport layer, an emitting-auxiliary layer, an emitting layer, an hole blocking layer, an electronic auxiliary layer, and an electron transport layer, and wherein the organic material layer comprises the compound according to claim 1.

11. The organic electric element of claim 10, wherein the organic layer is a hole transport layer or an emitting-auxiliary layer, and wherein the compound is a single compound or a mixture of two or more compounds having different structures in the hole transport layer or in the emitting-auxiliary layer.

12. The organic electric element of claim 10, wherein the organic electric element further comprises a light efficiency enhancing layer formed on the side of the first electrode and/or the second electrode, the side being opposite to the organic material layer not facing the organic material layer.

13. The organic electric element of claim 10, wherein the organic material layer is formed by a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

14. An electronic device comprising a display device including the organic electric element according to claim 10; and a control unit for driving the display device.

15. The electronic device of claim 14, wherein the organic electric element is at least one of an OLED, an organic solar cell, an organic photo conductor, an organic transistor and an element for monochromic or white illumination.

16. A compound of Formula (1):

Formula (1)

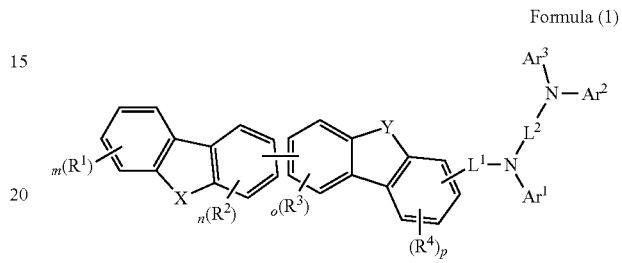

wherein:
1) m is an integer of 0 to 4, and n, o and p are an integer of 0 to 3,
2) $R^1$, $R^2$, $R^3$, and $R^4$ are each independently selected from the group consisting of hydrogen; deuterium; a halogen; a $C_6$-$C_{60}$ aryl group; a fluorenyl group; a $C_2$-$C_{60}$ heterocyclic group comprising at least one hetero atom of O, N, S, Si and P; a fused ring group of a $C_3$-$C_{60}$ aliphatic ring and a 06-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'—N($R_a$)($R_b$), wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P, or
when m, n, o and p are 2 or more, adjacent $R^1$s or adjacent $R^2$s or adjacent $R^3$s or adjacent $R^4$s are optionally combined to each other to form an aromatic or a heteroaromatic ring,
3) X is O, S, or CR'R", and Y is S, wherein R' and R" are independently hydrogen; a $C_6$-$C_{60}$ aryl group; a fluorenyl group; a $C_3$-$C_{60}$ heterocyclic group; or a $C_1$-$C_{50}$ alkyl group; and R' and R" are optionally combined to each other to form a spiro ring,
4) $L^1$ is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group,
5) $L^2$ is selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group, and
6) $Ar^1$, $Ar^2$ and $Ar^3$ are each independently selected from the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring;

a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$), wherein $Ar^2$ and $Ar^3$, $Ar^3$ and $L^2$, $Ar^2$ and $L^2$, $Ar^1$ and $L^1$, or $Ar^1$ and $L^2$ are optionally bonded to each other to form a ring, with the proviso that: (i) at least one of m, n, o and p is 2 or more, and adjacent $R_1$s or adjacent $R^2$s or adjacent $R^3$s or adjacent $R^4$s are combined to each other to form a $C_6$-$C_{60}$ aromatic ring or a $C_2$-$C_{60}$ heterocyclic, or (ii) at least one of $Ar^1$, $Ar^2$ and $Ar^3$ includes a dibenzofuran or dibenzothiophen group, wherein the aryl group, fluorenyl group, arylene group, heterocyclic group, fused ring group, alkyl group, alkenyl group, alkoxy group or aryloxy group in $R^1$ to $R^4$, R', R", $L^1$, $L^2$ and $Ar^1$ to $Ar^3$ are optionally substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'—N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine to each other and form a saturated or unsaturated ring, wherein the term 'ring' means $C_3$-$C_{60}$ aliphatic ring or $C_6$-$C_{O60}$ aromatic ring or a $C_2$-$C_{60}$ heterocyclic ring or a fused ring formed by the combination thereof.

17. The compound of claim 16, wherein the compound of Formula (1) is represented by one of Formulas (2) to (5):

Formula (2)

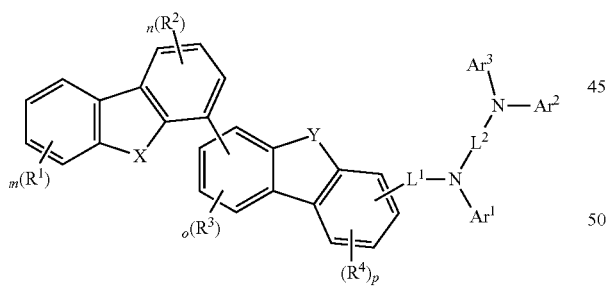

Formula (3)

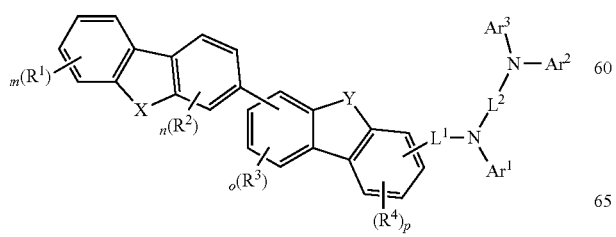

Formula (4)

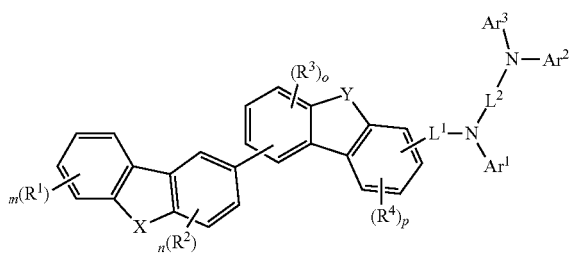

Formula (5)

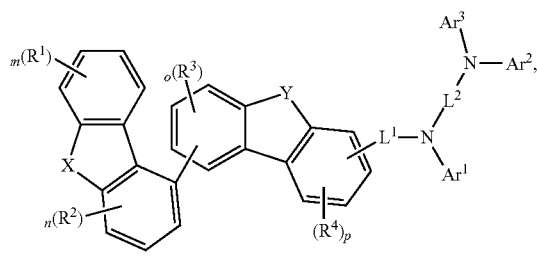

wherein $R^1$, $R^2$, $R^3$, $R^4$, m, n, o, p, $L^1$, $L^2$, $Ar^1$, $Ar^2$, $Ar^3$, X and Y are the same as defined in claim 16.

18. The compound of claim 16, wherein the compound of Formula (1) is represented by one of Formulas (6) to (9):

Formula (6)

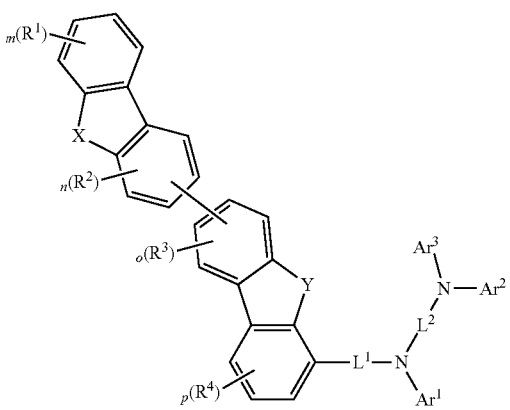

149
-continued

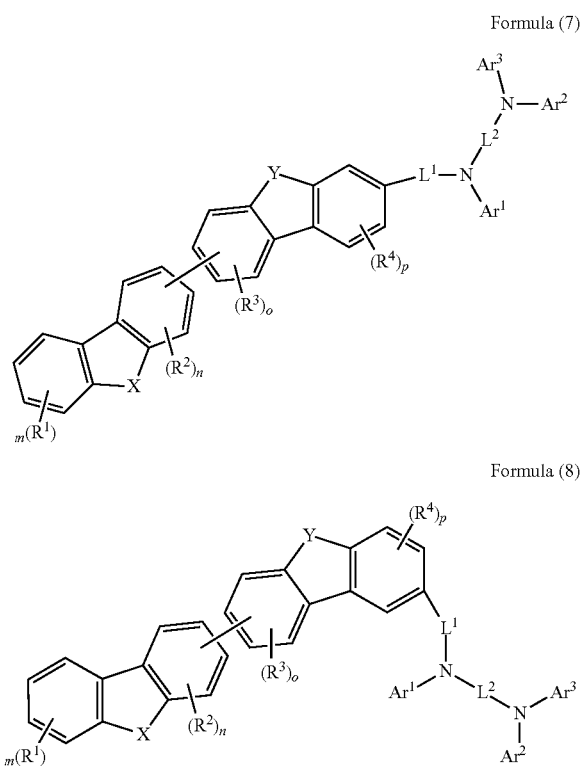

Formula (7)

Formula (8)

150
-continued

Formula (9)

wherein $R^1$, $R^2$, $R^3$, $R^4$, m, n, o, p, $L^1$, $L^2$, $Ar^1$, $Ar^2$, $Ar^3$, X and Y are the same as defined in claim 16.

19. An organic electric element comprising a first electrode, a second electrode, and an organic material layer between the first electrode and the second electrode, wherein the organic material layer comprises one or more of a hole injection layer, a hole transport layer, an emitting-auxiliary layer, an emitting layer, an hole blocking layer, an electronic auxiliary layer, and an electron transport layer, and wherein the organic material layer comprises the compound according to claim 16.

20. An electronic device comprising a display device including the organic electric element according to claim 19; and a control unit for driving the display device.

* * * * *

UNITED STATES PATENT AND TRADEMARK OFFICE
CERTIFICATE OF CORRECTION

PATENT NO. : 11,950,502 B2
APPLICATION NO. : 17/233438
DATED : April 2, 2024
INVENTOR(S) : Park et al.

It is certified that error appears in the above-identified patent and that said Letters Patent is hereby corrected as shown below:

In the Claims

Column 135, Claim 1, Line 38:
Please delete "Res"
And replace with -- $R^2s$ --

Column 143, Claim 7, Line 58:
Please delete "$C_5$-$C_{30}$"
And replace with -- $C_6$-$C_{30}$ --

Column 146, Claim 16, Line 33:
Please delete "$O6$-$C_{60}$"
And replace with -- $C_6$-$C_{60}$ --

Column 147, Claim 16, Line 7:
Please delete "$R_1s$"
And replace with -- $R^1s$ --

Signed and Sealed this
Fourth Day of June, 2024

Katherine Kelly Vidal
*Director of the United States Patent and Trademark Office*